(12) United States Patent
Molina et al.

(10) Patent No.: US 12,571,790 B2
(45) Date of Patent: Mar. 10, 2026

(54) BIOENERGETIC PROFILING OF CIRCULATING BLOOD CELLS AND SYSTEMS, DEVICES, AND METHODS RELATING THERETO

(71) Applicant: WAKE FOREST UNIVERSITY HEALTH SCIENCES, Winston-Salem, NC (US)

(72) Inventors: Anthony J. A. Molina, San Diego, CA (US); Jeff Williamson, Advance, NC (US); Stephen Kritchevsky, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 1958 days.

(21) Appl. No.: 16/376,803

(22) Filed: Apr. 5, 2019

(65) Prior Publication Data

US 2019/0361003 A1 Nov. 28, 2019

Related U.S. Application Data

(63) Continuation of application No. 15/302,220, filed as application No. PCT/US2015/024795 on Apr. 7, 2015, now abandoned.

(60) Provisional application No. 62/075,412, filed on Nov. 5, 2014, provisional application No. 61/976,417, filed on Apr. 7, 2014.

(51) Int. Cl.
| | |
|---|---|
| G01N 33/49 | (2006.01) |
| A61B 5/11 | (2006.01) |
| A61B 5/145 | (2006.01) |
| A61B 5/1455 | (2006.01) |
| C12Q 1/00 | (2006.01) |
| G01N 33/50 | (2006.01) |
| G16H 10/40 | (2018.01) |
| G16H 40/60 | (2018.01) |
| G16H 50/30 | (2018.01) |
| G16Z 99/00 | (2019.01) |
| A61B 5/22 | (2006.01) |

(52) U.S. Cl.
CPC .......... G01N 33/4925 (2013.01); A61B 5/112 (2013.01); A61B 5/14542 (2013.01); A61B 5/14551 (2013.01); C12Q 1/00 (2013.01); G01N 33/5005 (2013.01); G01N 33/5079 (2013.01); G01N 33/5091 (2013.01); G01N 33/5094 (2013.01); G16H 10/40 (2018.01); G16H 40/60 (2018.01); G16H 50/30 (2018.01); G16Z 99/00 (2019.02); A61B 5/224 (2013.01); A61B 2503/08 (2013.01); G01N 2800/52 (2013.01); G01N 2800/7042 (2013.01)

(58) Field of Classification Search
CPC ........... G01N 33/5079; G01N 33/5091; G01N 33/5094
See application file for complete search history.

(56) References Cited

U.S. PATENT DOCUMENTS

| | | | |
|---|---|---|---|
| 7,276,351 B2 | 10/2007 | Teich et al. | |
| 7,638,321 B2 | 12/2009 | Teich et al. | |
| 7,851,201 B2 | 12/2010 | Teich et al. | |
| 8,202,702 B2 | 6/2012 | Neilson et al. | |
| 8,658,349 B2 | 2/2014 | Teich et al. | |
| 8,697,431 B2 | 4/2014 | Teich et al. | |
| 2011/0027247 A1* | 2/2011 | Narain | .................... A61P 35/00 |
| | | | 424/94.1 |
| 2014/0186876 A1 | 7/2014 | Teich et al. | |
| 2014/0248650 A1 | 9/2014 | Teich et al. | |

FOREIGN PATENT DOCUMENTS

| | | |
|---|---|---|
| WO | 2011027221 | 3/2011 |
| WO | 2015157345 | 10/2015 |

OTHER PUBLICATIONS

Karl RC, Schreiber R, Boulware D, Baker S, Coppola D. Factors affecting morbidity, mortality, and survival in patients undergoing Ivor Lewis esophagogastrectomy. Ann Surg. May 2000;231(5):635-43. doi: 10.1097/00000658-200005000-00003. PMID: 10767784 ; PMCID: PMC1421050. (Year: 2000).*

F.E. Turrentine et al., Surgical risk factors, morbidity, and mortality in elderly patients, Critical Reviews in Oncology/Hematology, vol. 68, Supplement 2,2008,p. S13, ISSN 1040-8428, https://doi.org/10.1016/S1040-8428(08)70016-7 (Year: 2008).*

Rosca MG, Hoppel CL. Mitochondrial dysfunction in heart failure. Heart Fail Rev. Sep. 2013; 18(5):607-22. doi: 10.1007/s10741-012-9340-0. PMID: 22948484; PMCID: PMC3855291 (Year: 2013).*

International Patent Application No. PCT/US2015/024795, International Search Report and Written Opinion mailed Feb. 17, 2016.

88.5 WFDD SciWorks Radio, "Adding Life to Your Years", Retrieved from Internet: https://www.wfdd.org/story/adding-life-your-years, Mar. 28, 2014, 5 pages.

Abellan et al., "Gait Speed at Usual Pace as a Predictor of Adverse Outcomes in Community-Dwelling Older People an International Academy on Nutrition and Aging (Iana) Task Force", J. Nutr. Health Aging, vol. 13, No. 10, Dec. 2009, pp. 881-889.

Altmann , "Observational Study of Behavior: Sampling Methods", Behaviour, vol. 49, No. 3, Jan. 1, 1974, pp. 227-267.

(Continued)

*Primary Examiner* — Ruth A Davis

(74) *Attorney, Agent, or Firm* — Kilpatrick Townsend & Stockton LLP

(57) ABSTRACT

The invention relates generally to systems and methods of bioenergetic profiling, uses thereof, and systems and devices relating thereto. In particular, methods of the invention are useful in assessing wellness, particularly in elderly subjects. Described are systems and methods of assessing likelihood of subject morbidity, life expectancy, positive clinical outcome, responsiveness to treatment, and certain disease states as well as of selecting treatment strategy, improving outcome to treatment strategy, and treating subjects with low bioenergetic profiles. Also described are devices and systems for measuring respiratory capacity.

15 Claims, 23 Drawing Sheets

(56)                    References Cited

OTHER PUBLICATIONS

Andreux et al., "Pharmacological Approaches to Restore Mitochondrial Function", Nature Reviews Drug Discovery, vol. 12, No. 6, May 13, 2013, pp. 465-483.

Barazzoni et al., "Effects of Aging on Mitochondrial DNA Copy Number and Cytochrome c Oxidase Gene Expression in Rat Skeletal Muscle, Liver, and Heart", The Journal of Biological Chemistry, vol. 275, No. 5, Feb. 4, 2000, pp. 3343-3347.

Biino et al., "Influence of Age, Sex and Ethnicity on Platelet Count in Five Italian Geographic Isolates: Mild Thrombocytopenia may be Physiological", Br J Haematol., vol. 157, No. 3, May 2012, pp. 384-387.

Brand et al., "Assessing Mitochondrial Dysfunction in Cells", Biochem J., vol. 435, Apr. 15, 2011, pp. 297-312.

Cann et al., "Clinicopathologic Characterization of Naturally Occurring Diabetes Mellitus in Vervet Monkeys", Veterinary Pathology, vol. 47, No. 4, Jul. 2010, pp. 713-718.

Cesari et al., "Lipoprotein Peroxidation and Mobility Limitation", Arch Intern Med., vol. 165, No. 18, Oct. 10, 2005, pp. 2148-2154.

Chacko et al., "The Bioenergetic Health Index: A New Concept In Mitochondrial Translational Research", Clinical Science, vol. 127, No. 6, Sep. 2014, pp. 367-373.

Chance et al., "A Method for the Localization of Sites for Oxidative Phosphorylation", Nature, vol. 176, No. 4475, Aug. 6, 1955, pp. 250-254.

Chance et al., "A Simple and Rapid Assay of Oxidative Phosphorylation", vol. 175, No. 4469, Jun. 25, 1955, pp. 1120-1121.

Choi et al., "Force-Generation Capacity of Single Vastus Lateralis Muscle Fibers and Physical Function Decline With Age in African Green Vervet Monkeys", J Gerontal. A Biol. Sci. Med. Sci., vol. 68, No. 3, Mar. 2013, pp. 258-267.

Coen et al., "Skeletal Muscle Mitochondrial Energetics are Associated with Maximal Aerobic Capacity and Walking Speed in Older Adults", The Journals of Gerontology Series A Biological Sciences and Medical Sciences, vol. 68, No. 4, Oct. 9, 2012, pp. 447-455.

Cooper et al., "Objective Measures of Physical Capability and Subsequent Health: A Systematic Review", Age and Ageing, vol. 40, No. 1, Jan. 1, 2011, pp. 14-23.

Corsonello et al., "Prognostic Significance of the Short Physical Performance Battery in Older Patients Discharged from Acute Care Hospitals", Rejuvenation Research, vol. 15, No. 1, Feb. 2012, pp. 41-48.

Crimmins et al., "Biomarkers Related to Aging in Human Populations", Adv. Clin. Chem., vol. 46, May 7, 2018, pp. 161-216.

Crujeiras et al., "Differential Expression of Oxidative Stress and Inflammation Related Genes in Peripheral Blood Mononuclear Cells in Response to a Low-Calorie Diet: A Nutrigenomics Study", A Journal of Integrative Biology, vol. 12, No. 4, Nov. 30, 2008, pp. 251-261.

Daly, "Determinants of Platelet Count in Humans", Haematologica, vol. 96, No. 1, Jan. 2011, pp. 10-13.

Desborough, "The Stress Response to Trauma and Surgery", British Journal of Anaesthesia, vol. 85, No. 1, Jul. 2000, pp. 109-117.

Era et al., "Postural Sway During Standing and Unexpected Disturbance of Balance in Random Samples of Men of Different Ages", Journal of Gerontology, vol. 40, No. 3, May 1, 1985, pp. 287-295.

Feng et al., "Myosin Heavy Chain Isoform Expression in the Vastus Lateralis Muscle of Aging African Green Vervet Monkeys", Experimental Gerontology, vol. 47, No. 8, Aug. 2012, pp. 601-607.

Ferrucci et al., "Subsystems Contributing to the Decline in Ability to Walk: Bridging the Gap Between Epidemiology and Geriatric Practice in the InCHIANTI Study", J Am Geriatr Soc., vol. 48, No. 12, Dec. 2000, pp. 1618-1625.

Fink et al., "Endothelial Cell and Platelet Bioenergetics: Effect of Glucose and Nutrient Composition", PLoS One, vol. 7, No. 6, e39430, Jun. 22, 2012, pp. 1-12.

Gabriel et al., "Test-Retest Reliability and Validity of the 400-Meter Walk Test in Healthy, Middle-Aged Women", Journal of Physical Activity and Health, vol. 7, No. 5, Sep. 2010, pp. 649-657.

Guralnik et al., "Lower Extremity Function and Subsequent Disability: Consistency Across Studies, Predictive Models, and Value of Gait Speed Alone Compared With the Short Physical Performance Battery", The Journals of Gerontology: Series A, vol. 55, No. 4, Medical Sciences, Apr. 1, 2000, pp. M221-M231.

Guralnik et al., "Physical Performance Measures in the Assessment of Older Persons", Aging (Milano), vol. 6, No. 5, Oct. 1994, pp. 303-305.

Hansford et al., "The Effect of Ca2+ on the Oxidation of Glycerol Phosphate by Blowfly Flight-Muscle Mitochondria", Biochem Biophys Res Commun., vol. 27, No. 6, Jun. 23, 1967, pp. 686-692.

Hardy et al., "Ability to Walk 1/4 Mile Predicts Subsequent Disability, Mortality, and Health Care Costs", J Gen Intern Med., vol. 26, No. 2, Feb. 2011, pp. 130-135.

Hardy et al., "Improvement in Usual Gait Speed Predicts Better Survival in Older Adults", Am. Geriatr. Soc., vol. 55, No. 11, Nov. 2007, pp. 1727-1134.

Hearps et al., "Aging is Associated With Chronic Innate Immune Activation and Dysregulation of Monocyte Phenotype and Function", Aging Cell, vol. 11, No. 5, Oct. 2012, pp. 867-875.

Hill et al., "Regulation of Vascular Smooth Muscle Cell Bioenergetic Function by Protein Glutathiolation", Biochim. Biophys. Acta, vol. 1797 No. 2, Feb. 2010, pp. 285-295.

Japiassu et al., "Bioenergetic failure of human peripheral blood monocytes in patients with septic shock is mediated by reduced F1Fo adenosine-5 1-triphosphate synthase activity", Critical Care Medicine, vol. 39. No. 5, May 2011, pp. 1056-1063.

Jayachandran et al., "Loss of Estrogen Receptor Beta Decreases Mitochondrial Energetic Potential and Increases Thrombogenicity of Platelets in Aged Female Mice", Age (Dordr.), vol. 32, No. 1, Mar. 2010, pp. 109-121.

Jayachandran et al., "Platelet Characteristics Change with Aging: Role of Estrogen Receptor Beta", J Gerontal. A Bioi. Sci. Med. Sci., vol. 60, No. 7, Jul. 2005, pp. 815-819.

Joseph et al., "The impact of aging on mitochondrial function and biogenesis pathways in skeletal muscle of sedentary high- and low-functioning elderly individuals", Aging Cell, vol. 11, No. 5, Oct. 1, 2012, pp. 801-809.

Kayo et al., "Influences of Aging and Caloric Restriction on the Transcriptional Profile of Skeletal Muscle from Rhesus Monkeys", Proc. Natl. Acad. Sci., vol. 98, No. 9, Apr. 24, 2001, pp. 5093-5098.

Kramer et al., "Bioenergetics and the Oxidative Burst: Protocols for the Isolation and Evaluation of Human Leukocytes and Platelets", Journal of Visualized Experiments, vol. 85, Mar. 27, 2014, 10 pages.

Kuhnke et al., "Bioenergetics of Immune Cells to Assess Rheumatic Disease Activity and Efficacy of Glucocorticoid Treatmen", Annals of the Rheumatic Diseases, vol. 62, Feb. 2003, pp. 133-139.

Lehmann et al., "Simultaneous Measurement of Cellular Respiration and Acidification with a Single CMOS ISFET", Biosens. Bioelectron., vol. 16, No. 3, May 2001, pp. 195-203.

Leng et al., "Associations of Neutrophil and Monocyte Counts with Frailty in Communitydwelling Disabled Older Women: Results from the Women's Health and Aging Studies I", Exp. Gerontal. vol. 44, No. 8, Aug. 2009, pp. 511-516.

Levine, "Modeling the Rate of Senescence: Can Estimated Biological Age Predict Mortality More Accurately Than Chronological Age", J Gerontal. A Bioi. Sci. Med. Sci., vol. 68, No. 8, 2013, pp. 667-674.

Lowell et al., "Mitochondrial Dysfunction and Type 2 Diabetes", Science, vol. 307, No. 5708, Jan. 2005, pp. 384-387.

Maynard et al., "Relationships Between Human Vitality and Mitochondrial Respiratory Parameters, Reactive Oxygen Species Production and dNTP Levels in Peripheral Blood Mononuclear Cells", Aging (Albany NY), vol. 5, No. 11, Nov. 2013, pp. 850-864.

Nakamura et al., "A Method for Identifying Biomarkers of Aging and Constructing an Index of Biological Age in Humans", J Gerontal. A Bioi. Sci. Me d. Sci., vol. 62, No. 10, Oct. 2007, pp. 1096-1105.

Nicholls et al., "Bioenergetics of Mitochondria in Cultured Neurons and Their Role in Glutamate Excitotoxicity", J Neurosci. Res., vol. 85, No. 15, Nov. 15, 2007, pp. 3206-3212.

(56) References Cited

OTHER PUBLICATIONS

Nicklas et al., "Relationship of Physical Function to Vastus Lateralis Capillary Density and Metabolic Enzyme Activity in Elderly Men and Women", Aging Clin. Exp. Res., vol. 20, No. 4, Aug. 2008, pp. 302-309.

Ostir et al., "Assessing Gait Speed in Acutely Ill Older Patients Admitted to an Acute Care for Elders Hospital Unit", Arch. Intern. Med., vol. 172, No. 4, Feb. 27, 2012, pp. 353-358.

Patti et al., "Coordinated Reduction of Genes of Oxidative Metabolism in Humans with Insulin Resistance and Diabetes: Potential Role of PGC1 and NRF1", Proc. Natl. Acad. Sci., vol. 100, No. 14, Jul. 8, 2003, pp. 8466-8471.

Penninx et al., "Lower Extremity Performance in Nondisabled Older Persons as a Predictor of Subsequent Hospitalization", J Gerontal. A Bioi. Sci. Med. Sci., vol. 55, No. 11, Nov. 1, 2000, pp. M691-M697.

Peterson et al., "Skeletal Muscle Mitochondria and Aging: A Review", J. Aging Res., vol. 2012, 2012, 21 pages.

Phillips et al., "Simultaneous Quantification of Mitochondrial DNA Copy Number and Deletion Ratio: A Multiplex Real-Time PCR Assay", Sci. Rep., vol. 4, No. 3887, Jan. 27, 2014, pp. 1-7.

Radom-Aizik et al., "Brief Bout of Exercise Alters Gene Expression in Peripheral Blood Mononuclear Cells of Early- and Late-Pubertal Males", Pediatr. Res., vol. 65, No. 4, Apr. 2009, pp. 447-452.

Rao et al., "Mitochondrial DNA Injury and Mortality in Hemodialysis Patients", J. Am. Soc. Nephrol., vol. 20, No. 1, Jan. 2009, pp. 189-196.

Rogers et al., "High Throughput Microplate Respiratory Measurements Using Minimal Quantities of Isolated Mitochondria", PLoS One, vol. 6, No. 7, e21746, Jul. 2011, pp. 1-12.

Rolo et al., "Diabetes and Mitochondrial Function: Role of Hyperglycemia and Oxidative Stress", Toxicol. Appl. Pharmacal., vol. 212, No. 2, Apr. 15, 2006, pp. 167-178.

Rosenfeldt et al., "Coenzyme Q10 Therapy before Cardiac Surgery Improves Mitochondrial Function and in Vitro Contractility of Myocardial Tissue", The Journal of Thoracic and Cardiovascular Surgery, vol. 129, No. 1, 2005, pp. 25-32.

Rudkowska et al., "Validation of the use of Peripheral Blood Mononuclear Cells as Surrogate Model for Skeletal Muscle Tissue in Nutrigenomic Studies", Omics: A Journal of Integrative Biology, vol. 15, No. 1-2, Jan. 30, 2011, pp. 1-7.

Sansbury et al., "Responses of Hypertrophied Myocytes to Reactive Species: Implications for Glycolysis and Electrophile Metabolism", Biochem J., vol. 435, No. 2, Apr. 15, 2011, pp. 519-528.

Seahorse Bioscience, Application Note—Bioenergetic Analysis of Suspension Cells: Hematopoietic Stem Cells and Lymphocytes, Available online at: appnote-suspension-stem-cells-lymphocytes. pdf, Aug. 1, 2016, 4 pages.

Seahorse Bioscience, "How XF Analyzers Work", Available online at: http://www.seahorsebio.com/products/how-xf-works.php, Mar. 25, 2015, pp. 1-2.

Seahorse Bioscience, "XFe Extracellular Flux Analyzers", Seahorse Bioscience, Available online at: http://www.seahorsebio.com/products/instruments/analyzers.php, Mar. 25, 2015, 2 pages.

Seahorse Bioscience, "XFp Extracellular Flux Analyzers", Seahorse Bioscience, Available online at: http://www.seahorsebio.com/products/instruments/xfp.php, Mar. 25, 2015, 2 pages.

Shaw et al., "Integrated Proteomic and Metabolic Analysis of Breast Cancer Progression", PLOS ONE, vol. 8, No. 9, Sep. 27, 2013, p. e76220.

Shi et al., "Effects of Ageing and Alzheimer's Disease on Mitochondrial Function of Human Platelets", Experimental Gerontology, vol. 43, Jun. 2008, pp. 589-594.

Shively et al., "Aging and Physical Mobility in Group-Housed Old World Monkeys", Age (Dordr.), vol. 34, No. 5, Oct. 2012, pp. 1123-1131.

Short et al., "Decline In Skeletal Muscle Mitochondrial Function With Aging In Humans", Proc Natl Acad Sci U S A, vol. 102, No. 15, Apr. 12, 2012, pp. 5618-5623.

Simonsick et al., "Measuring Fitness in Healthy Older Adults: The Health Abc Long Distance Corridor Walk", Journal of the American Geriatrics Society, vol. 49, No. 11, Nov. 2001, pp. 1544-1548.

Sjovall et al., "Mitochondrial Respiration in Human Viable Platelets—Methodology and Influence of Gender, Age and Storage", Mitochondrian, vol. 13, No. 1, 2013, pp. 7-14.

Sjovall et al., "Patients with Sepsis Exhibit Increased Mitochondrial Respiratory Capacity in Peripheral Blood Immune Cells", Critical Care, vol. 17, Issue 4, R152, 2013, pp. 1-11.

Studenski , "Gait Speed and Survival in Older Adults", JAMA, vol. 305, No. 1, Jan. 5, 2011, pp. 50-58.

Studenski , "What are the Outcomes of Treatment Among Patients With Sarcopenia", J Nutr Health Aging, vol. 13, No. 8, Oct. 2009, pp. 733-736.

Suomalainen et al., "FGF-21 as a Biomarker For Muscle-Manifesting Mitochondrial Respiratory Chain Deficiencies: A Diagnostic Study", Lancet Neural, vol. 10, No. 9, 2011, pp. 806-818.

Swerdlow et al., "The Alzheimer's Diesease Mitochondrial Cascade Hypothesis", J Alzheimers Dis., vol. 20, 2010, pp. 265-279.

Takamura et al., "Gene Expression Profiles In Peripheral Blood Mononuclear Cells Reflect the Pathophysiology of Type 2 Diabetes", Biochemical and Biophysical Research Communications, vol. 361, No. 2, Sep. 21, 2007, pp. 379-384.

Trounce et al., "Decline in Skeletal Muscle Mitochondrial Respiratory Chain Function: Possible Factor in Ageing", Lancet, vol. 1, No. 8639, Mar. 25, 1989, pp. 637-639.

Van Der Windt et al., "Mitochondrial Respiratory Capacity is a Critical Regulator of Cd8+ T Cell Memory Development.", Immunity, vol. 36, No. 1, Jan. 27, 2012, 21 pages.

Vericel et al., "Platelets and Aging I.—Aggregation, Arachidonate Metabolism and Antioxidant Status", Thrombosis Research, vol. 49, No. 3, Feb. 1, 1988, pp. 331-342.

Volpato et al., "Performance-Based Functional Assessment in Older Hospitalized Patients: Feasibility and Clinical Correlates", J Gerontol A Biol Sci Med Sci, vol. 66, No. 1, Dec. 2008, pp. 1393-1398.

Volpato et al., "Predictive Value of the Short Physical Performance Battery Following Hospitalization in Older Patients", Gerontal. A Bioi. Sci. Med. Sci., vol. 66A, No. 1, Jan. 2011, pp. 89-96.

Wang et al., "Role of Pro-Inflammatory Cytokines Released From Microglia in Alzheimer's Disease", Annals of Translational Medicine, vol. 3, No. 10, 2015, pp. 1-15.

Woods et al., "Adiposity Signals and the Control of Energy Homeostasis", Nutrition, vol. 16, No. 10, Oct. 2006, pp. 894-902.

Yadava et al., "Spare Respiratory Capacity Rather Than Oxidative Stress Regulates Glutamate Excitotoxicity After Partial Respiratory Inhibition of Mitochondrial Complex I With Rotenone", Journal of Neuroscience, vol. 27, No. 27, Jul. 4, 2007, pp. 7310-7317.

* cited by examiner

A.
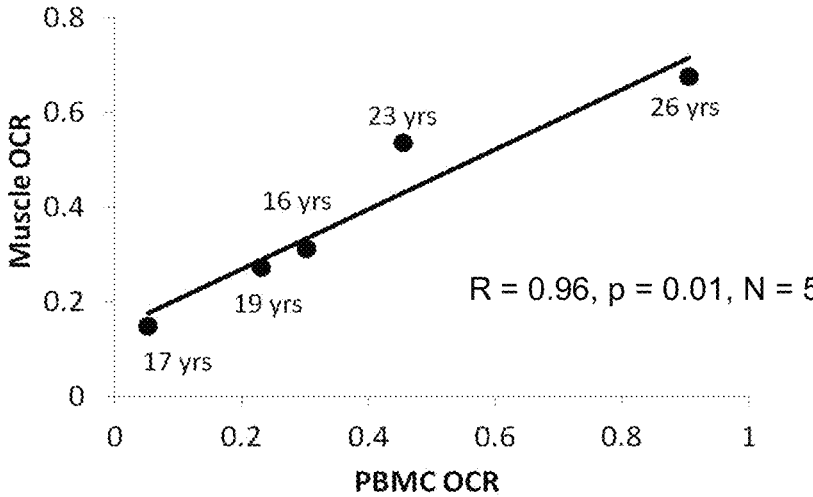
B.
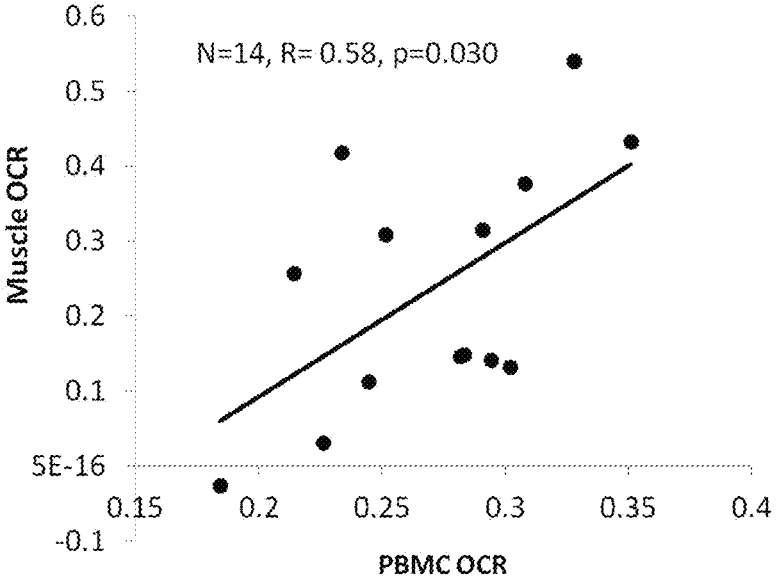
FIG. 3

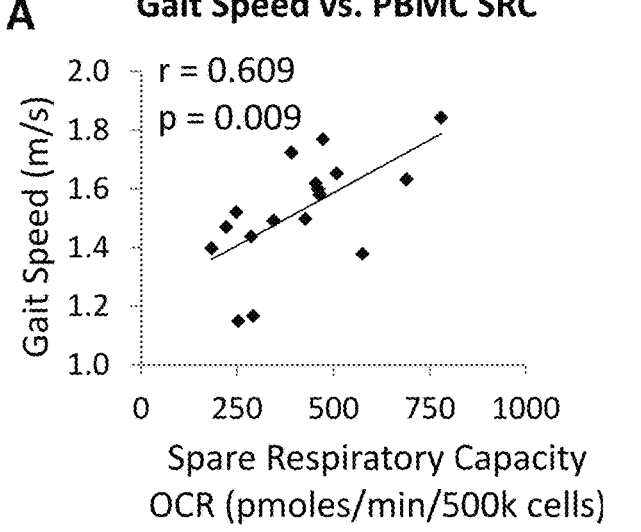
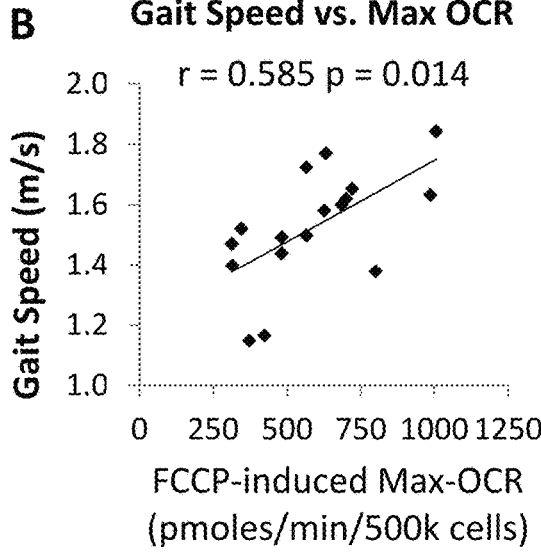
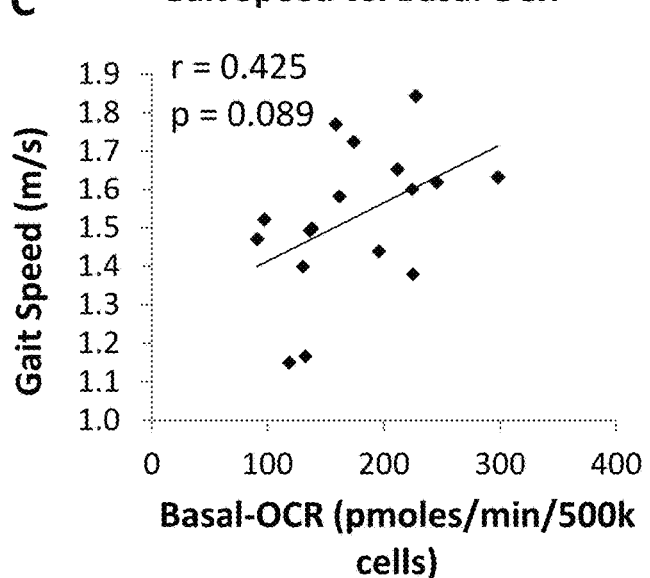
FIG. 5

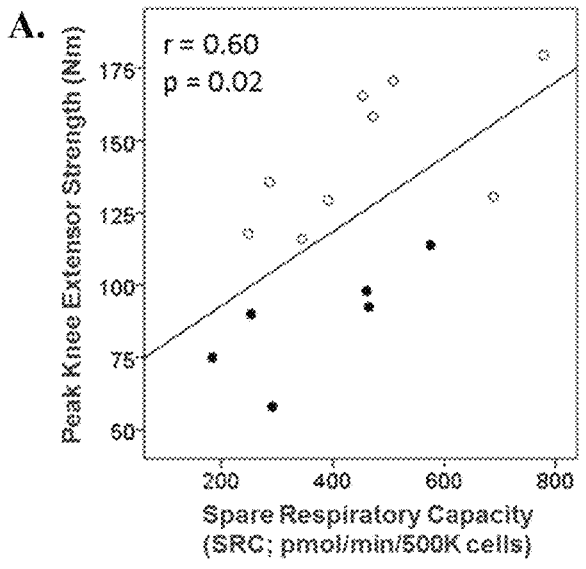
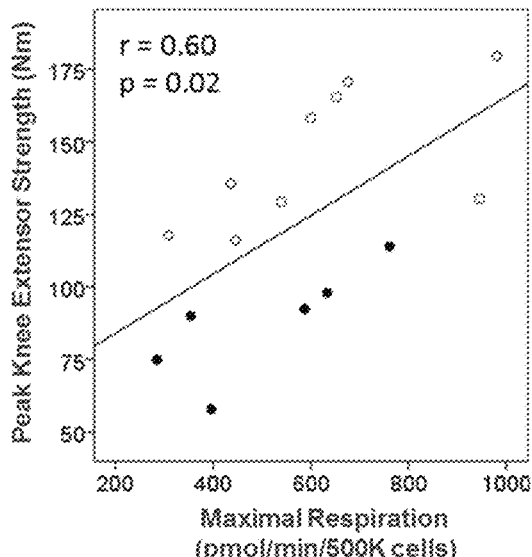
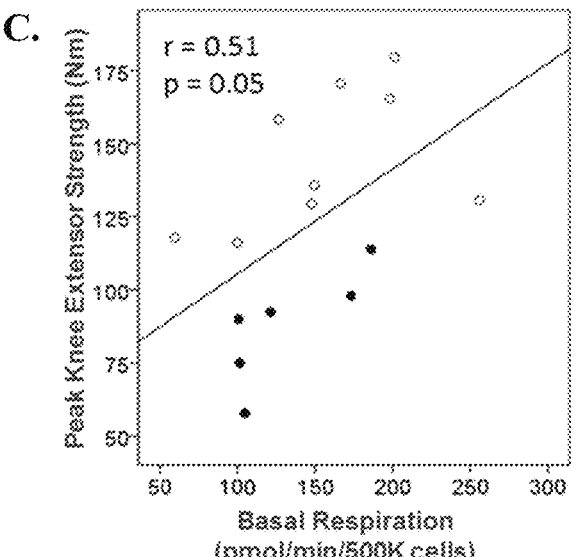
FIG. 7

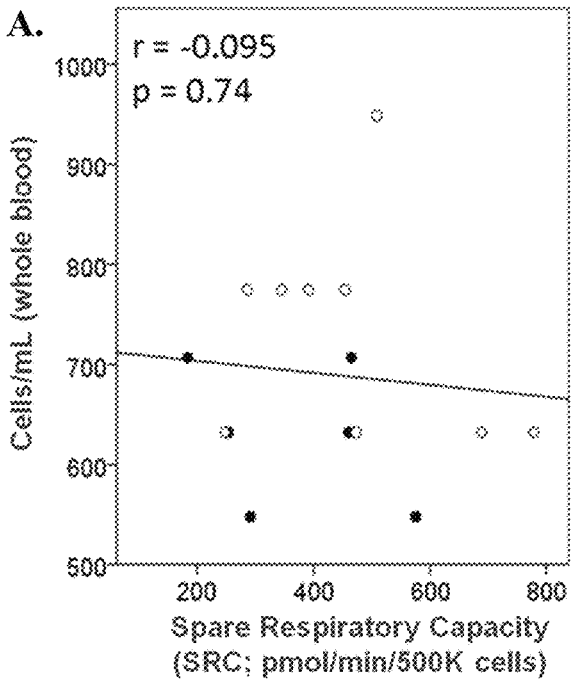
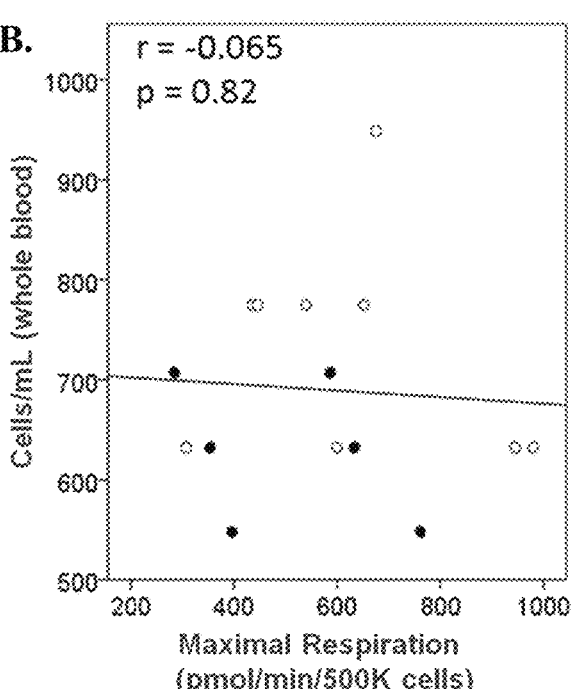
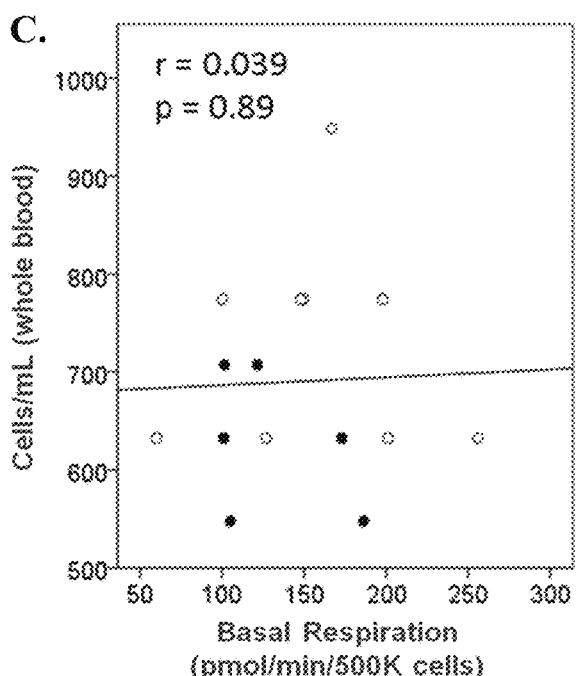
MONOCYTES
FIG. 12

LYMPHOCYTES

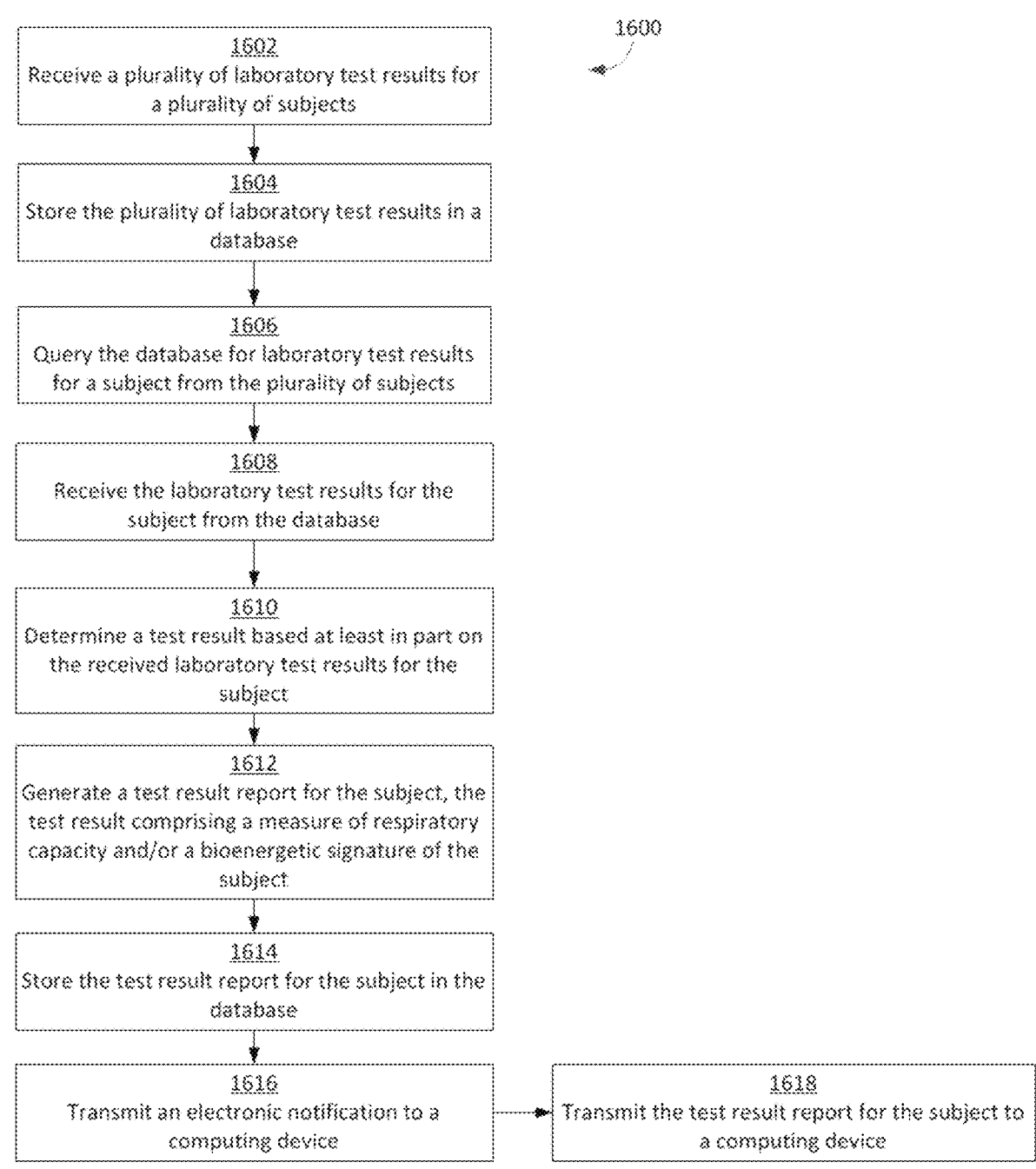

1600

1602
Receive a plurality of laboratory test results for a plurality of subjects

1604
Store the plurality of laboratory test results in a database

1606
Query the database for laboratory test results for a subject from the plurality of subjects

1608
Receive the laboratory test results for the subject from the database

1610
Determine a test result based at least in part on the received laboratory test results for the subject

1612
Generate a test result report for the subject, the test result comprising a measure of respiratory capacity and/or a bioenergetic signature of the subject

1614
Store the test result report for the subject in the database

1616
Transmit an electronic notification to a computing device

1618
Transmit the test result report for the subject to a computing device

FIG. 16

BIOENERGETIC PROFILING OF CIRCULATING BLOOD CELLS AND SYSTEMS, DEVICES, AND METHODS RELATING THERETO

CROSS-REFERENCE TO RELATED APPLICATIONS

The present application is a continuation of U.S. Non-provisional application Ser. No. 15/302,220, filed Oct. 6, 2016, which is a § 371 national stage application of International Application No. PCT/US2015/024795, filed Apr. 7, 2015, which claims the benefit of priority under 35 U.S.C. 119(e) to U.S. Provisional Application Nos. 61/976,417 and 62/075,412, filed Apr. 7, 2014 and Nov. 5, 2014, respectively. Each of the above-referenced applications are hereby incorporated by reference in their entireties herein.

STATEMENT AS TO RIGHTS TO INVENTIONS MADE UNDER FEDERALLY SPONSORED RESEARCH AND DEVELOPMENT

This invention was made with government support under National Institutes of Health (NIH) Grant Nos. 5R01-AG020583 and 3R01-AG020583-09S1 and NIH/National Institute of Aging Grant No. P30-AG21332. The government has certain rights in this invention.

FIELD OF THE DISCLOSURE

The invention relates generally to systems and methods of assessing the bioenergetic profile of a subject, uses thereof, and systems and devices relating thereto.

BACKGROUND

Successful aging cannot be solely defined as the extension of chronological age. Rather, it is clear that biological age is a more significant measure that takes into account the overall health status of an individual at various stages of life. Markers of biological age include, but are not limited to, medical history, physical ability, and cognitive status. The ability to determine biological age in a simple and objective manner would be a breakthrough in geriatric practice. Inclusion of such a test in standard clinical evaluations would allow clinicians to track overall health trajectory of a patient and to monitor the success of strategies designed to promote successful aging.

Bioenergetics refers to the generation and utilization of chemical energy by all living organisms and underlies fundamental cellular processes. As the primary source of cellular energy in the form of ATP, mitochondria are essential regulators of bioenergetics and have been intensively studied as mediators of the aging process. Mutations in mitochondrial DNA (mtDNA), decreased activity of mito-chondrial enzymes, and diminished respiratory capacity have all been associated with advancing age. (Peterson et al., *J. Aging Res.* 2012:194821 (2012).) Each contribute to the overall decline in mitochondrial bioenergetic capacity and can contribute to physical disability. The effects of aging on mitochondria have been studied in various skeletal muscles with a range of oxidative capacities and fiber types; all skeletal muscles assessed exhibited age-related decreases in mtDNA copy number and mRNA expression of electron transport chain genes. (Barazzoni et al., *J. Biol. Chem.* 275(5):3343 (2000); Short et al., *Proc. Natl. Acad. Sci. USA* 102(15):5618 (2005).) Moreover, loss of bioenergetic capacity has been associated with heart disease (Shively et al., *Age (Dordr.)* 34(5):1123 (2012)), neurodegeneration (Nicholls et al., *J. Neurosci. Res.* 85(15)3206 (2007); *Yadava and Nicholls, J. Neurosci.* 27(27):7310 (2007)), muscle loss (Hill et al., *Biochim. Biophys. Acta* 1797(2):285 (2010)), inflammation (van der Windt et al., *Immunity* 36(1):68 (2012)), and metabolic diseases such as diabetes and obesity (Lowell and Shulman, *Science* 307(5708):384 (2005); Rolo and Palmeira, *Toxicol. Appl. Pharmacol.* 212(2):167 (2006)); Woods and Seeley, Nutrition 16(1):894 (2000)). Recent human studies have shown that measures of skeletal muscle fiber mitochondrial bioenergetics (respirometric profile, an index of mitochondrial function) correlate inversely with age and directly with physical ability measured by gait speed and peak aerobic capacity. (Coen et al., *J. Gerontol. A. Biol. Sci. Med. Sci.* 68(4):447-455 (2011); Joseph et al., *Aging Cell* 11(5):801-809 (2012).)

To date, no large-scale clinical trials have included detailed measures of mitochondrial function. Barriers to such studies have included (1) cost—biopsy-based studies require extensive clinical time and effort; (2) technical limitations—isolation of mitochondria or permeabilization of tissues for respirometry requires a high level of expertise; and (3) recruitment—it is difficult to recruit participants to studies requiring elective biopsies. It is with these limitations in mind that the present invention was developed.

SUMMARY

In various aspects, systems and methods of assessing the bioenergetic capacity of a subject are described. In various aspects, systems and methods of assessing wellness of individuals and also assessing treatment options are provided. In particular, the systems and methods are useful for assessing overall wellness in elderly individuals and in individuals with certain diseases.

In one aspect, described are methods of assessing the morbidity or mortality of a subject, the method comprising the steps of measuring the respiratory capacity of cells isolated from a blood sample obtained from a subject, and indicating that the subject has a decreased likelihood of morbidity or death if a relatively high respiratory capacity is measured in the isolated cells compared to a reference population, and that the subject has an increased likelihood of a morbidity or death if a relatively low respiratory capacity is measured in the isolated cells compared to the reference population.

In another aspect, described are methods of identifying a subject of at least 60 years of age with an increased likelihood of morbidity or an increased likelihood of diminished life expectancy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of morbidity or diminished life expectancy if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500, 000 cells, or iii) a SRC of 40% or less of a Max OCR.

In another aspect, described are methods of identifying a subject of at least 60 years of age with a decreased likelihood of morbidity or a decreased likelihood of diminished life expectancy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has a decreased likelihood of morbidity or diminished life expectancy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In another aspect, described are methods of assessing likelihood of a positive clinical outcome for a subject, the method comprising the steps of measuring the respiratory capacity of cells isolated from a blood sample obtained from a subject, and indicating that the subject has an increased likelihood of a positive clinical outcome if a relatively high respiratory capacity measured in the isolated cells compared to a reference population, and that the subject has a decreased likelihood of a positive clinical outcome if a relatively low respiratory capacity measured in the isolated cells compared to the reference population.

In another aspect, described are methods of assessing likelihood of a positive clinical outcome for a subject, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of a positive clinical outcome if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In another aspect, described are methods of assessing likelihood of a negative clinical outcome for a subject, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of a positive clinical outcome if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR.

In another aspect, described are methods of selecting treatment strategy for a subject, the method comprising the steps of measuring the respiratory capacity of cells isolated from a blood sample obtained from a subject, and selecting an aggressive treatment strategy for the subject if a relatively high respiratory capacity measured in the isolated cells compared to a reference population, and selecting a non-aggressive treatment strategy for the subject if a relatively low respiratory capacity measured in the isolated cells compared to the reference population.

In another aspect, described are methods of identifying a subject that is not likely to benefit from an aggressive treatment strategy for a disease, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject is not likely to benefit from an aggressive treatment strategy for a disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR.

In another aspect, described are methods of identifying a subject that is likely to benefit from an aggressive treatment strategy for a disease, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject is likely to benefit from an aggressive treatment strategy for a disease if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In another aspect, described are methods of identifying a subject having experienced a cardiac event or coronary heart disease that has a decreased likelihood of benefiting from rehabilitation therapy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has a decreased likelihood of benefiting from rehabilitation therapy if at least one of the following conditions is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR.

In another aspect, described are methods of identifying a subject having experienced a cardiac event or coronary heart disease that has an increased likelihood of benefiting from rehabilitation therapy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of benefiting from rehabilitation therapy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In another aspect, described are methods of improving the outcome of administering an aggressive treatment to a subject of at least 60 years of age, the method comprising: (a) administering to the subject an improvement therapy comprising at least one of i) an aerobic exercise program, ii) an aerobic exercise program and weight loss diet, and iii) a nutraceutical or dietary supplement; (b) periodically monitoring the respiratory capacity of circulating blood cells obtained from the subject, wherein the respiratory capacity is at least one of the Basal Oxygen Consumption Rate (Basal OCR), the Maximum Oxygen Consumption Rate (Max OCR), or the Spare Respirometric Capacity (SRC) of the cells, and wherein the circulating blood cells are selected from the group consisting of peripheral blood mononuclear cells (PBMCs), lymphocytes, monocytes, platelets, and neutrophils; (c) administering the aggressive treatment to the subject once the subject's respiratory capacity is determined to be at least one of the following: i) a Maximum Oxygen Consumption Rate (Max OCR) of PBMCs is more than about 250 pmol/min/500,000 cells, ii) a Spare Respiratory Capacity (SRC) of PBMCs is more than about 100 pmol/min/500,000 cells, iii) a SRC that is 40% or greater of a Max OCR in PBMCs; or v) an increased Basal OCR, Max OCR, or SRC of at least two-fold in PBMCs, lymphocytes, monocytes, platelets, or neutrophils.

In another aspect, described are methods of treating a subject with a low bioenergetic profile, wherein the method comprise: (a) identifying a subject that has a low bioenergetic profile in circulating blood cells obtained from the subject; and (b) administering an improvement therapy to the subject, wherein the circulating blood cells are peripheral blood mononuclear cells (PBMCs), lymphocytes, monocytes, platelets, or neutrophils, wherein the low bioenergetic profile comprises i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR, and wherein the improvement therapy comprises at least one of i) an aerobic exercise program, ii) an aerobic exercise program and weight loss diet, iii) a nutraceutical or dietary supplement; or iv) a pharmaceutical.

In another aspect, described are methods of treating a subject, the method comprising the steps of (a) measuring the respiratory capacity in cells isolated from a blood sample obtained from the subject, (b) administering an aggressive treatment to the subject if a high respiratory capacity compared to a reference population is measured in the isolated cells.

In another aspect, described are methods of treating a subject, the method comprising the steps of: (a) measuring the respiratory capacity in cells isolated from a blood sample obtained from the subject, and (b) administering a non-aggressive treatment to the subject if a low respiratory capacity compared to a reference population is measured in the isolated cells.

In another aspect, described are methods of identifying early stage Alzheimer's disease in a subject, the method comprising: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject may have early stage Alzheimer's disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR; and the subject does not exhibit cognitive impairment or glycemic dysregulation.

In another aspect, provided are respirometry systems, devices, and components thereof, that include disposable vessels for use in analyzing liquid samples containing non-adherent cells or isolated mitochondria. In one aspect, the respirometry systems, devices, and components are configured to continuously mix, stir, or agitate the liquid sample during analysis. In another aspect, the respirometry systems comprise vessels to contain liquid samples, oxygen sensors, and a delivery system for reagents used to assess respirometry capacity.

In another aspect, described are systems comprising a first computing device, the first computing device in communication with a database; a first application executing on the first computing device, the first application configured to receive a plurality of laboratory test results for a plurality of subjects and store the plurality of laboratory test results in the database, wherein the plurality of laboratory test results comprise a measure of respiratory capacity determined in a blood sample obtained from the subject; a second computing device, the second computing device in communication with the database; and a second application executing on the second computing device, the second application configured to query the database for laboratory test results for a subject from the plurality of subject; receive the laboratory test results for the subject from the database; determine a test result based at least in part on the received laboratory test results for the subject, the test results comprising a measure of respiratory capacity determined in a blood sample obtained from the subject; generate a test result report for the subject, the test result report comprising the systemic respiratory capacity of the subject and based at least in part on the test result for the subject; and transmit the test result report for the patient to a third computing device.

In another aspect, the invention comprises methods comprising receiving a plurality of laboratory test results in a database, wherein the plurality of laboratory test results comprise a measure of respiratory capacity determined in a blood sample obtained from the subject; storing the plurality of laboratory test results in the database; querying the database for laboratory test results for a subject from the plurality of subjects; receiving the laboratory test results for the subject from the database; determining a test result based in part on the received laboratory test results for the subject, the test result comprising the respiratory capacity of the subject and based at least in part on the test result for the subject; generating a test result report for the subject, the test result report comprising the systemic respiratory capacity of the subject and based at least in part on the test result for the subject; and transmitting the test result report for the subject to a computing device.

These illustrative features are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

BRIEF DESCRIPTION OF DRAWINGS

The application includes the following figures. These figures are provided for illustrative purposes and depict certain embodiments of the invention. The figures are not intended to limit the scope of the invention in any way.

FIG. 3 depicts the relationship between bioenergetic capacities in PBMCs and muscle mitochondria subjects, according to certain aspects. Oxygen consumption profiles of PBMCs (500K cells/well) and isolated muscle mitochondria (5 μg/well) are plotted on the x and y axes. For muscle mitochondria, respiratory capacity was measured as the ratio of state 2 respiration to state 3 respiration. For PBMCs, respiratory capacity was measured as the ratio of Basal OCR to Max OCR. Panel A shows the OCR profile determined in five non-human primates (NHP); age of animal subjects indicated next to each data point. Panel B shows the OCR profile for 14 human subjects; ages ranging from 65-79 years.

FIG. 5 depicts the relationship between PBMC respiration and gait speed (400 m walk) in elderly human subjects, according to certain aspects. Gait speed (m/s) is plotted against (A) spare respiratory capacity (SRC) (Max-OCR minus Basal-OCR; picomoles/min/500,000 cells), (B) Max-OCR (picomoles/min/500,000 cells), and (C) basal-OCR (picomoles/min/500,000 cells) measured in PBMCs.

FIG. 7 depicts the relationship between PBMC respiration and peak knee extensor strength according to certain aspects. Knee extensor strength measures (Nm) are plotted against SRC (A), Max-OCR (B), and basal-OCR measured in PBMCs (C). Gender is indicated as black circles denoting female subjects and white circles denoting male subjects.

FIG. 12 depicts the respirometric profiles of monocytes measured as SRC (A), Max-OCR (B), and basal-OCR (C) according to certain aspects. Gender is indicated as black circles denoting female subjects and white circles denoting male subjects.

FIG. 16 depicts a block diagram illustrating an operation of and systems and methods for a laboratory reporting system according to certain aspects.

DETAILED DESCRIPTION

Figure 1:
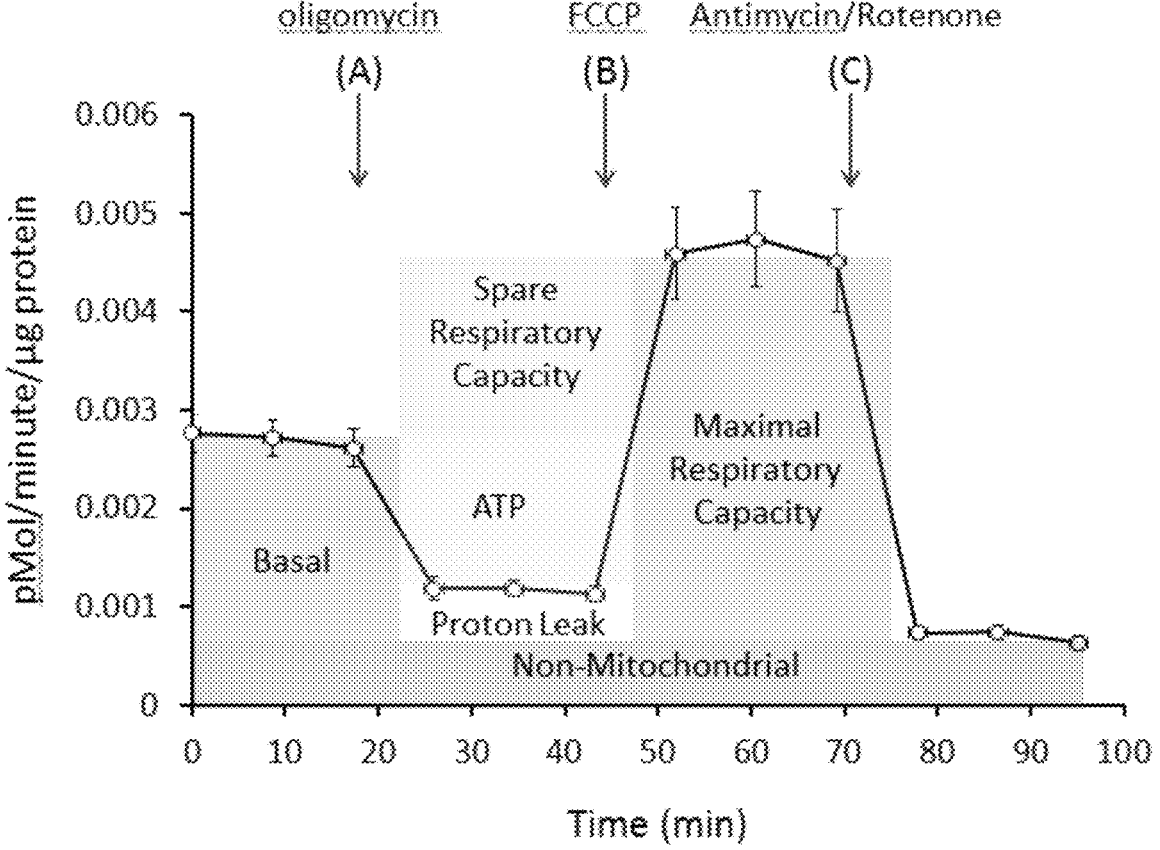
FIG. 1 depicts the bioenergetic profiling of peripheral blood mononuclear cells (PBMCs, or other circulating blood cells, isolated from whole blood) according to some aspects. Basal oxygen consumption rate measurements are made in the presence of glucose and pyruvate acting as fuels. Oligomycin (A) is added to block ATP synthase. The decrease in oxygen consumption reflects the amount of oxygen consumed to fuel the conversion of ADP to ATP. Next, FCCP (B) is added to uncouple mitochondria and induce maximal oxygen consumption. The resultant increase in oxygen consumption represents the maximal metabolic capacity of the cells or tissue. The difference in oxygen consumption under basal conditions and after FCCP addition represents the spare respiratory capacity (SRC). A combination of antimycin and rotenone (C) is added next in order to completely block the electron transport chain (ETC). Any residual respiration is due to non-mitochondrial sources. Subtracting this residual oxygen consumption rate from the rate left after the blockage of ATP synthase by oligomycin, provides a measurement of oxygen consumption that is not linked to ATP synthesis. This is representative of proton leak, a measure of efficiency.

The following description recites various aspects and features of the disclosure. No particular feature or embodiment is intended to define the scope of the invention. Rather, the features and embodiments merely provide non-limiting examples various compositions, apparatuses, and methods that are at least included within the scope of the invention. The description is to be read from the perspective of one of ordinary skill in the art; therefore, information well known to the skilled artisan is not necessarily included.

As used herein, the articles "a," "an," and "the" include plural referents, unless expressly and unequivocally disclaimed.

As used herein, the conjunction "or" does not imply a disjunctive set. Thus, the phrase "A or B is present" includes each of the following scenarios: (a) A is present and B is not present; (b) A is not present and B is present; and (c) A and B are both present. Thus, the term "or" does not imply an either/or situation, unless expressly indicated.

As used herein, the term "comprise," "comprises," or "comprising" implies an open set, such that other elements can be present in addition to those expressly recited.

Unless otherwise indicated, all numbers expressing quantities of ingredients, reaction conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, for example, 1 to 6.1, and ending with a maximum value of 10 or less, for example, 5.5 to 10.

As used herein, the term "bioenergetic capacity" or "respiratory capacity" refers to the overall respirometric profile of cells or isolated mitochondria. Bioenergetic capacity reflects the ability of mitochondria to generate ATP via oxidative phosphorylation. Factors affecting bioenergetic capacity include basal oxygen consumption rate, maximal oxygen consumption rate, and mitochondrial leak. High respiratory capacity is defined by low basal respiration, high maximal respiration, and low leak. Factors contributing to low respiratory capacity include high basal respiration, low maximal respiration, and high leak.

As used herein, the term "oxygen consumption rate" or "OCR" refers to the rate of respiration of cells or isolated mitochondria. Oxygen is consumed by mitochondria in order to generate ATP from ADP via oxidative phosphorylation. The rate at which oxygen is consumed is reflective of mitochondrial function via oxidative phosphorylation. OCR is generally measured as the amount of oxygen (pmol) consumed per minute (reported as a positive integer). The measurement is generally also normalized by number of cells or total amount of cellular protein.

As used herein, the term "spare respiratory capacity" or "SRC" refers to the difference in maximal oxygen consumption rate and baseline oxygen consumption rate. It is reflective of the ability of a cell to increase oxygen consumption rate in response to increased physiological demand for ATP. OCR is generally measured as the amount of oxygen (pmol) consumed per minute (reported as a positive integer). The measurement is generally also normalized by number of cells or total amount of cellular protein.

As used herein, the term "respiratory control ratio" or "RCR" refers to an indicator of mitochondrial function. Increased RCR corresponds to improved mitochondrial health. RCR is the ratio of state 3 respiration to state 4 respiration (or 4o respiration).

As used herein, the term "mitochondrial uncouplers" of oxidative phosphorylation in mitochondria refers to compounds that inhibit the coupling between the electron transport and phosphorylation reactions. Such compounds can be used to measure maximal uncoupled mitochondrial oxygen consumption. An example of such a compound is FCCP.

As used herein, the term "clinical outcome" refers to the response of a patient to a medical intervention.

As used herein, the term "bioenergetic signature" refers to the cumulative information presented by the individual respirometric profiles of various blood cells populations; such as, monocytes, lymphocytes, platelets, and neutrophils.

Methods of Involving Assessment of Respiratory Capacity

In various aspects, the described methods and systems permit assessing wellness of an individual by measuring the bioenergetic capacity, or respiratory capacity, of circulating blood cells. In particular, the methods and systems are useful for assessing overall wellness in elderly individuals or in individuals with certain diseases.

Prior to the work described herein, there was no well-accepted blood biomarker that accurately predicts physical ability, which in turn accurately predicts the overall wellness of a subject. Blood biomarkers are widely sought after as tools for diagnosing disease states and predicting clinical outcomes. The use of blood for clinical diagnosis is attractive because it can be collected repeatedly in a minimally invasive manner. Also, compared to tissue biopsies, blood cells are easily accessible and suitable for multiple samplings over relatively short periods. This makes them appropriate for large-scale clinical trials and as a potential diagnostic tool.

Diagnosis of bioenergetic capacity in patients may have vast implications in personalized healthcare. In some instances, bioenergetic capacity can serve as a powerful risk assessment tool for predicting the outcomes of various treatments. Physicians, geriatricians in particular, are often faced with the decision to prescribe intensive treatment, rehabilitation therapy or palliative care. Clinicians must carefully consider a wide variety of information about an individual patient's status in order to make these decisions. Bioenergetic profiling as described herein can serve as a powerful measurement that integrates a variety of physiological factors that can affect clinical outcomes.

In another aspect, bioenergetic profiling can address a central challenge in geriatric medicine. There is tremendous heterogeneity in people in their seventies and eighties; two older individuals with the same clinical disease burden phenotype can have dramatically different probabilities of recovery. While clinicians can often recognize this based on assessments of physical ability, there are no accepted biological measures to support clinical judgment as to how a patient's frailty status should influence their treatment options. Clinicians, patients, and patients' families would greatly benefit from a diagnostic tool that could help guide discussions about the probability of recovery after an insult (for example, a fall, hip fracture, or chemotherapy) in older adults. Thus, aspects of the invention provide blood-based bioenergetic profiling as an index of frailty and susceptibility to poor recovery or, conversely, as a predictor of excellent recovery.

An aspect of the methods described herein is that measurement of mitochondria function in isolated blood cells serves as an integrated, systemic measure of biological age (e.g., as reflected in physical ability) and bioenergetic capacity. The basis of this is that mitochondria are involved in numerous age related diseases and in the process of aging itself. Without being limited to any particular theory, it is proposed that, because blood cells migrate through the circulatory system and infiltrate various tissues, the metabolic profile of certain blood cell types may be able to reflect the metabolism of the tissues they interact with. Circulating blood cells are exposed to different microenvironments and are uniquely able to sample the metabolic milieu of different tissues, enabling them to report on whole body metabolism. The bioenergetic capacity of various tissues are sensitive to numerous circulating factors, such an inflammatory cytokines, that affect mitochondrial function. Blood cells are exposed to these circulating factors and may report on their effects on mitochondrial function.

This theory is also supported by the fact that there is evidence that certain aspects of mitochondrial bioenergetics at the genetic level are systemic and shared across tissues. In two separate reports, a low-calorie diet decreased expression of genes involved in OXPHOS in peripheral blood mononuclear cells (PBMCs) and in skeletal muscle biopsies. (Crujeiras et al., *OMICS* 12(4):251-261 (2008); Kayo et al., *Proc. Natl Acad. Sci. USA* 98(9):5093-5098 (2001).) Similarly, type-2-diabetes is associated with decreased expression of OXPHOS genes in skeletal muscle and PBMCs. (Patti et al., *Proc. Natl Acad. Sci. USA* 100(14):8466-8471 (2003); Takamura et al., *Biochem. Biophys. Res. Commun.* 361(2):379-384 (2007).) A recent study assessed gene expression in response to a dietary intervention in PBMCs and skeletal muscle biopsies from the same individual. (Rudkowska et al., *OMICS* 15(1-2):1-7 (2011).) After an 8-week polyunsaturated fatty acid-supplemented diet, gene expression changes in PBMCs and muscle were strongly correlated suggesting that both tissues responded similarly to dietary intervention.

In another aspect, systemic measures of bioenergetic capacity also provide a novel research tool for studying its determinants and prognostic importance. Various methods described herein can be used as screening tools for the design and evaluation of interventions, particularly those that target mitochondria.

In one aspect, described are methods of assessing the morbidity or mortality of a subject, the method comprising the steps of measuring the respiratory capacity of cells isolated from a blood sample obtained from a subject, and indicating that the subject has a decreased likelihood of morbidity or death if a relatively high respiratory capacity is measured in the isolated cells compared to a reference population, and that the subject has an increased likelihood of a morbidity or death if a relatively low respiratory capacity is measured in the isolated cells compared to the reference population.

In another aspect, described are methods of identifying a subject of at least 60 years of age with an increased likelihood of morbidity or an increased likelihood of diminished life expectancy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of morbidity or diminished life expectancy if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR.

In another aspect, described are methods of identifying a subject of at least 60 years of age with a decreased likelihood of morbidity or a decreased likelihood of diminished life expectancy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has a decreased likelihood of morbidity or diminished life expectancy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In some instances, the above-described methods may be useful for subjects that exhibit one or more risk factors for or clinical signs of morbidity. In some examples, morbidity may comprise at least one of increased frailty or cognitive impairment. In another example, the subject may have risk factors for or have exhibited clinical signs of a cardiac event or coronary heart disease. In some instances, the subject may exhibit one or more of impaired cognitive function; impaired ability to walk; nicotine use (such as within 1 year); drug abuse; alcohol abuse; insulin dependence or uncontrolled diabetes (Fast Blood Sugar >140 mg/dL), uncontrolled hypertension (BP>180/100 mmHg); abnormal kidney function; abnormal liver blood tests; heart disease; past or current cardiovascular disease; past or current respiratory disease; past or current clinical diagnoses of neurological or hematological disease; cancer treatment within two preceding year (excluding non-melanoma skin cancer); or clinically evident edema or anemia. For example, heart disease may comprise a conduction disorder, uncontrolled arrhythmia, or new echocardiogram Q waves or ST-segment depressions (>2 mm). In another example, cardiovascular disease may comprise uncontrolled angina or dysrhythmia, hypertrophic cardiomyopathy, congestive heart failure, peripheral artery disease, stroke, history of myocardial infarction, use of defibrillator or major heart surgery, deep vein thrombosis, or pulmonary embolus.

In another example, the subject may be a subject who has cancer. Tumor cells are known to exhibit a glycolytic shift referred to as the Warburg effect in which most cancer cells predominantly produce energy by a high rate of glycolysis followed by lactic acid fermentation in the cytosol, rather than by a comparatively low rate of glycolysis followed by oxidation of pyruvate in mitochondria as in most normal cells. The latter process is aerobic (uses oxygen). Malignant, rapidly growing tumor cells typically have glycolytic rates up to 200 times higher than those of their normal tissues of origin, even if oxygen is plentiful. Without being bound to any specific theory, it is proposed that, because blood cells migrate through the circulatory system and infiltrate various tissues, the metabolic profile of certain blood cell types may be able to reflect the metabolism of cancer cells with which they interact. In addition, the bioenergetic capacity of various tissues and tumors are sensitive to numerous circulating factors, such an inflammatory cytokines, that affect mitochondrial function. Blood cells are exposed to these circulating factors and may report on their effects on mitochondrial function. In some instances, the subject may have a cancer such as a carcinoma, a lymphoma, a blastoma, a sarcoma, or leukemia. More particular examples of such cancers include squamous cell cancer, lung cancer (such as small-cell lung cancer, non-small cell lung cancer); gastro-intestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer.

In another aspect, described are methods of assessing likelihood of a positive clinical outcome for a subject, the method comprising the steps of measuring the respiratory capacity of cells isolated from a blood sample obtained from a subject, and indicating that the subject has an increased likelihood of a positive clinical outcome if a relatively high respiratory capacity measured in the isolated cells compared to a reference population, and that the subject has a decreased likelihood of a positive clinical outcome if a relatively low respiratory capacity measured in the isolated cells compared to the reference population.

In another aspect, described are methods of assessing likelihood of a positive clinical outcome for a subject, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of a positive clinical outcome if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In another aspect, described are methods of assessing likelihood of a negative clinical outcome for a subject, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of a positive clinical outcome if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR.

In some instances, the positive clinical outcome may be at least one of responsiveness to treatment with nutraceuticals, dietary supplements, or pharmaceuticals; benefit from a program of diet and exercise; responsiveness to physical rehabilitation; responsiveness to chemotherapy treatment; improved recovery in cardiac rehabilitation or intensive care hospitalization treatment; or improved recovery following surgery. In some instances, the negative clinical outcome may be at least one of lack of responsiveness to treatment with nutraceuticals, dietary supplements, or pharmaceuticals; lack of benefit from a program of diet and exercise; lack of responsiveness to physical rehabilitation; lack of responsiveness to chemotherapy treatment; poor recovery in cardiac rehabilitation or intensive care hospitalization treatment; or poor recovery following surgery. In some instances, nutraceuticals or dietary supplements may comprise compounds or foods selected to improve mitochondrial function. For example, in some cases, nutraceuticals or dietary supplements may comprise at least one of Vitamin D, B vitamins, CoQ10, Carnitine, Lipoic Acid, Vitamin C, and Vitamin K, amongst others.

In another aspect, the invention provides methods of selecting treatment strategy for a subject, the method comprising the steps of measuring the respiratory capacity of cells isolated from a blood sample obtained from a subject, and selecting an aggressive treatment strategy for the subject if a relatively high respiratory capacity measured in the isolated cells compared to a reference population, and selecting a non-aggressive treatment strategy for the subject if a relatively low respiratory capacity measured in the isolated cells compared to the reference population. In some embodiments, an aggressive treatment strategy may be surgery, drug, nutraceutical, or dietary supplement administration, physical rehabilitation, or change in diet or exercise regimen. In some embodiments, a non-aggressive treatment strategy comprises patient monitoring or palliative care.

In another aspect, described are methods of identifying a subject that is not likely to benefit from an aggressive treatment strategy for a disease, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject is not likely to respond to/benefit from an aggressive treatment strategy for a disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In another aspect, described are methods of identifying a subject that is likely to benefit from an aggressive treatment strategy for a disease, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject is likely to benefit from an aggressive treatment strategy for a disease if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In another aspect, described are methods of identifying a subject having experienced a cardiac event or coronary heart disease that has a decreased likelihood of benefiting from rehabilitation therapy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has a decreased likelihood of benefiting from rehabilitation therapy if at least one of the following conditions is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In another aspect, described are methods of identifying a subject having experienced a cardiac event or coronary heart disease that has an increased likelihood of benefiting from rehabilitation therapy, the method comprising the steps of: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject has an increased likelihood of benefiting from rehabilitation therapy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the rehabilitation therapy may further comprise a weight loss diet.

In another aspect, described are methods of improving the outcome of administering an aggressive treatment to a subject of at least 60 years of age, the method comprising: (a) administering to the subject an improvement therapy comprising at least one of i) an aerobic exercise program, ii) an aerobic exercise program and weight loss diet, and iii) a nutraceutical or dietary supplement; (b) periodically monitoring the respiratory capacity of circulating blood cells obtained from the subject, wherein the respiratory capacity is at least one of the Basal Oxygen Consumption Rate (Basal OCR), the Maximum Oxygen Consumption Rate (Max OCR), or the Spare Respirometric Capacity (SRC) of the cells, and wherein the circulating blood cells are selected from the group consisting of peripheral blood mononuclear cells (PBMCs), lymphocytes, monocytes, platelets, and neutrophils; (c) administering the aggressive treatment to the subject once the subject's respiratory capacity is determined to be at least one of the following: i) a Maximum Oxygen Consumption Rate (Max OCR) of PBMCs is more than about 250 pmol/min/500,000 cells, ii) a Spare Respiratory Capacity (SRC) of PBMCs is more than about 100 pmol/min/500,000 cells, iii) a SRC that is 40% or greater of a Max OCR in PBMCs; or v) an increased Basal OCR, Max OCR, or SRC of at least two-fold in PBMCs, lymphocytes, monocytes, platelets, or neutrophils. In some instances, aggressive treatment may comprise surgery, chemotherapy, radiation, a cardiac rehabilitation program, or intensive care hospitalization treatment.

In another aspect, described are methods of treating a subject with a low bioenergetic profile, wherein the method comprise: (a) identifying a subject that has a low bioenergetic profile in circulating blood cells obtained from the subject; and (b) administering an improvement therapy to the subject, wherein the circulating blood cells are peripheral blood mononuclear cells (PBMCs), lymphocytes, monocytes, platelets, or neutrophils, wherein the low bioenergetic profile comprises i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR, and wherein the improvement therapy comprises at least one of i) an aerobic exercise program, ii) an aerobic exercise program and weight loss diet, iii) a nutraceutical or dietary supplement; or iv) a pharmaceutical. In some instances, the improvement therapy may be administered for at least two weeks. In some cases, the improvement therapy may include at least one of i) an aerobic exercise program, ii) an aerobic exercise program and weight loss diet, and iii) a nutraceutical or dietary supplement.

In another aspect, described are methods of treating a subject, the method comprising the steps of (a) measuring the respiratory capacity in cells isolated from a blood sample obtained from the subject, (b) administering an aggressive treatment to the subject if a high respiratory capacity compared to a reference population is measured in the isolated cells.

In another aspect, described are methods of treating a subject, the method comprising the steps of: (a) measuring the respiratory capacity in cells isolated from a blood sample obtained from the subject, and (b) administering a non-aggressive treatment to the subject if a low respiratory capacity compared to a reference population is measured in the isolated cells.

In another aspect, described are methods of identifying early stage Alzheimer's disease in a subject, the method comprising: (a) providing a blood sample obtained from the subject; (b) isolating circulating blood cells from the blood sample; (c) distributing the circulating blood cells into an analytical vessel; (d) measuring the respiratory capacity of the circulating blood cells; (e) identifying that the subject may have early stage Alzheimer's disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR; and the subject does not exhibit cognitive impairment or glycemic dysregulation. Cognitive impairment may be determined using clinically recognized factors such as the well-established Mild Cognitive Impairment (MCI) criteria and the Mini-Mental State Exam (MMSE). For example, glycemic dysregulation may be characterized by a high level of hemoglobin A1c and a high fasting glucose level. Mild dysregulation may be reflected by a hemoglobulin A1c level of greater than 5.6% of total hemoglobulin and a fasting glucose level greater than 99 mg/dL.

In some instances, the methods of the invention are appropriate for use with samples obtained from a human subject or a non-human primate subject. In some cases, the subject may be a non-primate animal such as, for example, a domestic animal. In some instances, the subject may be a cow, horse, dog, cat, pig, mouse, rat, guinea pig, monkey, or bird. In certain embodiments, the methods are appropriate for use with samples obtained from aged subjects or subjects who are exhibiting a disease state. For example, in some embodiments, the subject is human having an age of at least 35 years, at least 40 years, at least 45 years, at least 50 years, at least 55 years, at least 60 years, at least 65 years, at least 70 years, at least 75 years, at least 80 years, at least 85 years, or at least 90 years. In some embodiments, the human subject may also have an age of less than 50 years. In some instances, the human subject is at least 60 years of age. In instances where the subject is not a human, age ranges scaled to those set forth above based on the aging rate of the subject animal are applicable. In some embodiments, the reference population is a population of subjects in the same age group as the subject or having one or more of the same clinical factors as the subject. In some instances, the subject may exhibit one or more risk factors for or clinical signs of morbidity. In some examples, morbidity may comprise at least one of increased frailty or cognitive impairment. In another example, the subject may have risk factors for or have exhibited clinical signs of a cardiac event or coronary heart disease. In some instances, the subject may exhibit one or more of impaired cognitive function; impaired ability to walk; nicotine use (such as within 1 year); drug abuse; alcohol abuse; insulin dependence or uncontrolled diabetes (Fast Blood Sugar >140 mg/dL), uncontrolled hypertension (BP>180/100 mmHg); abnormal kidney function; abnormal liver blood tests; heart disease; past or current cardiovascular disease; past or current respiratory disease; past or current clinical diagnoses of neurological or hematological disease; cancer treatment within two preceding year (excluding non-melanoma skin cancer); or clinically evident edema or anemia. For example, heart disease may comprise a conduction disorder, uncontrolled arrhythmia, or new echocardiogram Q waves or ST-segment depressions (>2 mm). In another example, cardiovascular disease may comprise uncontrolled angina or dysrhythmia, hypertrophic cardiomyopathy, congestive heart failure, peripheral artery disease, stroke, history of myocardial infarction, use of defibrillator or major heart surgery, deep vein thrombosis, or pulmonary embolus. In some instances, the subject may have a cancer such as a carcinoma, a lymphoma, a blastoma, a sarcoma, or leukemia. More particular examples of such cancers include squamous cell cancer, lung cancer (such as small-cell lung cancer, non-small cell lung cancer); gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, prostate cancer, vulval cancer, thyroid cancer, hepatic carcinoma and various types of head and neck cancer. In some instances, the subject exhibits a physical impairment associated with aging or morbidity as described above such that the subject has some extent of physical dehabilitation.

In some embodiments, the isolated circulating blood cells assessed in the various methods of the invention may be isolated peripheral blood mononuclear cells (PBMCs). In certain embodiments, the isolated circulating blood cells may be isolated monocytes, isolated lymphocytes, isolated neutrophils, or isolated platelets. Lymphocytes represent a long-lived population of cells that may report on the cumulative effects of aging on bioenergetics. Alterations in mitochondrial DNA (mtDNA) copy number and mutations/deletions over time would likely affect the respirometric profile of these cells. Monocytes on the other hand are a shorter lived population of cells. These cells may reflect acute bioenergetic changes, particularly those associated with inflammation. For example, alterations in monocyte function have been recently associated with aging. (Hearps, et al., Aging *Cell* (5):867 (2012).) Platelets, which lack a nucleus but harbor mitochondria, may report on systemic bioenergetic capacity without additional signals from the nucleus. There is increasing evidence that inflammation and immune response are involved in the development of frailty in older adults. For example, higher monocyte counts are associated with frailty in certain older individuals. (Leng, et al., *Exp. Gerontol.* (8):511 (2009).) Also, interventions that improve physical ability have also shown an effect on the total number of circulating monocytes and lymphocytes and gene expression in leukocytes. (Radom-Aizik, et al., *Pediatr. Res.* (4):447 (2009).)

In some embodiments, the respiratory capacity of a subject comprises a bioenergetic signature, wherein the bioenergetic signature comprises individual respirometric profiles of various blood cells populations; such as, monocytes, lymphocytes, platelets, and neutrophils. For example, the respiratory capacity may be determined in one or more of monocytes, lymphocytes, platelets, or neutrophils isolated from a blood sample from the subject. In some embodiments, different bioenergetic signatures reflect different states of wellness. For example, different bioenergetic signatures may reflect different responses to different forms of treatment or different clinical outcomes.

Figure 2:
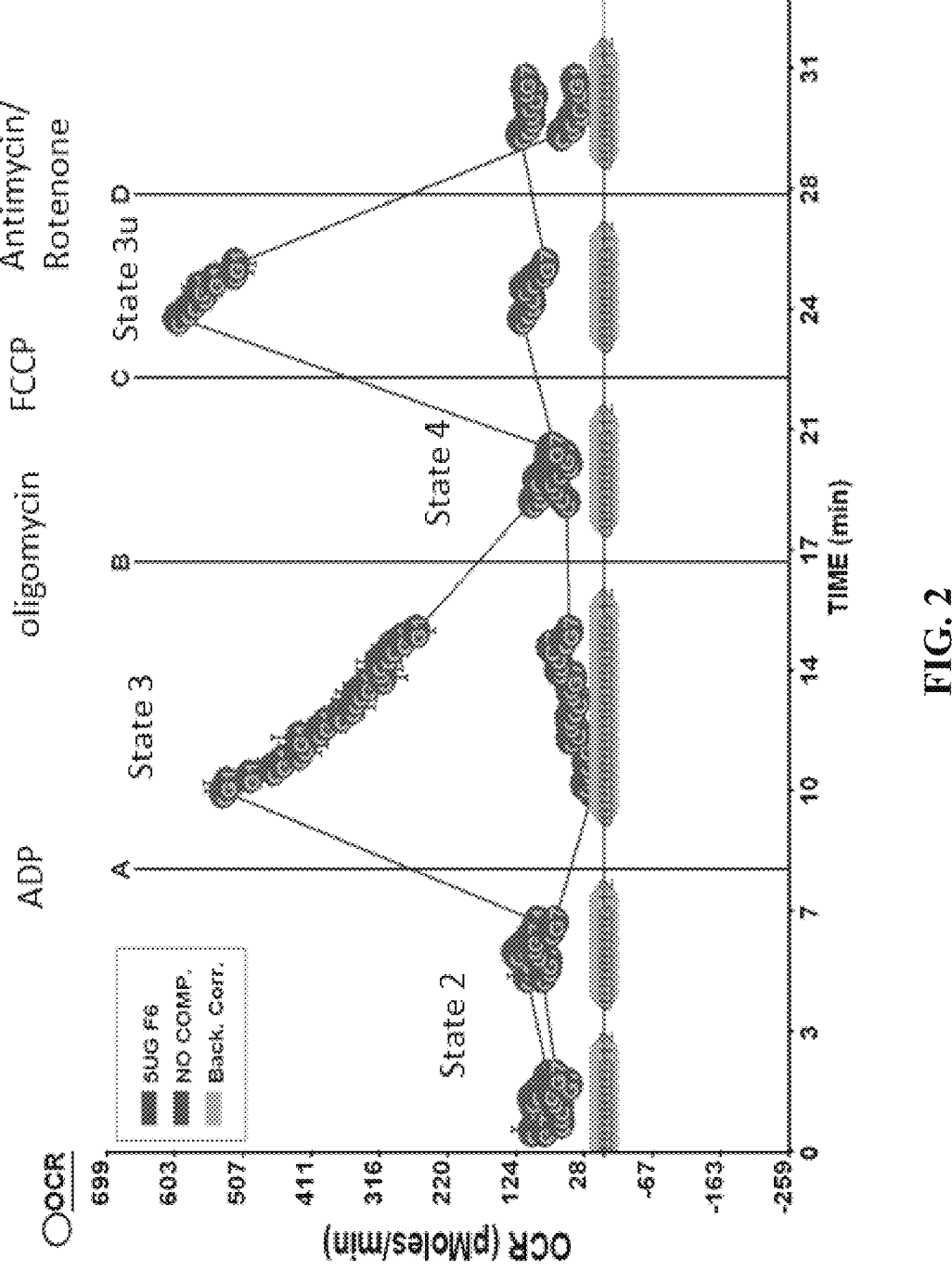
FIG. 2 depicts the bioenergetic profiling of mitochondria isolated from skeletal muscle tissue according to some aspects. State 2 basal mitochondrial respiration is measured in the presence of succinate as fuel and measures any baseline oxygen consumption that may occur in the absence of substrate (ADP). State 3, maximal respiration, is induced by addition of a saturating amount of ADP. State 4o, residual respiration, is measured upon blockage of ATP synthase with oligomycin. Maximal uncoupled respiration (state 3u) is measured with addition of the chemical uncoupler FCCP. Lastly, any non-mitochondrial oxygen consumption in the preparation is measured by blocking electron transport chain activity with a combination of antimycin A and rotenone. This process is described by Rogers et al., *PLos One* 6(7):e21746 (2011).

In some embodiments, mitochondrial function is measured in isolated organelles (mitochondria) or whole cells. There are numerous methods for measuring mitochondrial function in isolated organelles and whole cells. (Brand and Nicholls, *Biochem. J.* 435(2):297-312 (2011).) For example, in some embodiments, respiratory control is measured to reflect mitochondrial function in isolated mitochondria and is reported by the increase in oxygen consumption after addition of ADP as shown in FIG. 2. Respiratory control is most often reported as a ratio, respiratory control ratio (RCR), of maximal capacity and respiration in the absence of substrate or upon inhibition of ATP synthesis. Also, for example, in some embodiments, analogous measures of respiratory control in intact cells (e.g., blood cells such as PBMCs) use mitochondrial uncouplers because ADP cannot readily cross the cell membrane. In some aspects, as shown in FIG. 1, respiratory control in intact cells is measured as maximal oxygen consumption rate (Max-OCR) and spare respiratory capacity (SRC).

In some instances, the respiratory capacity is measured by measuring oxygen consumption rate of the isolated cells. For example, the oxygen consumption rate may be measured by determining maximal oxygen consumption rate (Max OCR). In some embodiments, the oxygen consumption rate is measured by determining spare respiratory capacity (SRC) or respiratory control ratio (RCR). In certain embodiments, SRC is determined for PBMCs as the difference between Max OCR and the Basal OCR. In certain embodiments, RCR is determined for isolated mitochondria as calculated as the ratio of state 3 respiration to state 4o respiration (state 3 respiration/state 4o respiration ratio).

In some instances, measuring the respiratory capacity of the isolated circulating blood cells in any of the above-described methods may comprise (i) measuring a first rate of oxygen disappearance from the medium to determine the Basal OCR; (ii) adding an ATP synthase inhibitor to the medium; (iii) adding a mitochondrial uncoupler to the medium; (iv) measuring a second rate of oxygen disappearance from the medium to determine the Max OCR; and (v) calculating the SRC as the difference between the Max OCR and the Basal OCR. In some instances, measuring respiratory capacity of the isolated circulating blood cells may further comprise adding a mitochondrial Complex I inhibitor and a mitochondrial Complex II inhibitor after measuring a second rate of oxygen disappearance from the medium, measuring a third rate of oxygen disappearance from the medium to determine a non-mitochondrial oxygen consumption (Non-Mito OCR), and subtracting the Non-Mito OCR from the Basal OCR and the Max OCR before calculating the SRC. In one example, the mitochondrial uncoupler may be carbonyl cyanide-4-(trifluoromethoxy)phenylhydrazone (FCCP). In another example, the ATP synthase inhibitor may be oligomycin. In another example, the mitochondrial Complex I inhibitor may be rotenone. In another example, the mitochondrial Complex II inhibitor may be antimycin.

In some instances, the Max OCR level and the SRC level identified in the methods described above may provide useful clinical information at lower levels. For example, in some cases, it is possible to indicate that the subject has or does not have an increased likelihood of morbidity or an increased likelihood of diminished life expectancy, has or does not have an increased likelihood of a positive clinical outcome or a negative clinical outcome, is or is not likely to benefit from an aggressive treatment strategy for a disease, has or does not have an increased likelihood of benefiting from rehabilitation therapy for a cardiac event or coronary heart disease, or has early stage Alzheimer's disease based on whether the respiratory capacity of the isolated circulating cells is above or below a lower Max OCR level or SRC level. Similarly, in some instances, it is possible to improve the outcome of administering an aggressive treatment to a subject of at least 60 years of age by increasing the respiratory capacity of the isolated circulating cells. Also, in some instances, it is possible to improve the bioenergetic capacity of an individual by increasing the respiratory capacity of the isolated circulating cells to lower levels Max OCR or SRC than described above. In some instances, the Basal OCR, the Max OCR, and the SRC levels may be lower in view of the reference population. For example, the levels may be lower when individuals having various morbidities or disease states are accounted for in comparison to individuals without such morbidities. Exemplary morbidities that may impact the clinically useful Max OCR or SRC levels include impaired ability to walk; nicotine use (such as within 1 year); drug abuse; alcohol abuse; insulin dependence or uncontrolled diabetes (such as Fast Blood Sugar >140 mg/dL), uncontrolled hypertension (such as BP>180/100 mmHg); abnormal kidney function; abnormal liver blood tests; heart disease; past or current cardiovascular disease; past or current respiratory disease; past or current clinical diagnoses of neurological or hematological disease; cancer treatment within two preceding year (excluding non-melanoma skin cancer); or clinically evident edema or anemia.

In some instances, the clinically useful Basal OCR is about 150 pmol/min/500,000 cells; about 145 pmol/min/500,000 cells; about 140 pmol/min/500,000 cells; about 135 pmol/min/500,000 cells; about 130 pmol/min/500,000 cells; about 125 pmol/min/500,000 cells; about 130 pmol/min/500,000 cells; about 125 pmol/min/500,000 cells; about 120 pmol/min/500,000 cells; about 115 pmol/min/500,000 cells; about 110 pmol/min/500,000 cells; about 100 pmol/min/500,000 cells; about 95 pmol/min/500,000 cells; about 90 pmol/min/500,000 cells; about 85 pmol/min/500,000 cells; about 80 pmol/min/500,000 cells; about 75 pmol/min/500,000 cells; about 70 pmol/min/500,000 cells; about 65 pmol/min/500,000 cells; about 60 pmol/min/500,000 cells; about 55 pmol/min/500,000 cells; about 50 pmol/min/500,000 cells; about 45 pmol/min/500,000 cells; about 40 pmol/min/500,000 cells; about 35 pmol/min/500,000 cells; about 30 pmol/min/500,000 cells; about 25 pmol/min/500,000 cells; or about 20 pmol/min/500,000 cells.

In some instances, the clinically useful Max OCR is about 250 pmol/min/500,000 cells; about 245 pmol/min/500,000 cells; about 240 pmol/min/500,000 cells; about 235 pmol/min/500,000 cells; about 230 pmol/min/500,000 cells; about 225 pmol/min/500,000 cells; about 220 pmol/min/500,000 cells; about 215 pmol/min/500,000 cells; about 210 pmol/min/500,000 cells; about 205 pmol/min/500,000 cells; about 200 pmol/min/500,000 cells; about 195 pmol/min/500,000 cells; about 190 pmol/min/500,000 cells; about 185 pmol/min/500,000 cells; about 180 pmol/min/500,000 cells; about 175 pmol/min/500,000 cells; about 170 pmol/min/500,000 cells; about 165 pmol/min/500,000 cells; about 160 pmol/min/500,000 cells; about 155 pmol/min/500,000 cells; about 150 pmol/min/500,000 cells; about 145 pmol/min/500,000 cells; about 140 pmol/min/500,000 cells; about 135 pmol/min/500,000 cells; about 130 pmol/min/500,000 cells; about 125 pmol/min/500,000 cells; about 130 pmol/min/500,000 cells; about 125 pmol/min/500,000 cells; about 120 pmol/min/500,000 cells; about 115 pmol/min/500,000 cells; about 110 pmol/min/500,000 cells; about 100 pmol/min/500,000 cells; about 95 pmol/min/500,000 cells; about 90 pmol/min/500,000 cells; about 85 pmol/min/500,000 cells; about 80 pmol/min/500,000 cells; about 75 pmol/min/500,000 cells; about 70 pmol/min/500,000 cells; about 65 pmol/min/500,000 cells; about 60 pmol/min/500,000 cells; about 55 pmol/min/500,000 cells; about 50 pmol/min/500,000 cells; about 45 pmol/min/500,000 cells; about 40 pmol/min/500,000 cells; about 35 pmol/min/500,000 cells; about 30 pmol/min/500,000 cells; about 25 pmol/min/500,000 cells; or about 20 pmol/min/500,000 cells.

In some instances, the clinically useful SRC is about 100 pmol/min/500,000 cells; about 95 pmol/min/500,000 cells; about 90 pmol/min/500,000 cells; about 85 pmol/min/500,000 cells; about 80 pmol/min/500,000 cells; about 75 pmol/min/500,000 cells; about 70 pmol/min/500,000 cells; about 65 pmol/min/500,000 cells; about 60 pmol/min/500,000 cells; about 55 pmol/min/500,000 cells; about 50 pmol/min/500,000 cells; about 45 pmol/min/500,000 cells; about 40 pmol/min/500,000 cells; about 35 pmol/min/500,000 cells; about 30 pmol/min/500,000 cells; about 25 pmol/min/500,000 cells; or about 20 pmol/min/500,000 cells.

In some instances, an SRC of about 40% of Max OCR; about 35% of Max OCR; about 30% of Max OCR; about 25% of Max OCR; about 20% of Max OCR; about 15% of Max OCR; about 10% of Max OCR; or about 5% of Max OCR is clinically useful.

In one example, the isolated circulating blood cells are PBMCs and the clinically useful levels are about 150 pmol/min/500,000 cells for Basal OCR, about 250 pmol/min/500,000 cells for Max OCR, about 100 pmol/min/500,000 cells for SRC, or an SRC of about 40% of Max OCR.

The methods described above can be performed in a variety ways. In some instances, circulating cells, such as PBMCs, lymphocytes, monocytes, platelets, or neutrophils, can be isolated from a blood sample obtained from a subject. The isolated cells are generally placed into culture medium containing various components to maintain the cells ex vivo including, for example, mitochondrial fuels. Exemplary mitochondrial fuels for cells include glucose and pyruvate. In some instances, the cells may be processed so as to isolate the mitochondria therefrom. In such instances, isolated mitochondria are generally placed into culture media or buffer containing components such as, for example, mitochondrial fuels, to maintain the mitochondria ex vivo until analyzed. An exemplary mitochondrial fuel for isolated mitochondria is succinate. In some instances, it may be preferred to measure the respiratory capacity of intact isolated circulating cells when performing the above-described methods because this would provide information about respiration capacity based on both mitochondrial function and number of mitochondria present. In contrast, measuring respiratory capacity of isolated mitochondria may only provide information based on mitochondrial function.

In some instances, mitochondrial function measured in isolated myocyte mitochondria is reflected in mitochondrial function measured in isolated circulating mononuclear cells (PBMCs), as shown in FIG. 3. This relationship exists in non-human primates, as shown in FIG. 3A, and in human subjects, as shown in FIG. 3B.

Figure 4:
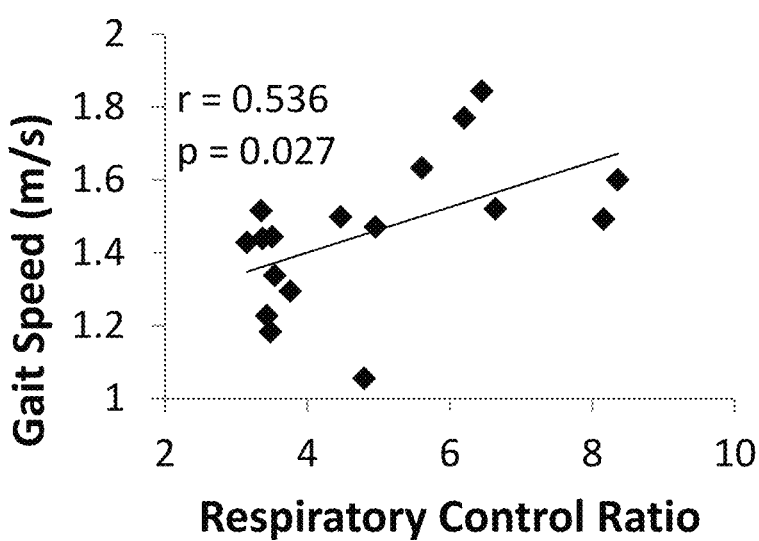
FIG. 4 depicts the relationship between skeletal muscle respiration and gait speed (400 m walk) in elderly human subjects, according to certain aspects. Gait speed (m/s) is plotted against respiratory control ratio (RCR), as measured by state 3 respiration/state 4o respiration of skeletal muscle mitochondria.

In some instances, mitochondrial function measured from myocyte mitochondria and circulating mononuclear cells is associated with gait speed in community-dwelling older adults. For example, individual differences in gait speed correlate directly with RCR of mitochondria isolated from skeletal muscle as shown in FIG. 4, and with both SRC and maximal respiration (Max-OCR) of PBMCs in an elderly adult population of adults, as described in Example 4 and shown in FIG. 5A and FIG. 5B, respectively. Thus, in certain instances, the methods described herein can predict differences in walking speed in older adults and, thus, provide a indicia of overall wellness. In recent years, walking speed and measures of physical function have emerged as the most powerful predictors of mortality and morbidity in older adults. (Guralnik and Winograd, Aging (Milano) 6(5): 303

(1994); Hardy, et al., *J Gen. Intern. Med.* 26(2):130 (2011); Hardy, et al., *J Am. Geriatr. Soc.* 55(11):1727 (2007).) Numerous studies have shown walking speed to be predictive of institutionalization and hospitalization, hospital length of stay, mortality after hospital discharge, and fall risk. (Corsonello, et al., *Rejuvenation. Res.* 15(1):41 (2012); Guralnik and Winograd, Aging (Milano) 6(5):303 (1994); Ostir, et al., *Arch. Intern. Med.* 172(4):353 (2012); Penninx, et al., *J. Gerontol. A Biol. Sci. Med. Sci.* 55(11):M691-M697 (2000); Studenski, *J Nutr. Health Aging* 13(8):733 (2009); Volpato, et al., *J Gerontol. A Biol. Sci. Med. Sci.* 63(12):1393 (2008); Volpato, et al., *J. Gerontol. A Biol. Sci. Med. Sci.* 66(1):89 (2011).) A seminal study has shown that an increase of 0.1 m/s in walk speed was associated with a 0.88 survival hazard. (Studenski, et al., *JAMA* 305(1):50 (2011).) In clinical practice, the methods of the invention represent a vast improvement over measures of walk speed because they can be performed on any individual, regardless of physical status, in a completely objective manner.

Figure 6:
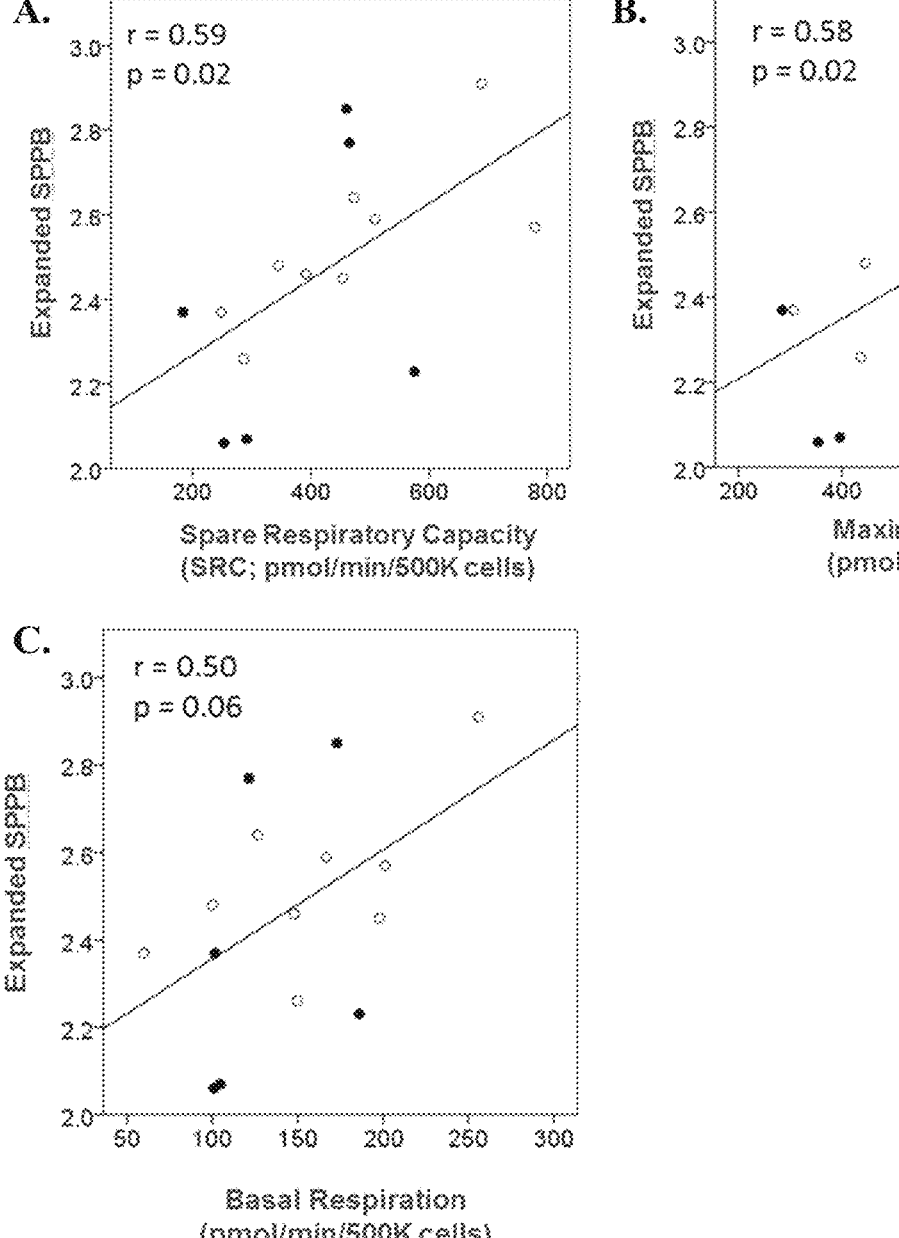
FIG. 6 depicts the relationship between PBMC respiration and composite physical ability according to certain aspects. Expanded short physical performance battery (Ex-SPPB) measures are plotted against SRC (A), Max-OCR (B), and basal-OCR measured in PBMCs (C). Gender is indicated as black circles denoting female subjects and white circles denoting male subjects.
Figure 8:
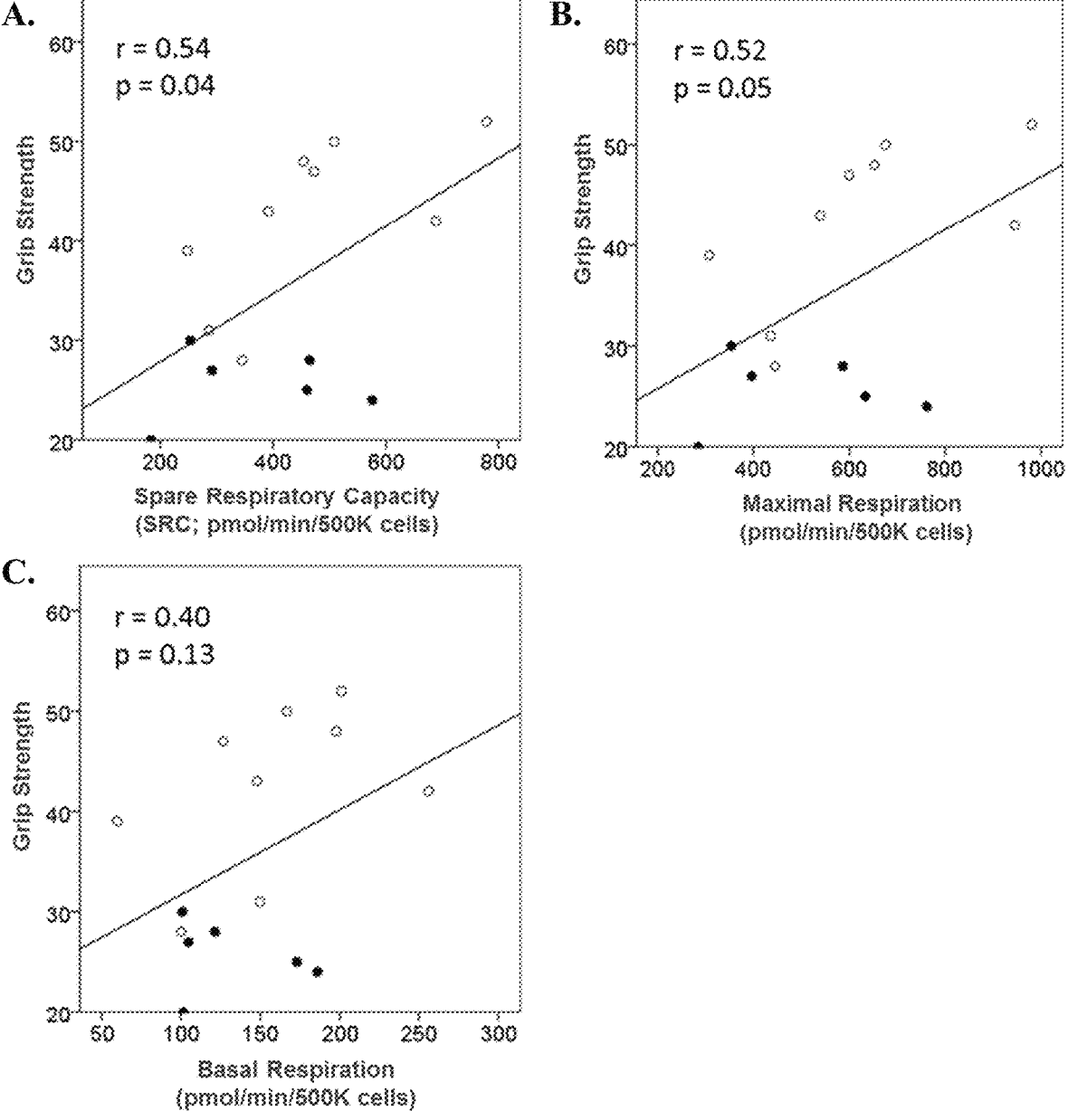
FIG. 8 depicts the relationship between PBMC respiration and grip strength according to certain aspects. Grip strength measures (kg) are plotted against SRC (A), Max-OCR (B), and basal-OCR measured in PBMCs (C). Gender is indicated as black circles denoting female subjects and white circles denoting male subjects.
Figure 9:
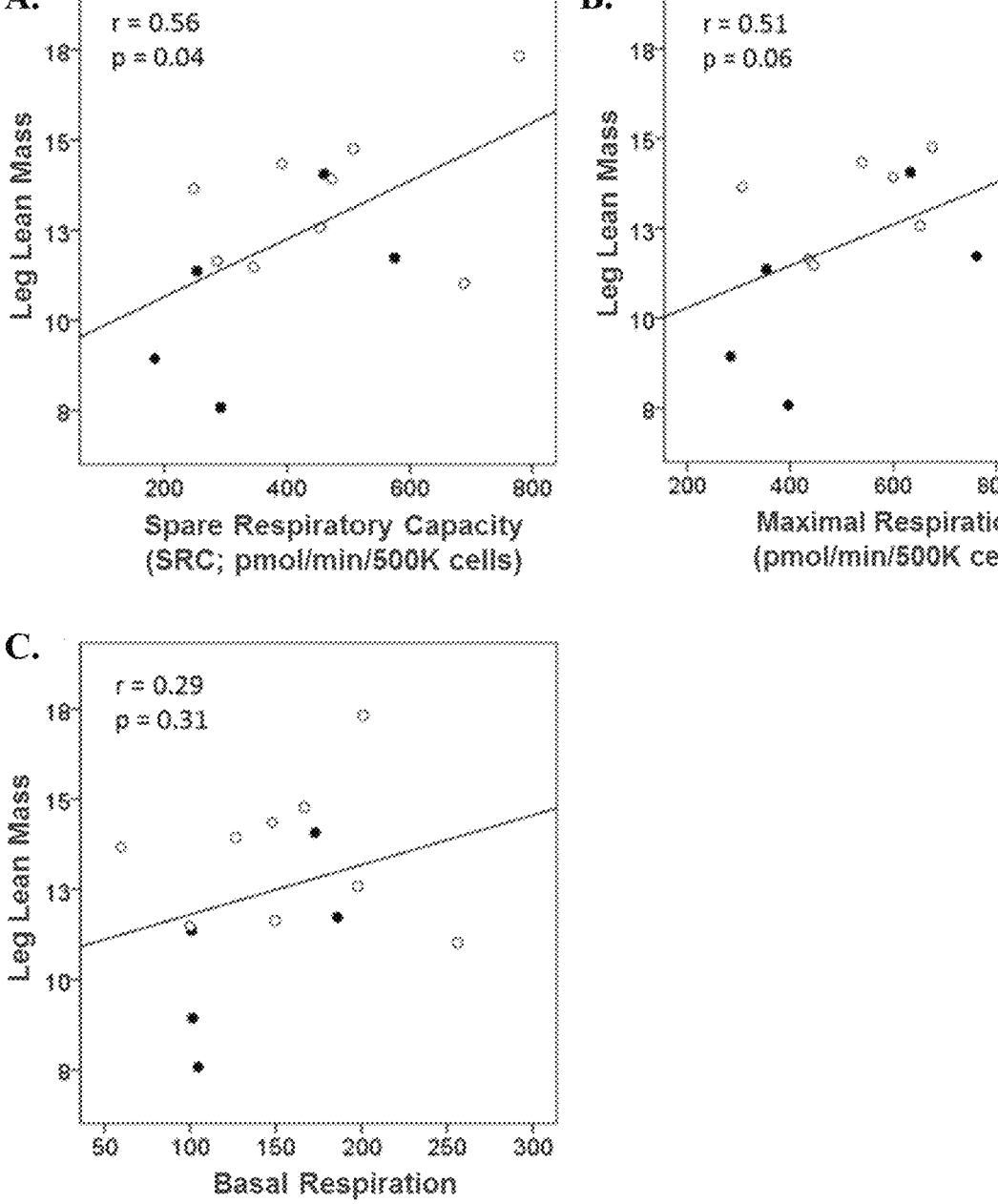
FIG. 9 depicts the relationship between PBMC respiration and leg lean mass according to certain aspects. Leg lean mass measures (kg) are plotted against SRC (A), Max-OCR (B), and basal-OCR measured in PBMCs (C). Gender is indicated as black circles denoting female subjects and white circles denoting male subjects.
Figure 10:
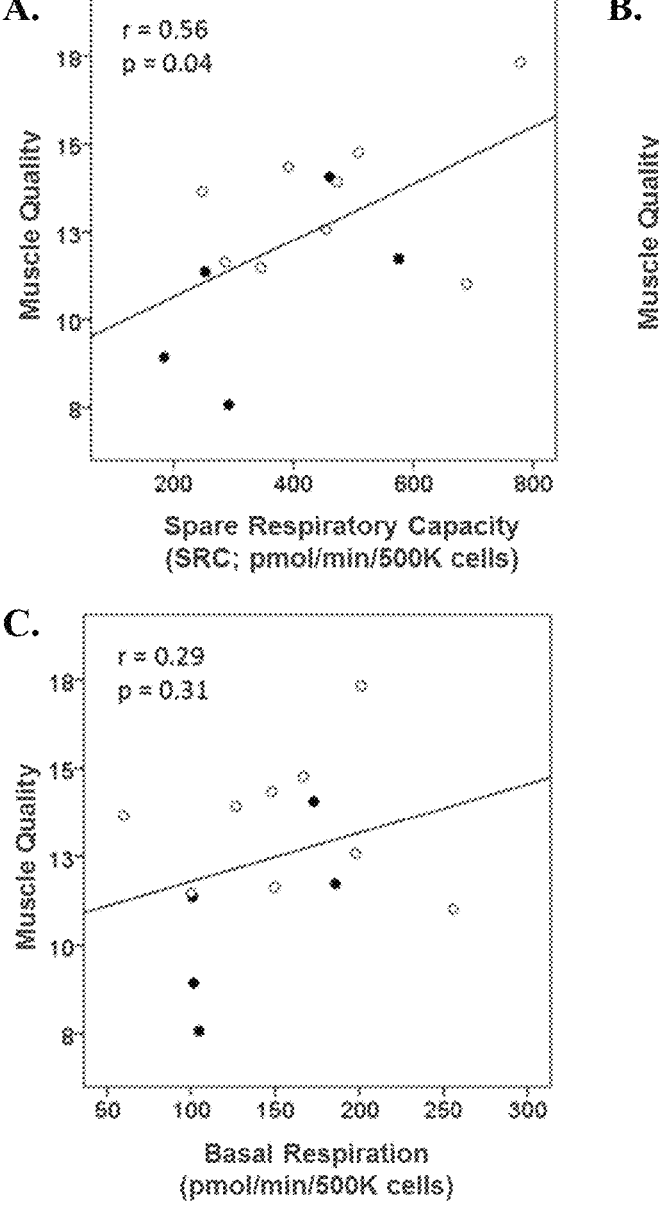
FIG. 10 depicts the relationship between PBMC respiration and muscle quality according to certain aspects. Muscle quality measures (kg) are plotted against SRC (A), Max-OCR (B), and basal-OCR measured in PBMCs (C). Gender is indicated as black circles denoting female subjects and white circles denoting male subjects.
Figure 11:
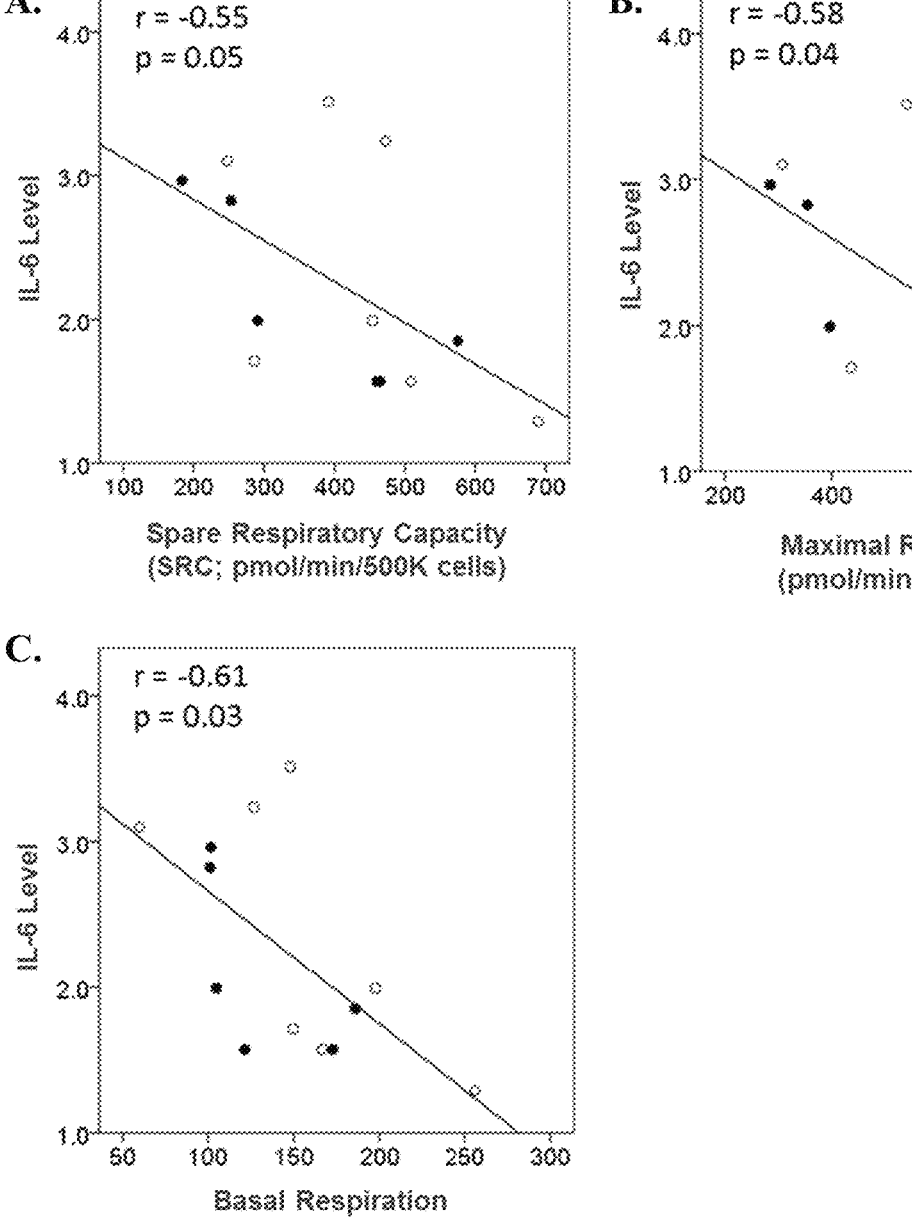
FIG. 11 depicts the relationship between PBMC respiration and interleukin-6 (IL-6) expression according to certain aspects. IL-6 expression is plotted against SRC (A), Max-OCR (B), and basal-OCR measured in PBMCs (C). Gender is indicated as black circles denoting female subjects and white circles denoting male subjects.

In some instances, respiratory capacity of isolated PBMCs, as measured by SRC, Max OCR, and Basal OCR, also is associated with physical ability as measured using the expanded SPPB as shown in FIGS. 6A-6C and Table 2, peak knee extension strength as shown in FIGS. 7A-7C and Table 3, and upper body/grip strength as shown in FIGS. 8A-8C and Table 4, and muscle quality as shown in FIGS. 10A-10C and Table 6. In certain instances, respiratory capacity of isolated PBMCs, as measured by SRC, Max OCR, and Basal OCR, is not associated with lean leg mass as shown in FIGS. 9A-9C and Table 5. In some instances, respiratory capacity of isolated PBMCs, as measured by SRC, Max OCR, and Basal OCR, is negatively correlated with inflammation as measured by interleukin 6 (IL-6) expression, as shown in FIGS. 11A-11C and Table 7. In some instances, isolated lymphocyte and isolated monocyte cell numbers are not associated with the bioenergetic capacity observed in PBMCs, as shown in FIGS. 12A-12C and 13A-13C.

In some cases, the bioenergetic capacity is associated with age and baseline physical ability as described in Example 5. For example, in some instances, as a subject's physical ability improves, the respiratory capacity measured in the subject's isolated circulating blood cells may also increase. In some instances, performance of physical activity in the form of an exercise program (such as aerobic exercise) may increase the respiratory capacity measured in the isolated circulating blood cells of a subject. For example, in some instances, as described in Example 6 and shown in FIG. 14, physical activity in the form of aerobic exercise for two weeks increased the bioenergetic capacity (measured, for example, as SRC) in PBMCs, isolated lymphocytes, isolated monocytes, and isolated platelets obtained from a subject.

In certain instances, bioenergetic capacity of a subject may be improved by diet supplementation with certain nutraceuticals. For example, as described in Example 7, respiratory capacity of isolated circulating blood cells is predicted to increase over time as a subject is administered Vitamin D. Without being held to any particular theory, it is believed that Vitamin D supplementation improves respiratory capacity of isolated circulating blood cells, and of the subject overall, by increasing the levels of plasma 25(OH)D pre-hormone.

In some instances, the respiratory capacity of isolated circulating blood cells may be associated with disease stage for Alzheimer's disease. For example, as described in Example 8, in both humans and non-human primates, the respiratory capacity of isolated circulating blood cells is predicted to identify early stage Alzheimer's disease in subjects not otherwise exhibiting clinical morbidities or other negative factors.

Systems, Devices, and Components for Measuring Respiratory Capacity

Various devices and systems can be used to measure the respiratory capacity of isolated circulating blood cells or isolated mitochondria. Such devices and systems work based on the fact that living cells and isolated mitochondria typically consume nutrients and oxygen from the surrounding medium, and return metabolic byproducts, including ions, carbon dioxide, lactate, and various proteins, to this extracellular environment. The rate of uptake and excretion of these analytes can provide valuable information regarding the metabolic processes underway inside the cells. Examples of such devices will now be described.

The devices and systems used with the described methods and systems generally include small, closed sample chambers configured to contain high densities of cells or isolated mitochondria, preferably in small volumes. In such devices and systems, an active perfusion system may be used to intermittently restore normal levels of dissolved oxygen, pH, and nutrients.

Some approaches to measuring respiratory capacity are based on oxygen flux rate measurements. Some devices and systems monitor respiration in vitro through determination of the rate of depletion of oxygen in the extracellular medium. Some devices and systems rely on the change in total gas pressure in a sealed vessel, using the assumption that this change was primarily due to oxygen consumption. Exemplary devices that assess pressure employ a Clark electrode to measure oxygen partial pressure within a sealed sample vessel. In some instances, devices and systems may employ oxygen electrodes to measure oxygen concentration. Other devices and systems assess oxygen concentration using fluorescent compounds, the fluorescence of which is diminished by the phenomenon of oxygen-quenching, incorporated into or embedded in an oxygen permeable membrane or probe that is exposed to culture medium containing cells or buffer containing isolated mitochondria. Readouts from such devices and systems can be generated using fiber-coupled, semiconductor light sources and sensors. The size of such devices and systems range from fluorescent patches attached to the interior wall of a cell culture bottles or culture plate well, to fluorescent sensors embedded within microscopic flow cells fabricated using microfluidics technology, to microtiter plates with fluorescent compounds suspended within or deposited upon the wells. In some instances, devices and systems can comprise an ion-sensitive field-effect transistor (ISFET) adapted to measure oxygen pressure using enzyme catalyzed conversion of oxygen to hydrogen, when its gate region is exposed to a liquid analyte such as culture medium containing cells or buffer containing isolated mitochondria. (Lehmann et al., *Biosensors & Bioelectronics* 16:195-203 (2001).)

Exemplary devices and systems that can be used to measure respiratory capacity according to the above described methods are described in U.S. Pat. Nos. 7,276, 351; 7,638,321; 7,851,201; 8,697,431; 8,658,349; and 8,202,702 and U.S. Application Nos. 20140248650 and 20140186876, which are incorporated by reference in their entireties. A device and system of this type manufactured by Seahorse Biosciences was used in measuring the respiratory capacity based on oxygen consumption rate in the Examples provided herein. In such devices and systems, a substantially closed sample chamber is temporarily created within a vessel containing a low density mixture of cells in culture medium or isolated mitochondria in buffer, and a sensor or plurality of sensors for measurement of analytes such as oxygen is inserted into the culture medium or buffer to measure the oxygen consumption rate. Reducing the volume of media may include disposing a barrier in the vessel, typically not causing displacement of the media out of the vessel. At least a portion of the barrier may include a sensor. Alternatively or additionally, the reduced volume of media may include a sensor, such as a fluorophore. Because a temporary sample chamber is created within a larger vessel, medium or buffer containing high levels of dissolved oxygen and other analytes, and normal pH, can be supplied to the cells or isolated mitochondria prior to and immediately after a measurement is made. Using this feature, cells can be grown and cells and isolated mitochondria can be maintained for extended periods, treated with drug compounds, and assayed using a variety of methods, while being periodically assayed for viability and respiration rate, without compromising the cells. Furthermore, the medium containing cells or buffer containing mitochondria need not be removed from the vessel; it is only displaced temporarily. In addition, by precisely controlling the dimensions of the temporary sample chamber, a quantitative flux rate for extracellular analytes can be determined easily. Therefore, an external reference is not required; a change in the flux rates of cells in a vessel can be determined from multiple readings of this one vessel. Each vessel, or chamber therein, may contain one or more injection ports through which reagents may be added into the medium or buffer (liquid sample). In some instances, the ports are used in conjunction with actuators that use puffs of air to push reagents into the vessel or chamber thereof. Reagents useful for assessing respiratory capacity include, as described above, ATP synthase inhibitors, mitochondrial uncouplers, mitochondrial Complex I inhibitors, and mitochondrial Complex II inhibitors, amongst others.

One exemplary device of the above-described nature that is useful for analyzing respiratory capacity based on the rate of oxygen consumption in a medium containing cells or buffer containing mitochondria (that is extract of oxygen therefrom) comprises (a) a stage to receive a vessel holding cells and a volume of medium; (b) a plunger with a moveable barrier which alters the volume of medium comprising said cells by relative movement of the stage and the plunger to create a reduced volume of medium comprising said cells or buffer containing mitochondria; and (c) a sensor in sensing communication with the reduced volume of medium comprising said cells or buffer containing mitochondria, wherein the sensor is configured to analyze the cell constituent extracted from or released into the reduced volume. Another exemplary device useful for assessing multiple wells of a multi-well plate simultaneously comprises (a) an array of fluorescent sensors spaced apart so as to match a spacing of at least a portion of the multiple wells; (b) motorized actuators on which the fluorescent sensors are mounted, to control insertion of the fluorescent sensors into and retraction from respective wells of the multi-well plate, wherein the sensors acquire, when in sensing communication with the medium or buffer in the wells, optical signals indicative of concentrations of a solute (such as oxygen) in the medium or buffer disposed in the wells from which an attribute of the cells may be measured, the actuators being moveable in a vertical direction to move the fluorescent sensors relative to the wells to and from a sensing position close to the cells; (c) an electro-optical measurement system in communication with the sensors to interrogate the sensors when in sensing communication with the media in the wells;

(d) a readout to transmit the signals from the sensors to the electro-optical measurement system; and (e) a stage to hold the multi-well plate below the motorized actuators and allow relative movement of the motorized actuators and the multi-well plate with respect to each other. Another exemplary device comprises a plurality of barriers for insertion into respective wells of the multi-well plate, each barrier comprising a barrier surface that creates, when inserted into the respective well, a sample chamber having a reduced volume of medium or buffer less than 50% of the original volume of medium or buffer in the wells by relative movement of the barriers and the multi-well plate, and, disposed on barrier surfaces, fluorescent sensors for analyzing a constituent of the medium disposed about the cells or the buffer disposed about the mitochondria in the respective sample chamber.

Devices and systems such as described above may be used to determine the concentration of oxygen in a buffer containing cells or buffer containing isolated mitochondria in various ways. For example, one method of measuring oxygen concentration in a volume of medium of buffer comprises (a) placing a sample in a vessel (for example, a well of a multi-well plate) in an apparatus comprising: the vessel, including a chamber containing an original volume of medium or buffer and, within the chamber, a surface to hold or contain the sample; a moveable barrier which alters the volume of the medium in contact with the sample; and a sensor in sensing contact with the medium or buffer; (b) moving the barrier to reduce the volume of the chamber and thereby the medium, forming a reduced-volume measuring chamber in contact with the sample; (c) determining a concentration of oxygen in the medium in the reduced volume measuring chamber with the sensor; and (d) moving the barrier to increase the reduced volume of medium or buffer to substantially the original volume. Another method of assessing oxygen concentration in a volume of medium or buffer disposed in a well by a sample containing cells or isolated mitochondria comprises (a) placing in an apparatus a multi-well plate comprising a plurality of said wells, at least one well containing said sample in an original volume of medium or buffer, the apparatus comprising: a plurality of moveable barriers that reduce a volume of the medium or buffer in contact with the samples in the wells; and sensors disposed on respective surfaces of said barriers in sensing contact with the medium or buffer in said wells, each barrier and respective sensor disposed on the surface thereof being configured for insertion into a respective well of the multi-well plate; (b) moving the barriers and sensors into the wells to reduce the volume of the medium about the cells or the buffer about the mitochondria in at least one well, defining a reduced-volume sample chamber in contact with the sample; (c) analyzing with the respective sensor the cell constituent (such as oxygen) in the medium or buffer in the reduced-volume sample chamber; and (d) thereafter, moving the barriers to increase the reduced volume of medium about the cells or buffer about the mitochondria to substantially the original volume. In some instances, the barrier(s) may comprise at least one sensor. In some cases, the barrier(s) may also rotate when not defining the reduced-volume sample chamber to move the culture medium containing cells or buffer containing mitochondria.

In some instances, such devices and systems are optimized for analysis of adherent cells and, for example, analyzing adherent cells while retaining said adherent cells in an in vitro culture. Thus, in some instances, when using such devices and systems to assess the respiratory capacity of a sample containing isolated circulating blood cells or isolated mitochondria, steps may be taken to cause the cells or mitochondria to adhere to an interior bottom surface of the analytical vessel (for example, the interior bottom surface of a well within a multi-well plate). In some instances, such steps are performed to avoid loss of cells or mitochondria from the reduced volume of medium or buffer when the barrier is moved to form the reduced volume of medium or buffer. For example, the way that the Seahorse Biosciences devices, including those described in U.S. Pat. Nos. 7,276, 351; 7,638,321; 7,851,201; 8,697,431; 8,658,349; and 8,202,702 and U.S. Application Nos. 20140248650 and 20140186876, function is that the barrier is moved to form the reduced volume of medium or buffer rapidly and multiple times per time point for reading, creating significant force on the cells or mitochondria present in the medium or buffer. In some instances, if the cells or mitochondria are not adhered to the interior bottom surface of the analytical vessel when the barrier is moved, the cells and mitochondria may be pulled into the displaced volume of medium or buffer, reducing the accuracy of the measurements made as fewer cells or mitochondria remain within the reduced volume of medium or buffer over the time course of analysis.

The devices described in the preceding paragraph can be laborious for high-throughput analysis of samples. In some instances, the reagents useful for assessing respiratory capacity must be manually loaded for injection into each vessel or chamber. For example, in the context of a 24 well multi-well plate, each reagent used (such as ATP synthase inhibitors, mitochondrial uncouplers, mitochondrial Complex I inhibitors, and mitochondrial Complex II inhibitors, amongst others) must be loaded 24 times (once per well).

For example, once the cells or mitochondria are placed into the analytical vessel, the vessel may be centrifuged a relatively high speed to facilitate positioning of the cells or mitochondria along the bottom interior surface of the analytical vessel. In another example, the interior bottom surface of the analytical vessel may be coated with a substance that facilitates the attachment of the cells or mitochondria to the surface such as, for example, poly-D-lysine.

A different type of exemplary device and system that can be used to measure respiratory capacity according to the above described methods are two chamber high resolution respirometers such as those manufactured by Oroboros Instruments. Such devices typically include two chambers made of metal or some other non-oxygen-permeable material. The chambers are filled with a liquid sample comprising isolated circulating blood cells or isolated mitochondria (culture medium or buffer). Oxygen electrodes are submerged in the liquid sample within each chamber to measure the rate of oxygen consumption. Also submerged in the liquid sample within each chamber is a stirrer to keep the isolated cells or mitochondria circulating within the liquid sample within the chamber. In some instances, the oxygen electrodes may be incorporated into the stirrers that are configured to be inserted into each chamber. In some instances, the stirrers and other components of the device and system that come into contact with the liquid sample are not made from or coated with oxygen-permeable materials such as plastic (for example, Perspex® or Teflon®). Such devices and systems may also include titration injection micropumps for insertion of reagents into the liquid sample. Reagents useful for assessing respiratory capacity can include, as described above, ATP synthase inhibitors, mitochondrial uncouplers, mitochondrial Complex I inhibitors, and mitochondrial Complex II inhibitors, amongst others. In some instances, such devices can be employed where a sufficient volume of liquid sample is readily available. The volume of the sample is balanced against the concentration of cells or mitochondria contained therein as, if the liquid sample is too dilute, the oxygen electrodes may not be sufficiently sensitive enough to detect the oxygen in the medium or buffer and the rate of disappearance thereof. In some instances, commercial devices and systems of this nature can require a large volume of sample, which is not desirable in the context of isolated circulating blood cells or isolated mitochondria because a large sample would need to be taken from a subject (such as a large blood draw). Another factor regarding use of such devices is that they generally only have two chambers for receiving liquid samples. Thus, in some instances, only two samples may be assessed at any one time, including, in some cases, a control or reference sample. Thus, high throughput analysis of multiple samples is not possible.

Other devices and systems that are optimized for use with non-adherent cells, such as circulating blood cells, or isolated mitochondria may also be used to perform the above-described methods of the disclosure.

Figure 17:
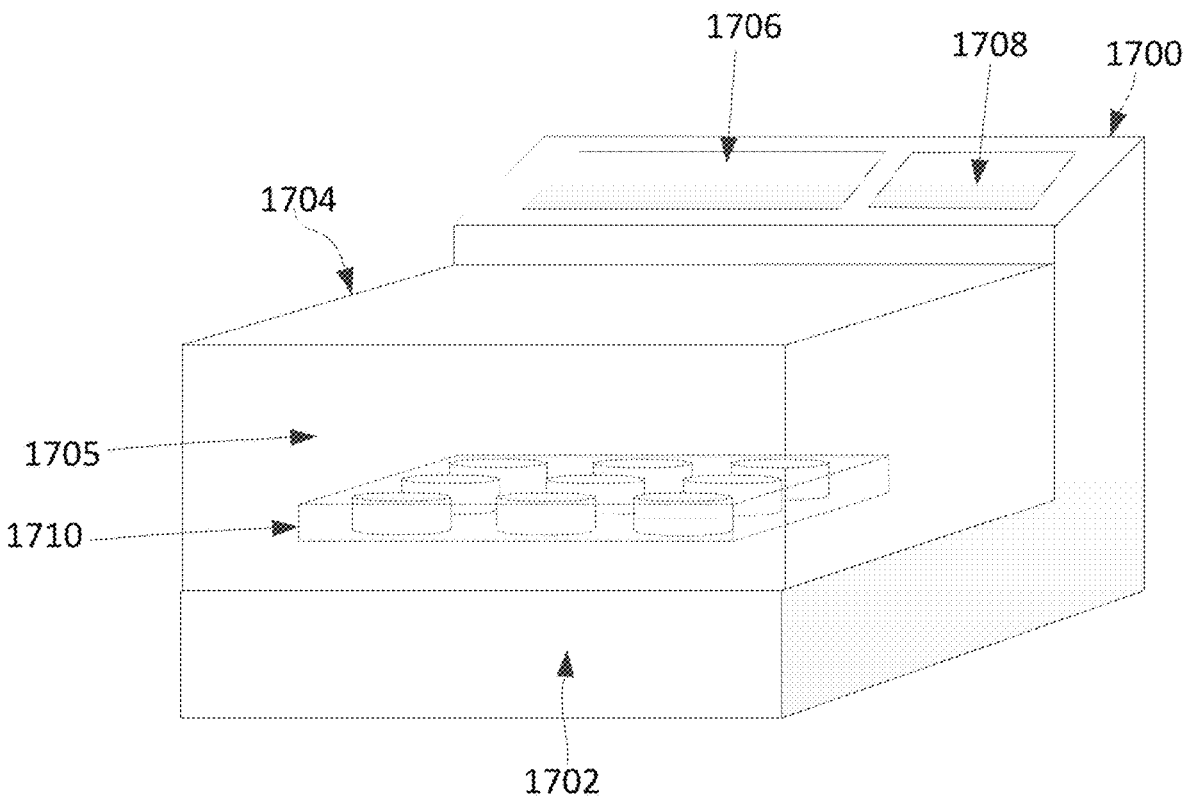
FIG. 17 is an illustration of a respirometry device and system according to some aspects.

For example, FIG. 17 shows an embodiment of a device 1700 optimized for use with non-adherent cells. The device 1700 may comprise a base 1702 upon which the device 1700 is configured to rest. The device 1700 may comprise a lid 1704 or other containment device operable to provide or prohibit access to an internal storage area 1705. In some embodiments, the lid 1704 can be coupled to the base via a pivoting device (e.g., a hinge) for allowing the lid 1704 to open and close. In other embodiments, the lid 1704 can be removably coupled to the base 1702 and configured to be separated from the base 1702.

The lid 1704 may be configured to provide or prohibit access to the internal storage area 1705. The internal storage area 1705 can be configured to receive one or more cartridges 1710. In some embodiments, a cartridge 1710 may be coupled to the device 1700 and positioned within the internal storage area 1705. In other embodiments, the cartridge 1710 may be removably coupled to the device 1700 and positionable within the internal storage area 1705. In such an embodiment, a user may be able to remove and discard the cartridge 1710.

In some embodiments, the device 1700 may comprise a display 1706. The display 1706 may be configured to output one or more graphical objects. In some embodiments, the display 1706 may comprise a touch-screen display. The touch-screen display may be configured to detect user interaction with the touch-screen display and transmit one or more associated sensor signals to a processor (e.g., internal to the device 1700). The sensor signal may comprise data associated with the user interaction, such as a location, direction, and/or pressure of the user interaction.

The device 1700 may additionally or alternatively comprise a user input device 1708. The user input device 1708 may comprise a touch-screen display; a touch pad; a keypad; and/or one or more buttons, knobs, or switches. The user input device 1708 may be configured to receive user input and transmit an associated sensor signal to a processor.

In some cases, the device 1700 may further comprise a computing device. The computing device may be configured substantially the same as the computing device 1501 of FIG. 15. For example, the computing device may comprise a memory and a processor (e.g., the memory device 1504 and the processor 1502 of FIG. 15). The memory may can comprise any suitable tangible (and non-transitory) computer-readable medium such as RAM, ROM, EEPROM, or the like, and may embody program components that configure operation of the device 1700. In some embodiments, the memory may comprise software instructions configured to cause the processor to execute one or more functions. For example, the software instructions may be configured to cause the processor to coordinate the injection of reagents at specific time points into one or more vessels (e.g., vessel 2000 of FIG. 20). In some instances, the processor may process data obtained from an oxygen sensing electrode (e.g., the oxygen sensing electrode 2004 of FIG. 21), or other component configured to assess a liquid sample (e.g., pH meter) within one or more vessels. In some instances, the processor may analyzes a plurality of liquid samples to determine oxygen concentrations of the plurality of liquid samples. The processor may use the oxygen concentrations to calculate the respiratory capacity based on oxygen consumption rate, such as by calculating the Basal OCR and Max OCR and, in some instances, the SRC and/or RCR. In some instances, the memory may comprise software instructions configured to perform any of the methods described throughout this disclosure.

In some cases, the device 1700 may comprise a network interface. The network interface may comprise any components that facilitate a network connection or otherwise facilitate communication between devices. Examples include, but are not limited to, wired interfaces such as Ethernet, USB, IEEE 1394, and/or wireless interfaces such as IEEE 802.11, Bluetooth, near-field communication (NFC) interfaces, RFID interfaces, or radio interfaces for accessing cellular telephone networks (e.g., transceiver/antenna for accessing a CDMA, GSM, UMTS, or other mobile communications network). The device 1700 may use the network interface to transmit the respiratory capacity information to a remote device.

Figure 18:
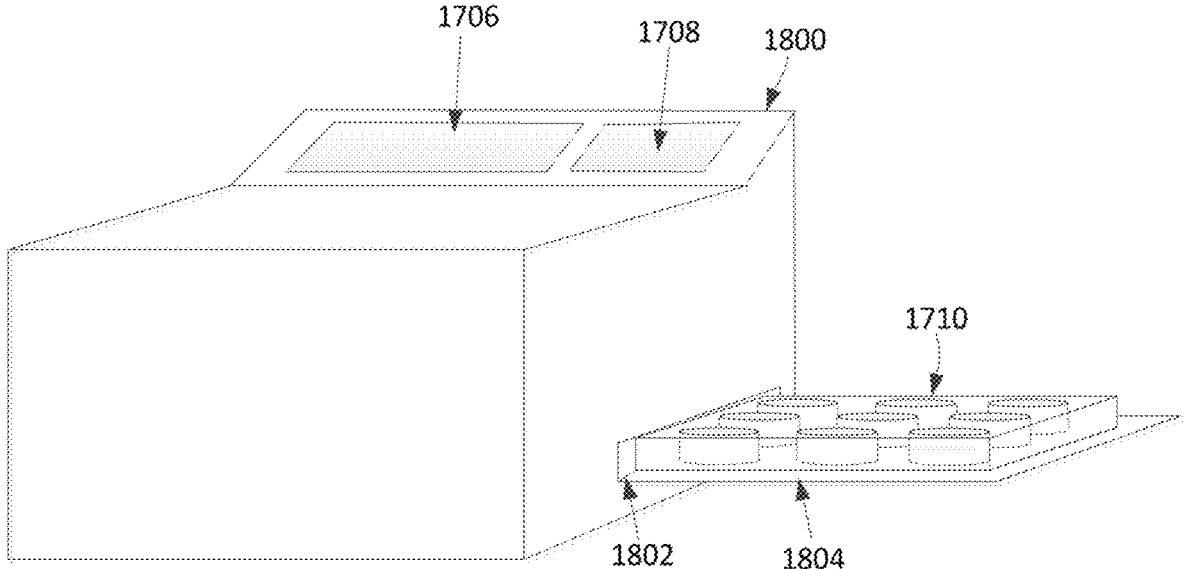
FIG. 18 is an illustration of a respirometry device and system according to some aspects.

FIG. 18 shows another embodiment of a device 1800 optimized for use with non-adherent cells. The device 1800 may be configured to receive a cartridge 1710 via a receptacle 1802 positioned in the side of the device 1800. The receptacle 1802 may comprise a substantially rectangular shape. In some cases, the device 1800 may comprise a tray 1804 configured to slide in and out of the receptacle 1802. The cartridge 1710 can be permanently or removably coupled to the tray 1804. In some embodiments, the cartridge 1710 and the tray 1804 may be a single integrated component. In some embodiments, the movement of the tray 1804 in or out of the receptacle 1802 may be motorized and, in some instances, may be automated (e.g., upon opening of a receptacle covering or door.

Figure 19:
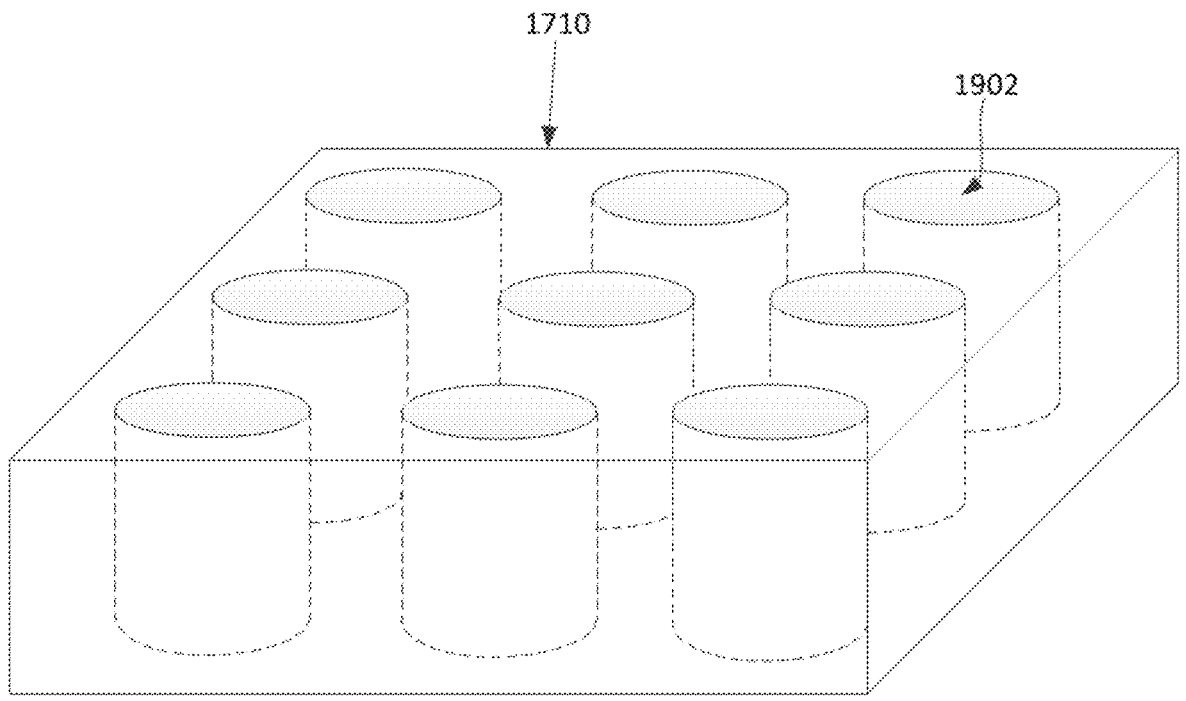
FIG. 19 is an illustration of a cartridge device according to some aspects.

FIG. 19 shows an embodiment of a cartridge 1710 for use with the devices 1700, 1800 of FIGS. 17-18. In this example, the cartridge 1710 comprises a plurality of receptacles 1902 configured to receive a plurality of vessels (e.g., the vessel 2000 of FIG. 20). In some embodiments, the cartridge 1710 may be configured to receive 2, 3, 4, 5, 6, 7, 8, 9, 10, or more disposable vessels 2000. In some instances, each of the receptacles 1902 can include a diameter that is larger than the diameter of a respective vessel. In some embodiments, the cartridge 1710 may comprise plastic, rubber, glass, ceramic, or any other non-magnetic a material. The receptacle 1902 in FIG. 19 is configured to receive vessels (e.g., the vessel 2000 of FIG. 20) that has a circular outer circumference and a round end portion. Other configurations are also contemplated. For example, receptacles 1902 may be configured to receive vessels (e.g., the vessel 2000 of FIG. 20) having a square external circumference and either a rounded or square bottom portion. The length and the width of the receptacles 1092 may be approximately equal, or the length may be greater than the width, or vice versa, to best match the configuration of the vessel to be received.

Figure 20:
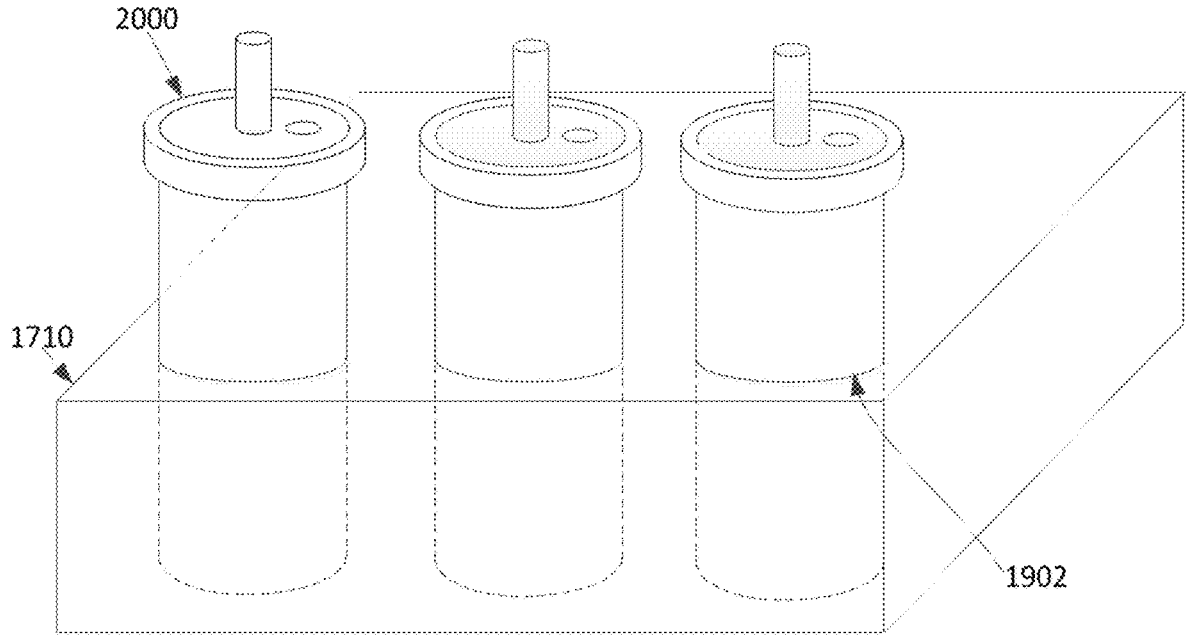
FIG. 20 is an illustration of a cartridge device loaded with a plurality of vessels according to some aspects.

FIG. 20 shows another embodiment of a cartridge 1710. The cartridge 1710 comprises a plurality of vessels 2000 positioned within a plurality of receptacles 1902. In some embodiments, one or more vessels 2000 can be preloaded into or otherwise integrated with the cartridge, for example, during manufacturing. In other embodiments, a user or device can insert one or more vessels 2000 into the cartridge 1710. Each receptacle 1902 of the cartridge 1710 can include one or more locking devices configured to receive a vessel 2000 and removably lock the vessel 2000 in position within the receptacle 1902. For example, in some embodiments, a receptacle 1902 may comprise a snap-in component configured to removably couple with the vessel 2000 for locking the vessel 2000 in place.

In some embodiments, the cartridges 1710 (e.g., comprising with one or more vessels 2000) would be particularly useful for clinical applications in which high throughput analysis of small volume samples is desired. Currently, no such devices and systems are commercially available.

Figure 21:
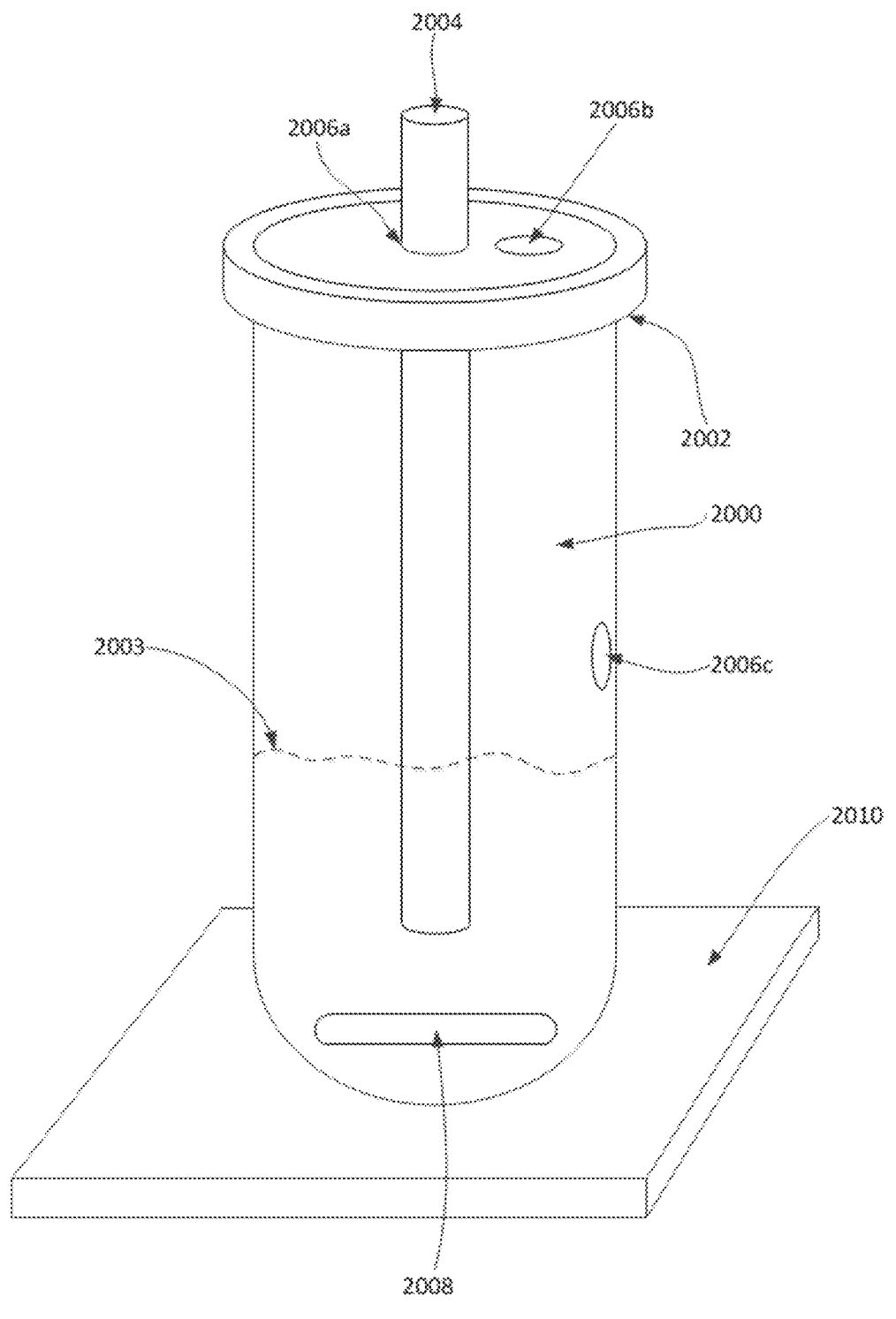
FIG. 21 is an illustration of a vessel according to some aspects.

FIG. 21 shows an embodiment of a vessel 2000 for use with a device 1700, 1800. The vessel 2000 may be configured to be coupled with a cartridge (e.g., cartridge 1710 of FIGS. 17-20) for insertion into the device 1700, 1800. In some embodiments, the vessel 2000 can be disposable and configured to receive one or more liquid samples 2003, such as isolated circulating cells in medium or isolated mitochondria in a buffer. In certain cases, a plurality of liquid samples 2003 comprising isolated circulating blood cells or isolated mitochondria are inserted into at least some of the plurality of vessels 2000. For example, the liquid samples 2003 may be circulating blood cells obtained from different subjects, circulating blood cells isolated from the same subject at different times, different cell types isolated from a single subject, or some combination thereof.

In some instances, the vessel 2000 may be made from materials that are not permeable to oxygen such as, for example, metal or glass. The vessel 2000 may comprise a cap or sealing component 2002 for sealing an opening of the vessel 2000 through which a liquid sample may be inserted into the vessel 2000. In some embodiments, the vessel 2000 may further comprise sealed access ports 2006a-c for the insertion of an oxygen sensing electrode 2004, or other component (e.g., such as described elsewhere in this section), or injection of various reagents useful for assessing respiratory capacity into the vessel 2000. The vessel 2000 may comprise an internal volume of 0.1 mL to 2 mL, 0.1 mL to 0.5 mL, 0.1 mL to 1.0 mL, 0.1 mL to 1.5 mL, 0.2 mL to 0.8 mL, 0.5 mL to 1.5 mL, and any volume ranges therein. In some embodiments, the oxygen sensing electrode 2004 may comprise a square, oval, circular, or other circumferential shape. The oxygen sensing electrode 2004 is configured to electrically coupled with one or more components of a device 1700, 1800 for detecting an amount of oxygen present in a liquid sample 2003 and transmitting an associated sensor signal to the device 1700, 1800. While FIG. 20 illustrates a configuration for vessel 2000 that has a circular outer circumference, a circular internal circumference, and a round end portion, other configurations are also contemplated. For example, vessels 2000 may have a square external circumference, a circular internal circumference, and either a rounded or square bottom portion. The length and the width of the vessel 2000 may be approximately equal, or the length may be greater than the width, or vice versa.

The vessel 2000 may further comprise a mechanism for stirring, or continuously agitating, the liquid sample 2003 within the vessel 2000 to maintain a homogenous mixture of the liquid sample for the duration of the assay. In some instances, stirring or continuously agitating the liquid sample 2003 distributes the oxygen therein uniformly, thereby resulting in accurate readings from the oxygen sensing electrode 2004. For example, a stirrer component 2008 may be inserted through an access port 2006*b-c* into the vessel 2000, wherein a stirrer component 2008 will be submerged within the liquid sample 2003 contained within the vessel 2000 when the liquid sample 2003 inserted therein. In some embodiments, the stirrer component 2008 may comprise a magnetic stir bar and the device or system may further comprise an electromagnetic stir plate 2010 positioned under each vessel 2000. In some instances, the device 1700, 1800 may comprise an orbital shaker component for agitating the vessel 2000 and the cartridge 1710 and the vessel 2000 may not contain a stirrer component 2008.

In some embodiments, the device 1700, 1800 may include one or more reservoirs for reagents and one or more micro-injectors configured to inject reagents from the one or more reservoirs into the plurality of vessels 2000. In some instances, the device 1700, 1800 may further comprise one or more pumps, or other components, to actuate injection of reagents from the one or more reservoirs into the vessels 2000. Reagents useful for assessing respiratory capacity can include, as described above, ATP synthase inhibitors, mito-chondrial uncouplers, mitochondrial Complex I inhibitors, and mitochondrial Complex II inhibitors, amongst others. In certain cases, the device 1700, 1800 may further comprise one of the components described above for assessing pH or another solute dissolved in the liquid sample.

Figure 22:
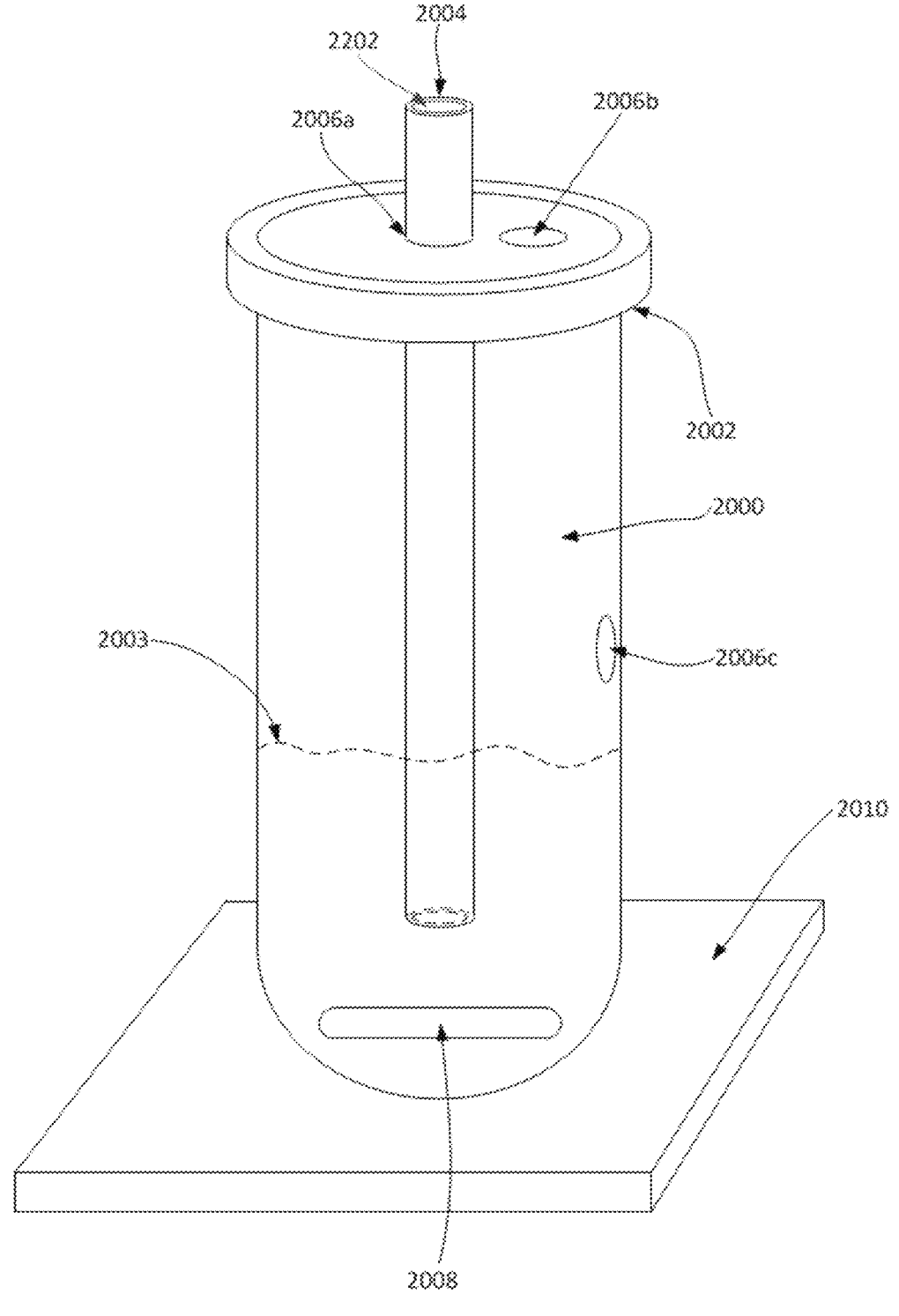
FIG. 22 is an illustration of a vessel according to some aspects.

Referring to FIG. 22, in some embodiments, the vessel 2000 may comprise an oxygen sensing electrode 2004 that includes a hollow interior 2202. The hollow interior 2202 may extend through a longitudinal length of the oxygen sensing electrode 2004. In some embodiments, the oxygen sensing electrode 2004 may be configured to couple with one or more reservoirs of a device 1700, 1800. The device 1700, 1800 may be configured to transmit one or more fluids (e.g., reagents) through the hollow interior 2202 of the oxygen sensing electrode 2004 into the vessel 2000. In some instances, the oxygen sensing electrode 2004 may have a plurality of internal channels that transverse the length of the oxygen electrode 2004. In some cases, the oxygen sensing electrode 2004 having multiple channels therein may be configured to couple with a plurality of reservoirs of a device 1700, 1800. The device 1700, 1800 may be configured to transmit one or more fluids (e.g., reagents) through plurality of internal channels of the oxygen sensing electrode 2004 into the vessel 2000.

Figure 23:
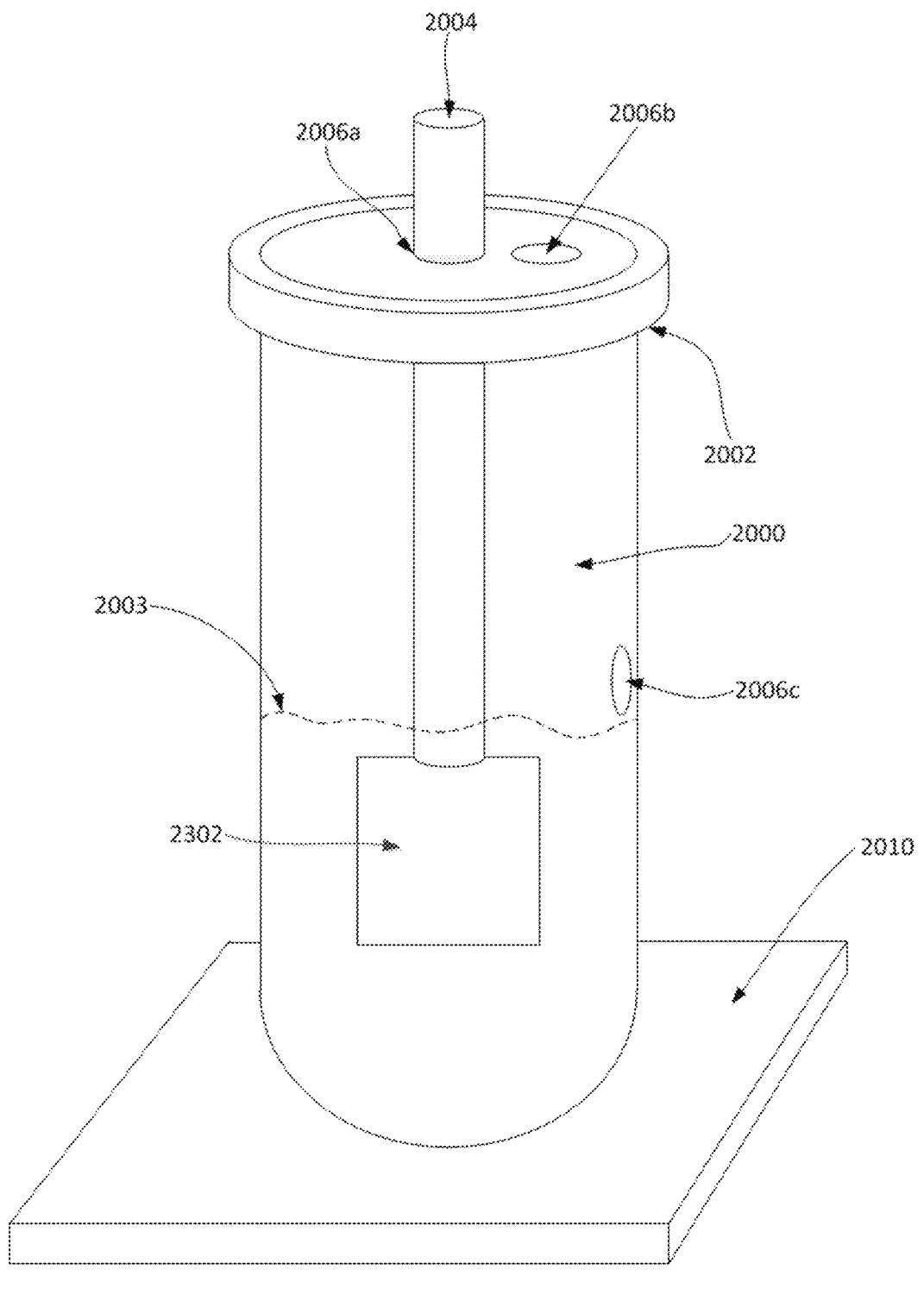
FIG. 23 is an illustration of a vessel according to some aspects.

FIG. 23 shows another embodiment of a vessel 2000 for use with a device 1700, 1800. In this embodiment, the vessel 2000 comprises an the oxygen sensing electrode 2004. The oxygen sensing electrode 2004 comprises a paddle 2302. The paddle 2302 may comprise a magnetic material. In some embodiments, the paddle 2302 may be configured to rotate or spin in response to magnetic forces output by an electro-magnetic stir plate 2010 or other device. In other embodi-ments, a device 1700, 1800 is configured to couple to the oxygen sensing electrode 2004. In such an embodiment, the device 1700, 1800 may comprise one or more motors configured to rotate the oxygen sensing electrode 2004. This may cause the paddle 2302 to spin, thereby stirring, or continuously agitating, the liquid sample 2003 within the vessel 2000. The paddle 2302 in FIG. 23 has a square configuration. However, other configurations are also con-templated.

In some cases, other ions and chemical constituents can be measured using non-invasive techniques based on optical or semiconductor sensors. In some instances, the devices and systems used to assess respiratory capacity may further comprise a pH electrode configured to assess the pH of the culture medium or buffer. In some instances, the devices and systems may comprise sensors for the detection of carbon dioxide, such as fluorescent sensors that can detect partial pressure in culture medium or buffer similarly as described above for measuring of oxygen. Various sensors can be included that are configured to come into contact with the culture medium containing cells or the buffer containing isolated mitochondria. The sensors may be one or more of a fluorescent sensor, a luminescent sensor, an ISFET sensor, a surface plasmon resonance sensor, a sensor based on an optical diffraction principle, a sensor based on a principle of Wood's anomaly, an acoustic sensor, or a microwave sensor.

Systems Utilizing Respiratory Capacity Measurements

In another aspect, the invention comprises systems com-prising a first computing device, the first computing device in communication with a database; a first application execut-ing on the first computing device, the first application configured to receive a plurality of laboratory test results for a plurality of subjects and store the plurality of laboratory test results in the database, wherein the plurality of labora-tory test results comprise a measure of respiratory capacity determined in a blood sample obtained from the subject; a second computing device, the second computing device in communication with the database; and a second application executing on the second computing device, the second application configured to query the database for laboratory test results for a subject from the plurality of subjects; receive the laboratory test results for the subject from the database; determine a test result based at least in part on the received laboratory test results for the subject, the test results comprising a measure of respiratory capacity determined in a blood sample obtained from the subject; generate a test result report for the subject, the test result report comprising the systemic respiratory capacity of the subject and based at least in part on the test result for the subject; and transmit the test result report for the patient to a third computing device.

Figure 15:
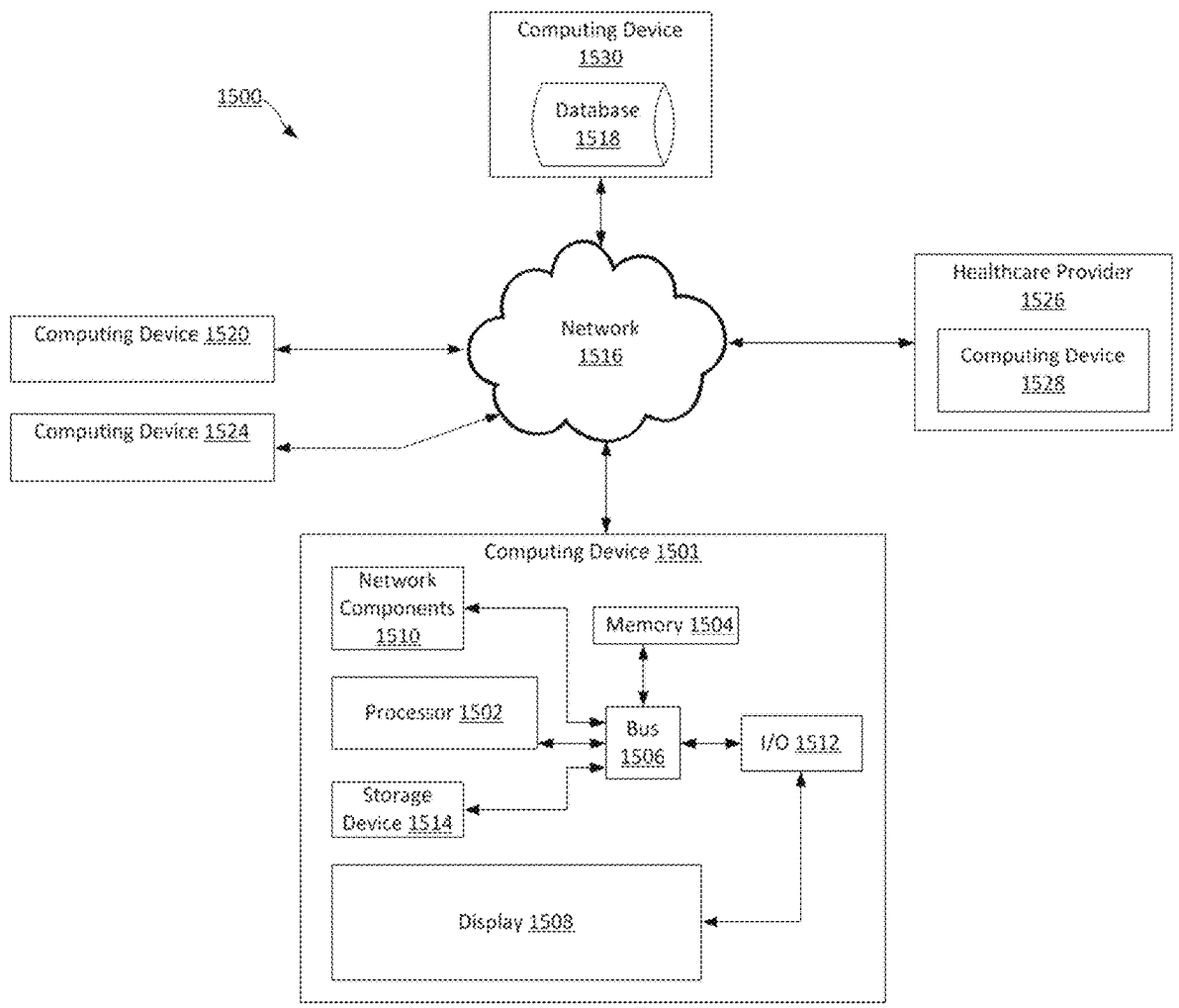
FIG. 15 depicts a system diagram depicting exemplary computing devices in an exemplary computing environment according to certain aspects.

In some embodiments, the invention comprises a system, for example, the system 1500 shown in FIG. 15. The system 1500 includes various components. As used herein, the term "component" is broadly defined and includes any suitable apparatus or collections of apparatuses suitable for carrying out the recited method. The components need not be inte-grally connected or situated with respect to each other in any particular way. Embodiments include any suitable arrange-ments of the components with respect to each other. For example, the components need not be in the same room. But in some embodiments, the components are connected to each other in an integral unit. In some embodiments, the same components may perform multiple functions.

The system 1500 may comprise one or more computing devices 1501. Typical examples of computing devices 1501 include a general-purpose computer, a printer, a pro-grammed microprocessor, a microcontroller, a peripheral integrated circuit element, and other devices or arrange-ments of devices that are capable of implementing the steps that constitute the method of the present technique.

The computing device 1501 comprises a memory 1504. The memory 1504 may include random access memory (RAM) and read only memory (ROM), as well as removable media devices, memory cards, flash cards, etc. The comput-ing device 1501 may further comprise a storage device 1514. The storage device 1514 can be a hard disk drive or a removable storage drive such as a floppy disk drive, optical disk drive, etc. The storage device 1514 can also be other similar means for loading computer programs or other instructions into the computing device 1501.

A computing device 1501 also comprises a processor 1502. The processor 1502 executes a set of instructions that are stored in one or more storage elements (e.g., memory 1504 or storage device 1514), in order to process input data. The storage elements may also hold data or other information as desired. The storage elements may be in the form of an information source or a physical memory 1504 element present in the processing machine.

A computing device 1501 typically will include an operating system that provides executable program instructions for the general administration and operation of that computing device 1501, and typically will include a computer-readable storage medium (e.g., a hard disk, random access memory, read only memory, etc.) storing instructions that, when executed by the processor 1502, allow the computing device 1501 to perform its intended functions. Suitable implementations for the operating system and general functionality of the computing device 1501 are known or commercially available, and are readily implemented by persons having ordinary skill in the art, particularly in light of the disclosure herein.

As discussed above, some embodiments comprise a processor 1502 which is configured to execute computer-executable program instructions and/or to access information stored in memory 1504. The instructions may comprise processor-specific instructions generated by a compiler and/or an interpreter from code written in any suitable computer-programming language including, for example, C, C++, C#, Visual Basic, Java, Python, Perl, JavaScript, and Action-Script. The set of instructions for execution by the computing device 1501 may include various commands that instruct the processor 1502 to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

In some embodiments, the computing device 1501 may comprise a single processor 1502. In other embodiments, the computing device 1501 comprises two or more processors. Such processors 1502 may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices. The processor 1502 is connected to a communication bus 1506. The communication bus 1506 may be connected to one or more other components, for example, the processor 1502, an input device (e.g., a mouse, keyboard, controller, touch screen, or keypad), and an output device (e.g., a display 1508, printer, or speaker).

The computing device 1501 can also include network components 1510. The network components 1510 allow the computing device 1501 to connect to one or more networks 1516 and/or other databases (e.g., database 1518) through an I/O interface. Although depicted in FIG. 15 as a single network 1516, the network 1516 can include any number of networks. The network components 1510 allow the transfer to, as well as reception of data from, a network 1516 and/or databases. The network components 1510 may include a modem, an Ethernet card, or any similar device which enables the computing device 1501 to connect to databases and/or networks 1516 such as LAN, MAN, WAN and the Internet. The network components 1510 may comprise a network interface. In some embodiments, the network interface is configured for communicating via wired or wireless communication links. For example, the network components 1510 may allow for communication over networks via Ethernet, IEEE 802.11 (Wi-Fi), 802.16 (Wi-Max), Bluetooth, infrared, etc. As another example, the network interface may allow for communication over networks such as CDMA, GSM, UMTS, or other cellular communication networks. In some embodiments, the network components 1510 may allow for point-to-point connections with another device, such as via the Universal Serial Bus (USB), 1394 FireWire, serial or parallel connections, or similar interfaces. Some embodiments of suitable computing devices 1501 may comprise two or more network interfaces for communication over one or more networks. In some embodiments, the computing device 1501 may include a database in addition to or in place of a network components 1510.

The system 1500 can include a variety of data stores and other memory and storage media as discussed above. These can reside in a variety of locations, such as on a storage medium local to (and/or resident in) one or more of the computing devices 1501 or remote from any or all of the computing devices 1501 across the network 1516. In a particular set of embodiments, the information may reside in a storage-area network (SAN) familiar to those skilled in the art. Similarly, any necessary files for performing the functions attributed to the computers, servers, or other network devices may be stored locally and/or remotely, as appropriate.

Computing device 1501 can also include a computer-readable storage media reader. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system 1500 and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices 1520, 1524, such as network input/output devices, may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system 1500 device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory (CAM), DDR, flash memory such as NAND flash or NOR flash, an ASIC, a configured processor, optical storage, magnetic tape or other magnetic storage, or any other medium from which a computer processor can read instructions. In one embodiment, the computing device 1501 may comprise a single type of computer-readable medium such as random access memory (RAM). In other embodiments, the computing device 1501 may comprise two or more types of computer-readable medium such as random access memory (RAM), a disk drive, and cache. The computing device 1501 may be in communication with one or more external computer-readable mediums such as an external hard disk drive or an external DVD drive.

The computing device 1501 may further include I/O components 1512, which may be used to facilitate wired or wireless connection to input and output devices. Some embodiments of suitable computing devices 1501 may comprise or be in communication with a number of external or internal devices such as a mouse, a CD-ROM, DVD, a keyboard, a display 1508, audio speakers, one or more microphones, or any other input or output devices. For example, the computing device 1501 may be in communication with various user interface devices and a display 1508. The display 1508 may use any suitable technology including, but not limited to, LCD, LED, CRT, and the like.

The system 1500 may include any number of computing devices 1501. For example, in one embodiment, the system 1500 includes one computing device 1501. In the example shown in FIG. 15, the system 1500 includes a plurality of computing devices 1501, 1520, 1524, 1528, 1530. The computing devices 1501, 1520, 1524, 1528, 1530 may be of the same or different types. For example, in some embodiments, computing device 1501 may comprise a desktop computer, while computing device 1524 may comprise a printer. Further, in some embodiments, the computing devices 1501, 1520, 1524, 1528, 1530 may be at the same or different locations. For example, in the embodiment shown in FIG. 15, one computing device 1501 may be located onsite at a testing center, while another computing device 1528 may be located offsite at a healthcare provider's office.

The system 1500 further includes a database 1518. The one or more computing devices 1501 are in communication with the database 1518. In some embodiments, the database 1518 may comprise, for example, a MySQL database. The database 1518 may contain data that may be retrievable by one or more computing devices (e.g., computing device 1501, 1520 or 1528). In some embodiments, the database 1518 may itself be a part of a computing device 1530. The database 1518 may comprise data related to subject information, subject sample information, reference population, treatment options, healthcare provider information, laboratory test results, and laboratory test reports. For example, data related to subjects may include subject names, addresses, telephone numbers, subject identification numbers, providers to which the subjects are associated, medical history (including, e.g., disorder or disease status, prior test results, other test results), medications and/or treatments, relatives, health care provider plans, account balances, access information, or other information related to one or more subjects. Data related to subject samples may include subject names, addresses, telephone numbers, subject identification numbers, date of collection, sample type (e.g., cell type, cell number), sample volume, disease status (e.g., diagnosed disorders, predisposition factors, medications taken), date of collection/processing/analysis of samples, laboratory test results, providers to which the subjects are associated, medical history (including, e.g., disease status, prior test results, other test results), medications and/or treatments, relatives, health care provider plans, account balances, access information, or other information related to one or more subjects. Data related to the reference population can include reference population subject information, reference population subject sample information, and information relating to clinical study participation, the amount of respiratory capacity measured in blood samples from the reference population subjects, which may include measures of oxygen consumption rate (basal and/or maximal), spare respiratory capacity, and/or respiratory control ratio. In some instances, the data relating to the reference population comprises that a Max OCR of about 250 pmol/min/500,000 cells, a SRC of about 100 pmol/min/500,000 cells, and/or a SRC of about 40% of Max OCR. Data for each reference population subject individually and for the reference population as a whole (e.g., median respiratory capacity measurements) may be included. In some embodiments, the reference population comprises healthy, age-match subjects. In some embodiments, the reference population comprises subjects with the same type of ailment, disease or disorder as the subject. Data related to healthcare providers can include names, addresses, phone numbers, personnel, usernames, passwords, other security information, access levels, and other information associated with one or more providers. Data related to laboratory test results can include the measures of oxygen consumption rate (basal and/or maximal), spare respiratory capacity, and/or respiratory control ratio in a blood sample obtained from the subject. Data related to the test results may include measures of oxygen consumption rate (basal and/or maximal), spare respiratory capacity, and/or respiratory control ratio in a blood sample obtained from the subject, the systemic respiratory capacity of the subject, and/or the bioenergetic signature of the subject. Data related to test result reports can include the systemic respiratory capacity and/or the bioenergetic signature of the subject and be based at least in part on the test result for the subject and reference population information.

In some embodiments, the system 1500 may execute one or more applications. The one or more applications may be executed on any number of computing devices (e.g., computing devices 1501, 1520, 1524, 1528, or 1530). In some embodiments, the system 1500 may execute an application configured to receive a plurality of laboratory test results. In some embodiments, the plurality of laboratory test results may be for a plurality of subjects. In other embodiments, the plurality of laboratory test results may be for a single subject. The system 1500 may store the plurality of laboratory test results in the database 1518.

The system 1500 may also execute an application configured to query the database 1518 for laboratory test results associated with one or more subjects. The system 1500 may determine a test result based at least in part on the received laboratory test results for the one or more subjects. In some embodiments, the test result may comprise a measure of respiratory capacity of the subject. In some embodiments, the test result may also comprise the systemic respiratory capacity of the subject.

In some embodiments, based on the test results, the system 1500 may generate a test result report for the one or more subjects. The test result report may comprise, for example, the respiratory capacity of the subject. For example, in some embodiments, the test result report may include the systemic respiratory capacity of the subject, measures of respiratory capacity in the subject (such as, e.g., oxygen consumption rate (basal and/or maximal), spare respiratory capacity, and/or respiratory control ratio) in a blood sample obtained from the subject, the bioenergetic signature of the subject, and/or the median amount of respiratory capacity in the reference population (e.g., median measures of oxygen consumption rate (basal and/or maximal), spare respiratory capacity, and/or respiratory control ratio). In some embodiments, the test result report is generated by comparing the respiratory capacity in the blood sample obtained from the subject to the median respiratory capacity in a reference population of subjects. In some embodiments, the test result report is generated by comparing the bioenergetic signature of the subject to bioenergetic signatures identified in the reference population. In some embodiments, the reference population comprises healthy, age-matched subjects. In some embodiments, the reference population comprises subjects with the same type of ailment, disorder or disease as the subject.

In some embodiments, the test result report comprises information that the subject has a high respiratory capacity if (i) the respiratory capacity measured in the blood sample is above the median measure of respiratory capacity in a reference population. In some embodiments, the test result report comprises information that the subject has a decreased likelihood of morbidity or death if a relatively high respiratory capacity is measured in the isolated cells from the blood sample, compared to the reference population, and has an increased likelihood of morbidity or death if a relatively low respiratory capacity is measured in the isolated cells compared to the reference population. In some embodiments, the test result report comprises information that the subject an increased likelihood of a positive clinical outcome if a relatively high respiratory capacity is measured in the isolated cells from the blood sample from the subject compared to the reference population, and a decreased likelihood of a positive clinical outcome if a relatively low respiratory capacity is measured in the isolated cells compared to the reference population. In some embodiments, the test result report comprises information that the subject is likely to benefit from an aggressive treatment strategy if a relatively high respiratory capacity is measured in the isolated cells from the blood sample from the subject, and is likely to not benefit from an aggressive treatment strategy if a relatively low respiratory capacity is measured in the isolated cells compared to the reference population. In some instances, the test result report comprises information that the subject has an increased likelihood of morbidity or diminished life expectancy if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject has a decreased likelihood of morbidity or diminished life expectancy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has an increased likelihood of a positive clinical outcome if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has an increased likelihood of a positive clinical outcome if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject is not likely to benefit from an aggressive treatment strategy for a disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject is likely to benefit from an aggressive treatment strategy for a disease if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has a decreased likelihood of benefiting from rehabilitation therapy if at least one of the following conditions is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject has an increased likelihood of benefiting from rehabilitation therapy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

In some embodiments, the system 1500 may transmit the test result report. In some embodiments, the system 1500 may transmit the test report to a computing device, for example, computing device 1520. In some embodiments, the system 1500 may transmit the test result report to one or more recipients. In some embodiments, the recipient may be the subject or a healthcare provider. In some embodiments, the system 1500 may transmit the test result report via e-mail (e.g., to an e-mail account associated with the subject's healthcare provider), SMS, or text message.

In some embodiments, the system 1500 may store the test result report in the database 1518. Further, the system 1500 may provide an electronic notification to a computing device 1528. The computing device 1528 may be associated with a healthcare provider 1526, which may be associated with the subject. In some embodiments, the electronic notification may comprise an e-mail, a text message, or a push notification. The electronic notification may indicate that a test report is available, for example, for download from the database 1518.

Methods of Utilizing Respiratory Capacity Measurements

In another aspect, the invention comprises methods comprising receiving a plurality of laboratory test results in a database, wherein the plurality of laboratory test results comprise a measure of respiratory capacity determined in a blood sample obtained from the subject; storing the plurality of laboratory test results in the database; querying the database for laboratory test results for a subject from the plurality of subjects; receiving the laboratory test results for the subject from the database; determining a test result based in part on the received laboratory test results for the subject, the test result comprising the respiratory capacity of the subject and based at least in part on the test result for the subject; generating a test result report for the subject, the test result report comprising the systemic respiratory capacity of the subject and based at least in part on the test result for the subject; and transmitting the test result report for the subject to a computing device. FIG. 16 is a flow chart of steps for performing the method.

In some embodiments, the steps in FIG. 16 may be implemented in program code that is executed by a processor, for example, the processor in a general purpose computer, a mobile device, or a server. In some embodiments, these steps may be implemented by a group of processors. In some embodiments one or more steps shown in FIG. 16 may be omitted or performed in a different order. Similarly, in some embodiments, additional steps not shown in FIG. 16 may also be performed. The steps below are described with reference to components described above with regard to system 1500 shown in FIG. 15.

The method 1600 begins at step 1602 when processor 1502 receives a plurality of laboratory test results for a plurality of subjects. In some embodiments, the plurality of laboratory test results may include the measures of oxygen consumption rate (basal and/or maximal), spare respiratory capacity, and/or respiratory control ratio in a blood sample obtained from the subject.

The method 1600 continues at step 1604 when processor 1502 stores the plurality of laboratory test results in a database 1518. In some embodiments, the processor 1502 may be in communication with the database 1518 via a LAN, WAN, or the Internet. In other embodiments, the database 1518 may be internal to the computing device 1501 housing the processor 1502, and the processor 1502 may be in communication with the database 1518 via a bus 1506 or other hardware configuration. The processor 1502 may transmit data associated with the plurality of laboratory test results to the database 1518.

The method 1600 continues at step 1606 when processor 1502 queries the database 1518 for laboratory test results for a subject from the plurality of subjects. The processor 1502 may query the database by transmitting one or more commands to the database 1518 (and/or a computing device 1530 housing the database 1518). The computing device 1530 housing the database 1518 may perform one or more steps to retrieve the laboratory test result data from the database 1518. Further, the computing device 1530 housing the database 1518 may transmit the queried laboratory test result data to the processor 1502.

The method 1600 continues at step 1608 when processor 1502 receives the laboratory test results for the subject from the database 1518. In some embodiments, the processor 1502 may be receive the laboratory test result data via a LAN, WAN, or Internet connection. In some embodiments, the processor 1502 may store the laboratory test result data in memory 1504.

The method 1600 continues at step 1610 when processor 1502 determines a test result based at least in part on the received laboratory test results for the subject. In some embodiments, the test result may include measures of oxygen consumption rate (basal and/or maximal), spare respiratory capacity, and/or respiratory control ratio in a blood sample obtained from the subject, and/or the systemic respiratory capacity of the subject. In some embodiments, the processor 1502 may determine the test result based at least in part on the received laboratory test results for the subject, the test results comprising a measure of respiratory capacity in the subject, such as, e.g., measures of oxygen consumption rate (basal and/or maximal), spare respiratory capacity, and/or respiratory control ratio in a blood sample obtained from the subject, and/or the systemic respiratory capacity of the subject. In some embodiments, the processor 1502 may further determine information about the average or median respiratory capacity in a reference population, as assessed by, e.g., measures of oxygen consumption rate (basal and/or maximal), spare respiratory capacity, and/or respiratory control ratio in a blood sample obtained from the subject, and/or average or median systemic respiratory capacity of the reference population. For example, in some embodiments, the processor 1502 may determine the measures of oxygen consumption rate (basal and/or maximal), spare respiratory capacity, and/or respiratory control ratio in a blood sample obtained from the subject. In some embodiments, the processor 1502 may also determine the systemic respiratory capacity and/or the bioenergetic signature of the subject. In some embodiments, the processor 1502 may compare the respiratory capacity of the subject to the median respiratory capacity in the reference population. In some embodiments, the processor 1502 may compare the bioenergetic signature of the subject to bioenergetic signatures identified in the reference population. In some embodiments, the reference population comprises healthy, age-matched subjects. In some embodiments, the reference population comprises subjects with the same type of ailment, disorder or disease as the subject. In some embodiments, the processor 1502 may compare the respiratory capacity measured in a subject to known respiratory capacity cutoffs (e.g., as determined in a reference population). For example, in some instances, the known respiratory capacity cutoffs may include a Max OCR of about 250 pmol/min/500,000 cells, a SRC of about 100 pmol/min/500,000 cells, and/or a SRC of about 40% of Max OCR.

The method 1600 continues at step 1612 when processor 1502 generates a test result report for the subject, the test result report comprising the systemic respiratory capacity and/or the bioenergetic signature of the subject and based at least in part on the test result for the subject. The test result report may comprise the additional determined information about the amount different measures of respiratory capacity in the subject, including measures of oxygen consumption rate (basal and/or maximal), spare respiratory capacity, and/or respiratory control ratio in a blood sample obtained from the subject. In some embodiments, the test result report comprises information that the subject has a high respiratory capacity if (i) the respiratory capacity measured in the blood sample is above the median measure of respiratory capacity in a reference population. In some embodiments, the test result report comprises information that the subject has a decreased likelihood of morbidity or death if a relatively high respiratory capacity is measured in the isolated cells from the blood sample, compared to the reference population, and has an increased likelihood of morbidity or death if a relatively low respiratory capacity is measured in the isolated cells compared to the reference population. In some embodiments, the test result report comprises information that the subject an increased likelihood of a positive clinical outcome if a relatively high respiratory capacity is measured in the isolated cells from the blood sample from the subject compared to the reference population, and a decreased likelihood of a positive clinical outcome if a relatively low respiratory capacity is measured in the isolated cells compared to the reference population. In some embodiments, the test result report comprises information that the subject is likely to benefit from an aggressive treatment strategy if a relatively high respiratory capacity is measured in the isolated cells from the blood sample from the subject, and is likely not to respond well to/not benefit from an aggressive treatment strategy if a relatively low respiratory capacity is measured in the isolated cells compared to the reference population. In some instances, the test result report comprises information that the subject has an increased likelihood of morbidity or diminished life expectancy if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject has a decreased likelihood of morbidity or diminished life expectancy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has an increased likelihood of a positive clinical outcome if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has an increased likelihood of a positive clinical outcome if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject is not likely to benefit from an aggressive treatment strategy for a disease if at least one of the following is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject is likely to benefit from an aggressive treatment strategy for a disease if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR. In some instances, the test result report comprises information that the subject has a decreased likelihood of benefiting from rehabilitation therapy if at least one of the following conditions is determined: i) a Maximum Oxygen Consumption Rate (Max OCR) of less than about 250 pmol/min/500,000 cells, ii) a Spare Respiratory Capacity (SRC) of less than about 100 pmol/min/500,000 cells, or iii) a SRC of 40% or less of a Max OCR. In some instances, the test result report comprises information that the subject has an increased likelihood of benefiting from rehabilitation therapy if at least one of the following is determined: i) a Maximum Oxygen Consumption Rate (Max OCR) of greater than about 250 pmol/min/500,000 cells, ii) a Spare Respiratory Capacity (SRC) of greater than about 100 pmol/min/500,000 cells, or iii) a SRC of 40% or greater of a Max OCR.

The method 1600 continues at step 1614 when processor 1502 stores the test result report for the subject in the database 1518. The processor 1502 may transmit data associated with the test result report to the database 1518. In some embodiments, a healthcare provider 1526 (e.g., the patient's healthcare provider) may be able to access the stored test result report. For example, in some embodiments, the healthcare provider 1526 may be able to query the database 1518 directly or indirectly.

The method 1600 continues at step 1616 when processor 1502 transmits an electronic notification to a computing device 1528. The electronic notification may indicate that a test report is available, for example, for download from the database 1518. In some embodiments, the computing device 1528 may be associated with a healthcare provider 1526 or the subject. In some embodiments, the electronic notification may comprise an e-mail, a text message, or a push notification.

The method 1600 continues at step 1618 when processor 1502 transmits the test result report for the subject to a computing device 1520. In some embodiments, the processor 1502 may transmit the test result report to a computing device 1520 associated with the subject. In some embodiments, the processor 1502 may transmit the test result report to a computing device 1528 associated with a healthcare provider 1526. In some embodiments, the processor 1502 may transmit the test result report via e-mail (e.g., to an e-mail account associated with the subject's healthcare provider), SMS, or text message.

It should be understood that is contemplated and therefore within the scope of the invention that any above-disclosed element of the invention as described herein can be combined with any other disclosed element of the invention or any combination of elements can be combined with any element or combination of elements as described herein.

EXAMPLES

The present invention may be better understood by reference to the following non-limiting examples.

Example 1

The Examples of the application describe experiments analyzing various types of biological samples, including muscle biopsies and circulating cells.

Muscle and blood samples from non-human primate subjects were obtained from necropsies. Muscle biopsies and blood draws from human subjects were performed in the morning after an overnight fast. Muscle tissue (vastus lateralis; ~100-120 mg) was extracted via percutaneous needle biopsy with local anesthesia. Tissue was processed immediately after collection. Muscle tissue was visualized with a dissecting microscope and residual fat was manually teased apart and removed with fine forceps. About 50 mg of muscle tissue was used for mitochondrial isolation using differential centrifugation techniques based on the Chappell and Hansford method. (Hansford and Chappell, *Biochem. Biophys. Res. Commun.* 27(6):686-692 (1967).) Whole blood (8 mL) was collected into cell preparation tubes (Vacutainer®, Becton, Dickinson & Co.) for PBMC separation. PBMCs were isolated from whole blood using Ficoll-isopaque gradient (BD Vacutainer® CPT™ Cell Preparation Tube (catalog #: 362761)).

Example 2

A Seahorse XF$^e$24 Extracellular Flux Analyzer™ (North Billerica, Mass.) was used for respirometry analysis—i.e., measurement of oxygen consumption rate (OCR). The system has a 24-well and a 96-well format that enables simultaneous measurement of mitochondrial respiration and glycolysis. The system also enables the use of small sample sizes and multiple repeats per run. Parallel measurements of bioenergetic capacity were performed on mitochondrial preparations obtained from muscle biopsies and isolated PBMCs from the same subjects.

Basal respiration, maximal respiration, and proton leak contribute to the respiratory capacity of a cell. There are numerous methods for measuring mitochondrial function in isolated organelles and whole cells. (Brand and Nicholls, *Biochem. J.* 435(2):297-312 (2011).) For isolated mitochondria, respiratory control is a well-accepted index of function and is reported by the increase in oxygen consumption after addition of ADP. Respiratory control is most often reported as a ratio, respiratory control ratio (RCR), of maximal capacity and respiration in the absence of substrate or upon inhibition of ATP synthesis. Analogous measures of respiratory control in intact cells require the use of mitochondrial uncouplers because ADP cannot readily cross the cell membrane. A common approach is to assess maximal oxygen consumption rate (Max-OCR) is with the addition of carbonyl cyanide-4-(trifluoromethoxy)phenylhydrazone (FCCP) to induce maximal uncoupled respiration. Spare respiratory capacity (SRC) is defined by the difference between basal and maximal respiration in whole cells. Respirometry of Isolated Muscle Mitochondria.

5 μg of mitochondria were placed in each well of a 24-well Seahorse™ microplate. Measurements were performed for each subject in triplicate or quadruplicate. Microplates were centrifuged (Eppendorf Centrifuge 5804 R rotor A-2-DWP) at 4° C. for 21 minutes at 1000×g to promote attachment of mitochondria.

A bioenergetic profile for isolated skeletal muscle mitochondria is determined based on the following measurements: 1) state 2—oxygen consumption in the absence of substrate (ADP); 2) state 3—oxygen consumption in presence of saturating ADP; state 4o—oxygen consumption independent of AT generation (leak); and state 3u—uncoupled maximal oxygen consumption as summarized in FIG. 2. In brief, the Seahorse™ Analyzer was used to make the measurements as follows. All experiments were initiated with succinate (10 mM) and rotenone (2 μM). State 2 respiration is measured prior to addition of ADP (2 mM) to induce state 3 respiration with saturating amount of substrate. This is followed by oligomycin (2 μM) addition to induce state 4o respiration. The primary outcome for these measures is respiratory control ratios (RCR), calculated as state 3/state 4o. (Rogers et al., *PLos One* 6(7):e21746 (2011).) This measure can account for slight variations between mitochondrial sample preparations and experimental runs. To ensure the quality of the final mitochondrial sample, samples with RCR values <3 were omitted from analysis and enrichment of VDAC1 (Voltage-Dependent Anion Channel 1) expression is verified by Western blot analysis at the end of each experiment.
Respirometry of Circulating Blood Cells, Including PBMCs.

PBMCs were washed with phosphate-buffered saline and resuspended in the Seahorse XF™ assay buffer (pH 7.4) containing 1 mM sodium pyruvate and 11 mM D-glucose. 500,000 cells were plated per well of the 24-well Seahorse™ microplate. Measurements were performed for each subject in triplicate or quadruplicate. Microplates were centrifuged (Eppendorf Centrifuge 5804 R rotor A-2-DWP) at room temperature for 16 minutes at 1000×g to promote attachment of the cells. Plates are optionally coated with poly-D-lysine to promote cell attachment.

A bioenergetic profile for circulating blood cells is determined based on the following measurements: (1) basal oxygen consumption rate (Basal OCR), (2) maximal oxygen consumption rate (Max OCR), (3) spare respiratory capacity (SRC), and efficiency (proton leak), as summarized in FIG. 1. This assessment is adapted from the Seahorse Bioscience® Mitochondrial Stress Test and allows measurement of various aspects of cellular respiration that contribute to the overall respiratory capacity.

In brief, the Seahorse™ Analyzer was used to make the measurements as follows. Basal OCR is measured with standardized fuel conditions-1 mM sodium pyruvate and 11 mM D-glucose. Then (A) oligomycin (750 nM) will be added to block ATP synthase (complex 5), resulting in ATP-coupled respiration. The decrease in oxygen consumption reflects the amount of oxygen consumed to fuel the conversion of ADP to ATP. Next, (B) FCCP (carbonylcyanide-p-trifluoromethoxyphenylhydrazone) (1 μM), a potent mitochondrial uncoupler, will be added to uncouple mitochondria and induce maximal oxygen consumption (Max-OCR). The resultant increase in oxygen consumption represents the Max OCR of the electron transport chain. SRC is calculated as the difference between Max OCR and the Basal OCR. Finally, (C) a combination of antimycin-A and rotenone (both 1 μM) will be added to completely block mitochondrial activity. Any residual respiration is due to non-mitochondrial sources. By subtracting this residual oxygen consumption rate from the rate left after the blockage of ATP synthase by oligomycin, a measurement of oxygen consumption that is not linked to ATP synthesis can be obtained (protein leak). All measurements will be normalized to cell number, protein content, and mitochondrial mass. This analysis is referred to as a mitochondrial stress test (Seahorse Biosciences®). The basis for these measures are adapted from methods first described by Chance in 1955 and currently accepted as the gold standard for profiling mitochondrial function. (Brand and Nicholls, *Biochem. J.* 435(2):291 (2011); Chance and Williams, *Nature* 176 (4475):250 (1955); Chance and Williams, *Nature* 175 (4469):1120 (1955); Rogers et al., *PLoS One* 6(7):e21746 (2011).)

Example 3

Objective.

The following experiment was conducted to determine whether measurements of PBMC respirometry are associated with differences in muscle mitochondrial bioenergetics.
Primate Samples.

Fresh muscle tissue (vastus lateralis) and whole blood was collected from necropsies of five non-human primates (NHPs) of the *Macaca fascicularis* species as described in Example 1. The age of the subjects ranged from 16 to 26 years, which corresponds to human adults aged about 60-80 years.

Human Samples.

Fresh biopsies of skeletal muscle (vastus lateralis) were obtained from 14 human subjects. Blood samples were also taken just prior to biopsy. Subjects (participants in clinical trial; R01 AG020583) were 65-79 years old, had a Body Mass Index (BMI) of 27-34.8 kg/m$^2$, and were free from contraindications that may inhibit participation in diet and exercise interventions.

Respirometry.

Respirometry analysis was performed on the samples as described in Example 2.

Statistical Analysis.

Pearson Correlation coefficients and partial correlations were used to examine the relationship between the dependent and independent variables. P-values less than or equal to 0.05 were considered statistically significant.

Results.

With increasing age, PBMCs and mitochondria isolated from the NHPs exhibited a significant increase in the ratio of basal respiration relative to maximal respiration, indicative of a decline in bioenergetic capacity. There was a strong correlation between state 2/Basal OCR relative to Max OCR of skeletal muscle mitochondria and PBMCs (n=5, R=0.96, p=0.01). See FIG. 3A. Interestingly, both measurements reveal that increasing age leads to higher basal oxygen consumption relative to maximal respiration. This change in mitochondrial respiration underlies a loss of Spare Respiratory Capacity (SRC) of circulating cells in older primates. Previous studies report that older primates (vervets) exhibit slower walking speeds (~20%) and develop a number of age associated disorders that recapitulate human aging. (Shively et al., Age 34(5):1123 (2012).)

Similarly, PBMCs and mitochondria isolated from humans exhibited a significant increase in the ratio of basal respiration relative to maximal respiration with increasing age, and there was a strong correlation between the oxygen consumption profiles of skeletal muscle mitochondria and PBMCs (n=14, R=0.58, p=0.03). See FIG. 3B.

Example 4

Gait speed integrates the effects of multiple subsystems including the central nervous system, peripheral nervous system, perception, muscle, bone/joint, and energy production/delivery. It has been demonstrated to be predictive of future disability, cognitive deficits, institutionalization, falls, and mortality and is an important predictor of overall physical health and functional capacity and a key endpoint in clinical aging research. (Studenski et al., *JAMA* 305(1): 50-58 (2011); Abellan et al., *J Nutr. Health Aging* 13(10): 881-889 (2009).)

Despite well-established health consequences associated with slow gait speed, little is known about its physiological determinants. Mitochondria are responsible for the majority of energy production in the body, specifically from oxidative phosphorylation (OXPHOS). Aging is associated with declining mitochondrial bioenergetic capacity. (Trounce et al., *Lancet* 1(8639):637-639 (1989).) However, the role of mitochondrial function in overall health and physical ability, including gait speed, is unclear. Reliable assessments of mitochondrial function have the potential to inform on the role of bioenergetics in diminishing physical ability and may provide an objective way to monitor healthy aging.

Objective.

The following experiment was conducted to:

(1) determine whether the RCR of mitochondria isolated from leg skeletal muscle correlates with gait speed;

(2) investigate whether bioenergetic capacity (Max-OCR, Basal-OCR, and SRC) measured from peripheral blood mononuclear cells (PBMCs) could similarly predict differences in gait speed, composite physical ability (Short Physical Performance Battery Score), upper and lower body strength (grip strength and knee extensor strength), and muscle mass and quality; and (3) determine the relationship of PBMC respiratory capacity and cytokine IL-6, a proinflammatory cytokine that increases with age and is related to physical function and an array of geriatric syndromes and chronic diseases.

Subjects.

Three subsets of participants were included in this study of older (65-79 years), overweight and obese (body mass index (BMI)>28-35 kg/m$^2$), sedentary men and women recruited to participate in a clinical trial of resistance training with or without dietary-induced weight loss. Demographic data are presented in Table 1. The first subset (Cohort A) provided data indicating the relationship of skeletal muscle bioenergetics and gait speed. The second subset (Cohort B) provided data on the relationship of PBMC respirometric profiles and gait speed. Finally, the third subset (Cohort C) provided data on the relationship of PBMC respirometry with SPPB score, leg strength, grip strength, muscle quality, and inflammatory status. All subjects were community-dwelling (not in assisted living or nursing homes). The assessments reported here were conducted at baseline, prior to intervention. Eligible participants were in good health and had normal cognitive function, used no walking aids, and did not have insulin resistance, uncontrolled diabetes (Fast Blood Sugar >140 mg/dL), uncontrolled hypertension (BP>180/100 mmHg), abnormal liver or kidney function or test results, heart disease; past or current cardiovascular disease; past or current respiratory disease; past or current clinical diagnoses of neurological or hematological disease, cancer requiring treatment in the past 2 years, clinically evident edema or anemia, or substance abuse (nicotine within 1 year, drug, alcohol). The study was approved by the Wake Forest School of Medicine Institutional Review Board and all participants provided written, informed consent.

Samples and Respirometry.

Muscle biopsies (leg skeletal muscle; vastus lateralis) and whole blood samples were obtained as described above in Example 1. Respirometry analysis was performed on the samples as described in Example 2. Samples were assessed in quadruplicate.

Gait Speed.

Gait speed, calculated as meters/second, was measured using a 400-meter test. Participants were instructed to walk the 400 m distance (on a flat indoor surface 20 m in length) as quickly as possible. Encouragement was given in a standardized fashion. The test has excellent reproducibility (ICC=0.95) and directly correlates with measured maximal aerobic fitness 8.

Expanded Short Physical Performance Battery (Ex-SPPB).

The expanded SPPB (Ex-SPPB) provides a composite score indicative of physical ability and was used to prevent ceiling effects when applying the measure to well-functioning, community-dwelling older adults. (Simonsick et al., *J. Amer. Geriatric Soc.* 49:1544-1548 (2001)). Briefly, the Ex-SPPB consists of a usual gait speed test, a usual gait speed test using a narrow course (20 cm), 5 repeated chair stands, and 30 sec standing balance tests (semi- and full-tandem and single leg). Scores and times are recorded for each and converted to ratios and summed to get a composite score on a continuous scale ranging from 0 to 4.

Peak Knee Extensor (KE) Strength.

Peak knee extensor strength was used as an indicator of leg strength. Peak knee extensor (KE) strength in Newton meters (Nm) was measured on a Biodex System 4 dynamometer (Biodex Medical Systems, Inc., Shirley, NY) at 60° per second with the participant seated and the hips and knees flexed at 90°. To stabilize the hip joint and the trunk, participants were restrained with straps at the chest, hip and thigh. Seat height and depth, and the position of the lever arm ankle pad were adjusted to accommodate each participant. Participants were asked to extend the knee and push as hard as possible against the ankle pad. Strength of the right leg recorded as peak torque was used for analyses.

Grip Strength.

Grip strength was used as an objective measure of upper body extremity strength and was measured using a dynamometer. Grip strength was measured twice on each hand to the nearest kg using an isometric Hydraulic Hand Dynamometer (Jamar, Bolingbrook, IL.) and the maximal value from both hands was used in analyses. Output was reported as kilograms.

Leg Lean Mass and Muscle Quantity.

Leg lean mass was measured by dual energy X-ray absorptiometry (DXA System, Hologic Delphi QDR, Bedford, MA). Muscle quality was calculated as the ratio of knee extensor peak torque to lean mass of the right leg assessed by DXA (Nm/kg leg lean mass).

Interleukin-6 Quantification.

Blood from 12-hour fasted subjects was collected, processed, divided into aliquots, stored at −80° C., and analyzed according to previously published methods.[18] Briefly, high-sensitivity IL-6 assays were run using Quantikine® Colorimetric ELISA kits from R&D systems (Minneapolis, MN.). All samples were measured in duplicate, and the average of the two values was used for data analyses.

Statistical Analysis.

Pearson correlation coefficients and partial correlations (adjusting for age, BMI, or gender) were calculated using SPSS v.21 (Armonk, NY) to examine relationships between the dependent variable (gait speed) and the independent variables (maximal respiration, SRC, and RCR). p-values of <0.05 were considered statistically significant.

Results.

The demographics and bioenergetic data for each study subset are summarized in Table 1. Participants in both groups were of a similar age, gender distribution, and obesity status. Respiratory capacity was measured in isolated muscle mitochondria of one subset and isolated PBMCs of the other subset, and the measurements were then assessed in comparison to gait speed.

TABLE 1

| Demographics and respirometry of study participants. | | |
|---|---|---|
| Cohort A: Skeletal Muscle Mitochondrial Bioenergetics and Gait Speed n = 17 % Female 41% | | |
| | Mean ± SD | Range |
| Age (years) | 69.7 ± 3.96 | 65-78 |
| BMI (kg/m²) | 31.1 ± 2.41 | 27.2-35.00 |
| Walk Speed (m/s) | 1.51 ± 0.20 | 1.06-1.84 |
| Respiratory Control Ratio | 4.9 ± 1.72 | 3.15-8.36 |
| State 3 OCR (picomoles/min/5 µg) | 427.3 ± 151.63 | 170.41-751.80 |
| State 4o OCR (picomoles/min/5 µg) | 96.2 ± 44.32 | 20.39-179.70 |
| Cohort B: PBMC Respirometry and Gait Speed n = 17 % Female 41% | | |
| | Mean ± SD | Range |
| Age (years) | 68.4 ± 3.41 | 65-78 |
| BMI (kg/m²) | 30.7 ± 2.33 | 27.2-35.00 |
| Walk Speed (m/s) | 1.51 ± 0.20 | 1.06-1.84 |
| Respiratory Control Ratio | 4.9 ± 1.72 | 3.15-8.36 |
| State 3 OCR (picomoles/min/5 µg) | 427.3 ± 151.63 | 170.41-751.80 |
| State 4o OCR (picomoles/min/5 µg) | 96.2 ± 44.32 | 20.39-179.70 |

| Cohort C: PBMC Respirometry and SPPB Score, Leg Strength, Grip Strength, Muscle Quality, and Inflammatory Status % Female 40% | | | |
|---|---|---|---|
| | N | Mean ± SD | Range |
| Age (years) | 15 | 68.3 ± 3.45 | 65-78 |
| BMI (kg/m²) | 15 | 30.8 ± 2.44 | 27.0-34.9 |
| Walk Speed (m/s) | 15 | 1.5 ± 0.20 | 1.1-1.8 |
| Expanded Short Physical Performance Battery | 15 | 2.5 ± 0.26 | 2.1-2.9 |
| Knee Extensor Strength (Nm) | 15 | 57.9 ± 35.96 | 57.9-179.5 |
| Leg Lean Mass (Kg) | 15 | 8.3 ± 1.58 | 6.4-11.1 |
| Muscle Quality (Nm/Kg) | 15 | 12.4 ± 2.49 | 7.6-17.3 |

TABLE 1-continued

| Demographics and respirometry of study participants. | | | |
|---|---|---|---|
| Grip Strength (Kg) | 15 | 35.6 ± 10.69 | 20.0-52.0 |
| Interleukin-6 Level (pg/mL) | 15 | 2.2 ± 0.76 | 1.3-3.5 |
| Monocyte Cell Count (per mL whole blood) | 15 | 486666.7 ± 155226.41 | 300000-900000 |
| Lymphocyte Cell Count (per mL whole blood) | 15 | 182666.7 ± 563745.97 | 500000-2600000 |
| Basal OCR (pmol/min/500,000 cells) | 15 | 146.3 ± 51.26 | 59.7-256.1 |
| Maximal OCR (pmol/min/500,000 cells) | 15 | 573.212.01 | 285.5-980.2 |
| Spare Respiratory Capacity (pmol/min/500,000 cells) | 15 | 426.8 ± 167.81 | 183.7-779.2 |

Based on the established role of mitochondrial bioenergetics in muscle function, we investigated whether the measurements of leg skeletal muscle mitochondrial function would be associated with differences in gait speed. In order to test this hypothesis, we compared the RCR of skeletal muscle mitochondria with gait speed as shown in FIG. 4. The results show that individuals with a faster gait speed had a higher RCR (r=0.536, p=0.027). This association remained significant after adjusting for age (r=0.586, p=0.017), BMI (r=0.539, p=0.031), and gender (r=0.514, p=0.042).

Based on the findings that PBMC and muscle mitochondria respirometric profiles are associated with one another in both NHP and humans, as shown in Example 3, it was assessed whether gait speed is correlated with the respiratory capacity of PBMCs. Gait speed was plotted against SRC (picomoles/min/500,000 cells) (FIG. 5A), Max-OCR (picomoles/min/500,000 cells) (FIG. 5B), and basal OCR (picomoles/min/500,000 cells) (FIG. 5C) of PBMCs. Participants with faster gait speeds had higher Max-OCR (r=0.585, p=0.014) and higher SRC (r=0.609, p=0.009). The association of gait speed and basal-OCR did not reach significance (r=0.425, p=0.089) suggesting that Max-OCR was primarily responsible for increased SRC in individuals with faster gait speed. The associations of gait speed to Max-OCR and SRC remained significant when controlling for age (r=0.573, p=0.020; r=0.598, p=0.015, respectively), BMI (r=0.585, p=0.017; r=0.612, p=0.012, respectively), and gender (r=0.505, p=0.046; r=0.538, p=0.032, respectively). The associations of gait speed to Basal-OCR changed marginally after controlling for age (r=0.416, p=0.109), BMI (r=0.427, p=0.099), or gender (r=0.328, p=0.216). Thus, this blood-based assay provides results predictive of clinically measured physical ability.

Ex-SPPB was plotted against SRC (pmol/min/500,000 cells), maximal respiration (pmol/min/500,000 cells), and basal respiration (pmol/min/500,000 cells) as shown in FIGS. 6A-6C. Higher SRC and maximal respiration were associated with greater Ex-SPPB scores. Correlations between SRC, maximal respiration, and basal respiration with Ex-SPPB are summarized in Table 2. Positive correlations between SRC and maximal respiration with Ex-SPPB remained significant after independent adjustments for age, sex, and BMI (presented in Table 2).

TABLE 2

| Statistical analysis of expanded SPPB compared to PBMC bioenergetics. | | | | | | |
|---|---|---|---|---|---|---|
| | SRC | | Max | | Basal | |
| Correlation | r | p-value | r | p-value | r | p-value |
| Pearson | 0.59 | 0.02 | 0.58 | 0.02 | 0.5 | 0.06 |
| Partial/Age | 0.59 | 0.02 | 0.59 | 0.02 | 0.5 | 0.07 |

TABLE 2-continued

| Statistical analysis of expanded SPPB compared to PBMC bioenergetics. | | | | | | |
|---|---|---|---|---|---|---|
| | SRC | | Max | | Basal | |
| Correlation | r | p-value | r | p-value | r | p-value |
| Partial/Gender | 0.55 | 0.04 | 0.55 | 0.04 | 0.46 | 0.10 |
| Partial/BMI | 0.59 | 0.02 | 0.59 | 0.03 | 0.49 | 0.07 |
| Partial/IL-6 | 0.55 | 0.04 | 0.63 | 0.04 | 0.57 | 0.07 |

Peak KE strength (Nm) was plotted against SRC, maximal respiration, and basal respiration as shown in FIGS. 7A-7C. These results are summarized in Table 3. Higher SRC and maximal respiration were associated with greater peak KE strength. Positive correlations between SRC and maximal respiration remained significant after independent adjustments for age, sex, and BMI (Table 2). The positive association between basal respiration and peak KE strength also reached statistical significance when adjusting for sex.

TABLE 3

| Statistical analysis of peak knee extensor strength compared to PBMC bioenergetics. | | | | | | |
|---|---|---|---|---|---|---|
| | SRC | | Max | | Basal | |
| Correlation | r | p-value | r | p-value | r | p-value |
| Pearson | 0.60 | 0.03 | 0.60 | 0.03 | 0.50 | 0.08 |
| Partial/Age | 0.59 | 0.04 | 0.59 | 0.04 | 0.49 | 0.10 |
| Partial/Gender | 0.70 | 0.01 | 0.69 | 0.01 | 0.58 | 0.05 |
| Partial/BMI | 0.59 | 0.04 | 0.60 | 0.04 | 0.53 | 0.07 |
| Partial/IL-6 | 0.55 | 0.08 | 0.56 | 0.08 | 0.50 | 0.11 |

Grip strength (kg) was plotted against SRC, maximal respiration, and basal respiration as shown in FIGS. 8A-8C. These results are summarized in Table 4. Higher SRC and maximal respiration were associated with greater grip strength. These associations remained significant after independent adjustments for age and BMI. When adjusting for sex, SRC remained significantly positively associated with grip strength and the correlation between maximal respiration and grip strength had a trend toward significance.

TABLE 4

| Statistical analysis of grip strength compared to PBMC bioenergetics. | | | | | | |
|---|---|---|---|---|---|---|
| | SRC | | Max | | Basal | |
| Correlation | r | p-value | r | p-value | r | p-value |
| Pearson | 0.54 | 0.04 | 0.52 | 0.05 | 0.40 | 0.13 |
| Partial/Age | 0.59 | 0.04 | 0.59 | 0.04 | 0.49 | 0.10 |
| Partial/Gender | 0.53 | 0.05 | 0.51 | 0.06 | 0.35 | 0.21 |
| Partial/BMI | 0.57 | 0.03 | 0.57 | 0.03 | 0.52 | 0.06 |
| Partial/IL-6 | 0.54 | 0.08 | 0.54 | 0.09 | 0.45 | 0.17 |

Leg lean mass (kg) was plotted against SRC, maximal respiration, and basal respiration as shown in FIGS. 9A-9C. These results are summarized in Table 5. There were no significant correlations between leg lean mass and PBMC bioenergetic parameters.

TABLE 5

| Statistical analysis of leg lean mass compared to PBMC bioenergetics. | | | | | | |
|---|---|---|---|---|---|---|
| | SRC | | Max | | Basal | |
| Correlation | r | p-value | r | p-value | r | p-value |
| Pearson | 0.23 | 0.42 | 0.18 | 0.53 | −0.02 | 0.96 |
| Partial/Age | 0.18 | 0.55 | 0.13 | 0.68 | −0.07 | 0.82 |
| Partial/Gender | 0.29 | 0.34 | 0.23 | 0.46 | 0.01 | 0.98 |
| Partial/BMI | 0.20 | 0.51 | 0.17 | 0.57 | 0.05 | 0.86 |
| Partial/IL-6 | 0 | 0.99 | −0.03 | 0.92 | −0.12 | 0.72 |

Muscle quality (Nm/kg) was plotted against SRC, maximal respiration, and basal respiration as shown in FIGS. 10A-10C. These results are summarized in Table 6 and show a significant positive association between muscle quality and SRC, as well as a trend for a significant association between muscle quality and maximal respiration. The significant association between muscle quality and SRC as well as the trend for significance between muscle quality and maximal respiration remained after independently adjusting for BMI. The associations were no longer statistically significant after adjusting for age and sex; however, a trend toward a statistically significant p-value remained. These data indicate that PBMC respirometry is related to muscle quality, rather than muscle mass. This finding is significant because loss of muscle quality precedes loss of muscle mass in the development of sarcopenia. These data support the utility of PBMC respirometry in the prediction of age-related functional decline.

TABLE 6

| Statistical analysis of leg muscle quality compared to PBMC bioenergetics. | | | | | | |
|---|---|---|---|---|---|---|
| | SRC | | Max | | Basal | |
| Correlation | r | p-value | r | p-value | r | p-value |
| Pearson | 0.56 | 0.04 | 0.51 | 0.06 | 0.29 | 0.31 |
| Partial/Age | 0.54 | 0.06 | 0.48 | 0.10 | 0.23 | 0.45 |
| Partial/Gender | 0.49 | 0.09 | 0.44 | 0.13 | 0.21 | 0.48 |
| Partial/BMI | 0.55 | 0.05 | 0.52 | 0.07 | 0.33 | 0.26 |
| Partial/IL-6 | 0.5 | 0.12 | 0.47 | 0.14 | 0.33 | 0.32 |

Plasma level of IL-6 was plotted against SRC, maximal respiration, and basal respiration as shown in FIGS. 11A-11C. These results are summarized in Table 7 and show a statistically significant negative correlation, indicating that greater levels of IL-6 were associated with reduced bioenergetic function. These associations remained statistically significant when independently adjusting for age and sex. When adjusted for BMI, only the association between basal respiration and plasma IL-6 remained significant; however the p-values for correlations between SRC and maximal respiration and IL-6 level had trends toward statistical significance. These results suggest a relationship between systemic inflammatory status and systemic mitochondrial bioenergetic function measured in peripheral blood cells.

TABLE 7

| Statistical analysis of plasma IL-6 compared to PBMC bioenergetics. | | | | | | |
|---|---|---|---|---|---|---|
| | SRC | | Max | | Basal | |
| Correlation | r | p-value | r | p-value | r | p-value |
| Pearson | −0.55 | 0.05 | −0.58 | 0.04 | −0.61 | 0.03 |
| Partial/Age | −0.61 | 0.03 | −0.64 | 0.03 | −0.63 | 0.03 |
| Partial/Gender | −0.60 | 0.04 | −0.65 | 0.02 | −0.69 | 0.01 |
| Partial/BMI | −0.53 | 0.08 | −0.56 | 0.06 | −0.59 | 0.04 |

Further assessment was also conducted looking at PBMC population subsets. PBMCs are comprised of multiple blood cell types, primarily monocytes and lymphocytes. The relative number of these cell types can differ between individuals and can change depending on inflammatory status. In order to determine the role of PBMC composition on the respiratory capacity of PBMCs, the relationship of PBMC respirometry with complete blood count (CBC) measures of monocytes and lymphocytes was examined using the patient samples described in Example 3.

Figure 13:
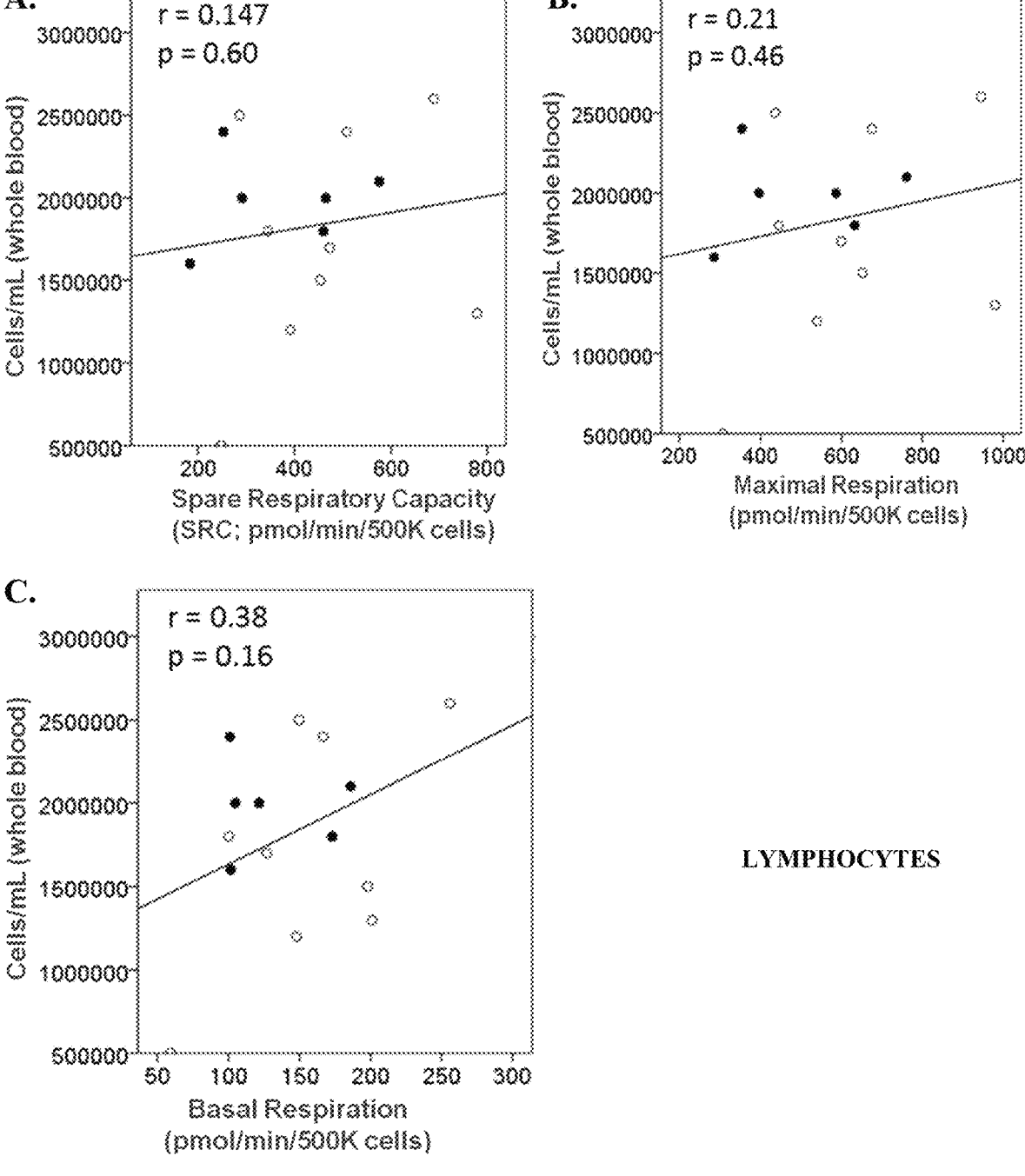
FIG. 13 depicts the respirometric profiles of lymphocytes measured as SRC (A), Max-OCR (B), and basal-OCR (C) according to certain aspects. Gender is indicated as black circles denoting female subjects and white circles denoting male subjects.

Monocyte cell count (cells/mL whole blood) was plotted against SRC, maximal respiration, and basal respiration in FIGS. 12A-12C, and lymphocyte cell count (cells/mL whole blood) was plotted against SRC, maximal respiration, and basal respiration in FIGS. 13A-13C. The results show no significant associations between monocyte or lymphocyte cell counts and SRC, maximal respiration, or basal respiration, indicating that the absolute number of lymphocytes or monocytes was not associated with bioenergetic function measured in PBMCs.

The findings of this study indicate that, in a cohort of well-functioning, overweight/obese community-dwelling older adults aged 65 to 78 years, without overt aging-related disease, higher maximal respiration and SRC of PBMCs were associated with better Ex-SPPB, greater peak KE strength, grip strength, greater leg muscle quality, and lower plasma IL-6 level. Thus, physical ability, measured as walking speed (as well as composite physical ability and upper and lower body strength), and the bioenergetic capacity of PBMCs, measured as spare respiratory capacity, basal capacity, and maximal capacity, are highly correlated. This is the first instance in which a relationship has been established between bioenergetic capacity—in PBMCs or muscle cell mitochondria—and mortality and morbidity (due to the correlation of mortality and morbidity and walking speed). For example, in contrast, a recent study did not find a relationship between PBMC respiration and vitality in middle-aged men, as measured by the Medical Outcomes Study Short Form (MOSSF) vitality scale. (Maynard et al., *Aging (Albany NY)* 5(11):850-864 (2013).) The recent study used survey tools to measure self-reported vitality. This is distinctly different from objective measures of gait speed which directly report on physical ability. Compared to other measures of physical health, including survey based tools, gait speed measurements are the strongest predictors of survival (Hardy et. al., *J. Am. Geriatr. Soc.* 55(11):1727-1734 (2007).)

The hypothesis of this study was that muscle bioenergetics is the most relevant factor for understanding mobility function. Without being limited to any particular theory, the association between mitochondrial function in both blood and muscle and gait speed may be due to either a strong association of mitochondrial function between these tissues or that muscle and PBMC mitochondrial function tap into different processes that contribute to mobility.

In addition, based on this study, minimum respiration rates observed in healthy older (>65 yr old) subjects have been calculated as set forth in Table 8. Based on these cutoffs, a SRC that is 40% of Max defines the lower respiratory capacity threshold for healthy, elderly adults. These cutoffs can be used to identify subjects that are healthy and, thus, are more likely to have good clinical outcomes, as well as subjects that are not healthy and, thus, may be expected to have poorer clinical outcomes.

TABLE 8

Minimum respiration rates in healthy, elderly adults.

|  | SRC | Max | Basal |
|---|---|---|---|
| PBMC (pmol/min/500k cells) | 100 | 250 | 150 |
| Lymphocytes (pmol/min/500k cells) | 50 | 125 | 75 |
| Monocytes (pmol/min/500k cells) | 65 | 165 | 100 |
| Platelets (pmol/min/400 μg total platelet protein) | 250 | 650 | 400 |

Example 5

The study results described in Example 4 indicate that respirometric profiles of PBMCs are related to age, physical function, and circulating factors, such as inflammatory cytokines, known to increase with age and systemically alter mitochondrial function. The purpose of this study is to assess whether improvement of bioenergetic capacity with cardiac rehabilitation (CR) is related to age and is associated with the degree of physical function improvement. The specific aims of the study are to determine:

1) whether bioenergetic capacity is independently associated with middle and older age, and baseline physical ability;
2) whether changes in bioenergetic capacity in response to CR are associated with changes in physical ability in older and middle-aged adults; and
3) the relationship between inflammatory status and bioenergetic capacity at baseline and in response to CR.

Recruitment and Assessment:

Patients that have been prescribed CR after an acute coronary event have been recruited. The role of mitochondrial bioenergetics in outcomes of the standard 3-month aerobic exercise-based program in older (>70 yrs) is being compared to outcomes for middle-aged (45-55 years) adults. The same subject exclusion factors used for Example 4 are being used. Bioenergetic profiles, physical ability (Short Physical Performance Battery (SPPB), gait speed, fatigue, strength), cardiorespiratory fitness (MET level, peak $VO_2$) and inflammatory status, are being measured before and after CR. Spare respiratory capacity (SRC) of circulating cells is the predetermined primary readout of bioenergetic capacity in this study. Secondary outcomes assessed include leg power (measured using a Nottingham power rig), grip strength (measured as described in Example 4), gait speed (measured as described in Example 4), fatigue (based on gait speed analysis; decline in lap time between the second and last 50 meter segment); peak exercise VO2 (expired gases will be measured with a MedGraphics Ultima® system; modified Nauhton protocol; participants will be asked to give maximal effort confirmed objectively by a respiratory exchange ratio >1.05, a rate of perceived exertion >18, or a >90% age-predicted maximal heart rate), mobility and disability (self-report; Short Form Mobility Assessment Tool (MAT-SF) used to show tasks); and patient-centered outcomes (self-determined).

Personalize exercise regimens were developed for each patient based on medical history (comorbidities, medications), metabolic equivalent (MET) level, height, weight, waist circumference, blood lipid profile (LDL, HDL, triglycerides), blood pressure, heart rate, cognition (assessed using the Mini-Mental State Exam, physical performance (6 minute walk distance, 6 mwd), and questionnaires relating to their personal goals and quality of life (Ferrans-Powers QOL). Assessments will be done during 4 visits: 1 screening+$1^{st}$ baseline, $2^{nd}$ baseline, and 2 post CR. The $2^{nd}$ baseline visit will occur in the morning after a 12-hour fast. Blood will be collected in the G-CRU for analyses of mitochondrial function. Participants will then eat breakfast (yogurt, juice, and a selection of baked items) and have at least 1hr to rest before beginning exercise testing (SPPB, leg power, grip strength, and maximal VO2 treadmill test). Follow-up visits will be performed in a similar manner.

Analytics:

Bioenergetic profiles of PBMCs will be determined as described above in Example 4. SRC will be calculated by subtracting Basal-OCR from Max-OCR. Expanded SPPB assessment and assessment of IL-6 expression will also be performed as described above in Example 4.

MtDNA copy number and citrate synthase activity (CSA) have been associated with aging, age-related disorders, and mortality; and are likely contributors to cellular bioenergetic capacity. CSA will be quantified using commercially available kits (Sigma, St. Louis, MO). mtDNA copy number will be quantified by qPCR as described by Phillips et al., *Sci. Rep.* 4:3887 (2014). The association of these readouts with bioenergetic capacity, age, physical function and CR response will be analyzed.

Conventional Statistical Analyses:

Descriptive statistic and visualization methods (e.g., scatterplot) are used to characterize the association between bioenergetic capacity and age and physical ability at baseline. T-tests are used to test for differences by age group and bivariate correlation between bioenergetics and continuous variables will be tested for significance. To assess whether bioenergetic capacity changes in response to CR are associated with changes in physical ability, data collected using a pre-post test design is used with the linear model $\Delta PF = \beta_0 + \beta_1 \Delta BE + \beta_2 PFBL$ $\beta_3 Age + \beta_4 Age \times \Delta BE + other$ covariates+$\varepsilon$, where $\Delta PF$ denotes the change in pre-post CR physical function, as measured by ex-SPPB, $\Delta BE$ denotes the change in bioenergetic capacity, as measured by SRC, and $\varepsilon$ denotes an error term of zero mean and unknown variance. The moderation effect of Age on $\Delta BE$, as indicated by the interaction term, is included if the individual variables are significant. A significant interaction could explain the high level of heterogeneity of CR treatment. Other covariates include gender and BMI. Secondary analysis will examine each age group separately and will include actual age as a covariate in the model, replacing age group assignment.

Secondary T-tests can also be used to compare the change in bioenergetic capacity between CR responders and non-responders using a 10% change in exSPPB as the cutoff. For assessing inflammatory status relationships, a bivariate analysis is used to examine the association between inflammatory markers and bioenergetic capacity. To study change in response to CR, regression analyses are used similar to that above but with PF replaced by the inflammatory marker measure.

Power Analysis:

Power is based on tests assessing inflammatory status relationships with ΔBE as the primary explanatory variable. No R-square value is available for covariates for ΔPF. Assuming that the other covariates explain 30% variance (R-square=0.3), n=100 (after an estimated 10% dropout) can detect a change of 0.05 in R-square due to ΔPE with 80% power. If R-square for the other covariates is 0.5 (high level), then power for the same effect increases to 90%. On the other hand, if R-square is 0.1(low level), which we believe is unlikely, then power drops to 67%.

Predicted Results:

Bioenergetic capacity of PBMCs (SRC) is predicted to generally be greater in middle aged adults as compared to older adults and generally be greater in subjects with greater baseline physical ability. Bioenergetic capacity of PBMCs (SRC) is predicted to improve in response to the two week CR program and is predicted to correlate with improved physical ability. Inflammatory status, as reflected by IL-6 expression, is predicted to increase in subjects with lower bioenergetic and/or physical ability and negatively correlate with bioenergetic capacity of PBMCs (SRC).

Example 6

An ongoing study is assessing PBMC respiratory capacity in conjunction with patient response to a two week aerobic exercise program consisting of 8 bouts of treadmill walking (30 min each bout). The subject cohort studied is similar to that described in Examples 4 and 5 for healthy, elderly adults (including exclusion factors).

Figure 14:
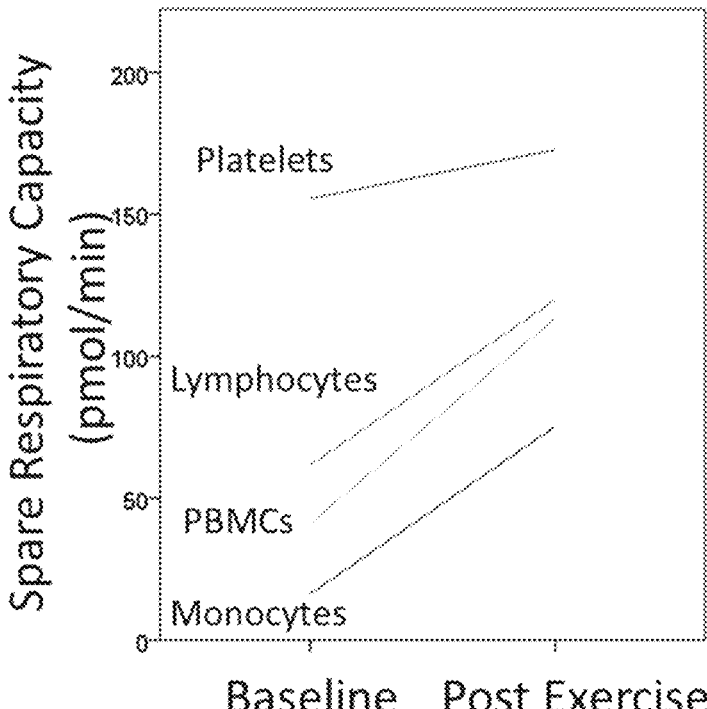
FIG. 14 depicts the respirometric profiles of PMBC, lymphocytes, monocytes, and platelets measured as SRC prior to and following a two week exercise program according to certain aspects.

Preliminary Results:

SRC, measured across multiple circulating cell types, is improved after exercise training. Exemplary data from a study participant is shown in FIG. 14.

Example 7

An ongoing study is assessing the impact of Vitamin D supplementation into patient diet and its impact on respiratory capacity. 25-hydroxyvitamin D (25(OH)D), is a pre-hormone that is produced in the liver by hydroxylation of vitamin D3. Low 25(OH)D concentrations are associated with muscle pain, weakness, and fatigue. Muscle and PBMCs respiratory capacity is being measured before and after supplementation. The main objective is to determine whether mitochondrial function, measured in both blood and muscle, is increased among individuals with insufficient 25(OH)D concentrations who are randomized to vitamin D3 supplementation. Vitamin D supplementation is provided to increase subject 25(OH)D concentrations to >30 ng/mL.

Subjects:

This study is a double-blind randomized placebo controlled trial in older (70-89 yrs) men and women with initial 25(OH)D concentrations of 10-30 ng/mL. The same subject exclusion factors used for Example 4 are being used.

Vitamin D Supplementation:

4000 IU/d of vitamin D3 for 4 months for participants with initial 25(OH)D concentrations of 10-20 ng/mL. 2000 IU/d of vitamin D3 for 4 months for participants with initial 25(OH)D concentrations of 20-30 ng/mL.

Status/Predicted Results:

Baseline measurements of respiratory capacity have been taken for an initial group of recruited subjects. The supplementation program is ongoing. It is predicted that the respiratory of circulating cells will be increased compared to baseline and related to the relative improvement of skeletal muscle mitochondrial function, and increased physical ability.

Example 8

An ongoing study is examining the ability of blood based bioenergetic profiling to assess Alzheimer's disease (AD) risk. Previous studies have indicated that multiple features of circulating cells are related to cognitive impairment and the development of AD. This study will assess which cell types and baseline bioenergetic parameters are most strongly related to cognitive status, pathophysiological processes associated with AD, mild cognitive impairment (MCI), and AD risk defined by family history in a human patient cohort. In a parallel study, a primate cohort is being studied to examine whether blood based bioenergetic profiles are related to mitochondrial function measured and brain tissue, as well as the presence of AD plaques and tangles assessed by brain imaging. For both studies, the relationship of blood cell bioenergetic capacity with known AD biomarkers will be examined. These biomarkers include plasma and CSF Aβ40 and Aβ42, CSF tau and phospho-tau, and APOE genotype.

Subjects:

Human subjects will include an equal distribution of male and female adults (55-90 yrs), with or without cognitive deficit, who will undergo blood-based bioenergetic profiling and receive cognitive performance tests and biomarker measures of AD pathology. Participants are recruited based on qualification into one of four groups as set forth in Table 9. The non-human primate studies were conducted with 18 female vervet/African green monkeys (*Chlorocebus aethiops sabaeus*) from the Vervet Research Colony of Wake Forest University. The animals fell into two groups: young adult (n=9 animals aged 8.5 to 13.7 years) and elderly adults (n=9 animals aged 19.7 to 23.6 years).

TABLE 9

| | | | Clinical | | |
|---|---|---|---|---|---|
| Group | N | Cognitive Impairment? | Dementia Rating | Family History | Glycemic Dysregulation |
| Low-Risk | 20 | No | 0 | No | No |
| High-Risk | 20 | No (subjective complaints allowed) | 0 | Yes | Mild hemoglobin Alc > 5.6%, fasting glucose > 99 mg/dL |
| MCI | 20 | Meets well-established MCI criteria | 0.5 | Either | No or Mild |
| AD | 20 | Diagnosed and MMSE ≥18 | 0.5-1 | Either | No or Mild |

AD Study Patient Selection Criteria.

Samples:

Blood samples are being collected as described in the preceding examples. For the primate study, muscle samples (skeletal muscle, cardiac muscle, and liver) were also collected at necroscopy as described in the previous examples.

Respiratory Capacity Analysis:

PBMCs respiratory capacity is being measured as Spare Respiratory Capacity in both the human group and primate group as described above in Examples 3-5.

Status/Predicted Results—Human:

Recruitment of human subjects and analysis of samples is ongoing. It is predicted that increased severity of cognitive decline will be related to the respiratory capacity of circulating cells. In addition, it is predicted that the presence of known AD biomarkers will likewise be related to the respiratory capacity of circulating cells.

Status/Predicted Results—Primate:

Sample analysis is ongoing. It is predicted that the respiratory capacity of circulating cells will be related to that of brain tissue and other tissues analyzed. Moreover, it is predicted that primate age will be related directly related to respiratory capacity measured in blood and across tissues. It is also predicted that the presence of AD biomarkers will likewise be related to the respiratory capacity of circulating cells.

All printed patents and publications referred to in this application are hereby incorporated herein in their entirety by this reference.

It should be understood that the foregoing relates to certain embodiments of the invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein may suggest themselves to those skilled in the art without departing from the spirit of the present invention and/or the scope the appended claims.

REFERENCES

1. Abellan van K G, et al. Gait speed at usual pace as a predictor of adverse outcomes in community-dwelling older people an International Academy on Nutrition and Aging (IANA) Task Force. *J Nutr Health Aging* 13(10):881-889 (2009).
2. Altmann J., "Observational study of behavior: sampling methods, Behaviour (3), 227 (1974).
3. Andreux P. A. et al., Pharmacological approaches to restore mitochondrial function, *Nat. Rev. Drug Discov.* 12(6), 465 (2013).
4. Barazzoni R. et al., Effects of aging on mitochondrial DNA copy number and cytochrome c oxidase gene expression in rat skeletal muscle, liver, and heart, *J. Biol. Chem.* (5), 3343 (2000).
5. Biino G., et al., Influence of age, sex and ethnicity on platelet count in five Italian geographic isolates: mild thrombocytopenia may be physiological, *Br. J Haematol.* 157(3):384-387 (2012).
6. Brand M D, Nicholls D G. Assessing mitochondrial dysfunction in cells. *The Biochemical Journal* 435(2): 297-312 (2011).
   Cann J. A. et al., Clinicopathologic characterization of naturally occurring diabetes mellitus in vervet monkeys, *Vet. Pathol.* 47(4):713-718 (2010).

8. Cesari M. et al., Lipoprotein peroxidation and mobility limitation: results from the Health, Aging, and Body Composition Study, *Arch. Intern. Med.* 165(18):2148-2154 (2005).
9. Chance B., Williams G. R., A method for the localization of sites for oxidative phosphorylation, *Nature* 176(4475): 250-254 (1955).
10. Chance B., Williams G. R., A simple and rapid assay of oxidative phosphorylation, Nature 175(4469): 1120-1121 (1955).
11. Choi S. J. et al., Force-Generation Capacity of Single Vastus Lateralis Muscle Fibers and Physical Function Decline With Age in African Green Vervet Monkeys, *J. Gerontol. A Biol. Sci. Med. Sci.* 68(3):258-267 (2012).
12. Coen P. M. et al., Skeletal Muscle Mitochondrial Energetics Are Associated With Maximal Aerobic Capacity and Walking Speed in Older Adults, *J. Gerontol. A Biol. Sci. Med. Sci.* 68(4):447-455 (2012).
13. Coen P. M. et al., Skeletal muscle mitochondrial energetics are associated with maximal aerobic capacity and walking speed in older adults. *J. Gerontol. A Biol. Sci. Med. Sci.* 68(4):447-455 (2013).
14. Cooper R. et al., Objective measures of physical capability and subsequent health: a systematic review, *Age Ageing* 40(1):14-23 (2011).
15. Corsonello A. et al., Prognostic significance of the short physical performance battery in older patients discharged from acute care hospitals, *Rejuvenation. Res.* 15(1):41-48 (2012).
16. Crimmins E. et al., Biomarkers related to aging in human populations, *Adv. Clin. Chem.* 46:161-216 (2008).
17. Crujeiras A. B. et al., Differential expression of oxidative stress and inflammation related genes in peripheral blood mononuclear cells in response to a low-calorie diet: a nutrigenomics study, *OMICS* 12(4): 251-261 (2008).
18. Daly M. E., Determinants of platelet count in humans, Haematologica 96(1):10-13 (2011).
19. Desborough J. P., The stress response to trauma and surgery, *Br. J. Anaesth.* 85(1):109-117 (2000).
20. Era P., Heikkinen E., Postural sway during standing and unexpected disturbance of balance in random samples of men of different ages, *J Gerontol.* 40(3): 287-295 (1985).
21. Feng X. et al., Myosin heavy chain isoform expression in the Vastus Lateralis muscle of aging African green vervet monkeys, *Exp. Gerontol.* 47(8):601-607 (2012).
22. Ferrucci L. et al. Subsystems contributing to the decline in ability to walk: bridging the gap between epidemiology and geriatric practice in the InCHIANTI study. *J Am Geriatr Soc.* 48(12):1618-1625 (2000).
23. Fink B. D. et al., Endothelial cell and platelet bioenergetics: effect of glucose and nutrient composition, *PLoS One* 7(6):e39430 (2012).
24. Gabriel K K P et al., Test-retest reliability and validity of the 400-meter walk test in healthy, middle-aged women. *J Phys Act Health* 7(5):649-657 (2010).
25. Guralnik J. M. et al., Lower extremity function and subsequent disability: consistency across studies, predictive models, and value of gait speed alone compared with the short physical performance battery, *J Gerontol. A Biol. Sci. Med. Sci.* 55(4), M221-M231 (2000).
26. Guralnik J. M., Winograd C. H., Physical performance measures in the assessment of older persons, *Aging (Milano)* 6(5):303-305 (1994).

27. Hansford R G, Chappell J B. The effect of Ca$^{2+}$ on the oxidation of glycerol phosphate by blowfly flight-muscle mitochondria. *Biochem Biophys Res Commun* 27(6):686-692 (1967).

28. Hardy S. E. et al., Ability to walk ¼ mile predicts subsequent disability, mortality, and health care costs, *J Gen. Intern. Med.* 26(2):130-135 (2011).

29. Hardy S. E. et al., Improvement in usual gait speed predicts better survival in older adults, *Am. Geriatr. Soc.* 55(11):1727-1132 (2007).

30. Hearps A. C. et al., Aging is associated with chronic innate immune activation and dysregulation of mono-cyte phenotype and function, *Aging Cell* 11(5):867-875 (2012).

31. Hill G. et al., Regulation of vascular smooth muscle cell bioenergetic function by protein glutathiolation, *Biochim. Biophys. Acta* 1797(2):285-295 (2010).

32. Jayachandran M. et al., Platelet characteristics change with aging: role of estrogen receptor beta, *J Gerontol. A Biol. Sci. Med. Sci.* 60(7):815-819 (2005).

33. Jayachandran M. et al., Loss of estrogen receptor beta decreases mitochondrial energetic potential and increases thrombogenicity of platelets in aged female mice, *Age (Dordr)* 32(1):109-121 (2010).

34. Joseph A. M. et al. The impact of aging on mitochondrial function and biogenesis pathways in skeletal muscle of sedentary high- and low-functioning elderly individuals. *Aging Cell* 11(5):801-809 (2012).

35. Kayo T. et al., Influences of aging and caloric restriction on the transcriptional profile of skeletal muscle from rhesus monkeys. *Proc Natl Acad Sci USA* 98(9): 5093-5098 (2001).

36. Leng S. X. et al., Associations of neutrophil and monocyte counts with frailty in community-dwelling disabled older women: results from the Women's Health and Aging Studies I, *Exp. Gerontol.* 44(8):511-516 (2009).

37. Levine M. E., Modeling the Rate of Senescence: Can Estimated Biological Age Predict Mortality More Accurately Than Chronological Age? *J. Gerontol. A Biol. Sci. Med. Sci.* 68(6):667-674 (2012).

38. Lowell B., Shulman, G. I., Mitochondrial dysfunction and type 2 diabetes, *Science* 307(5708):384-387 (2005).

39. Maynard S. et al. Relationships between human vitality and mitochondrial respiratory parameters, reactive oxygen species production and dNTP levels in peripheral blood mononuclear cells. *Aging (Albany N.Y.)* 5(11):850-864 (2013).

40. Nakamura E., Miyao K., A method for identifying biomarkers of aging and constructing an index of biological age in humans, *J. Gerontol. A Biol. Sci. Med. Sci.* 62(10):1096-1105 (2007).

41. Nicholls G. et al., Bioenergetics of mitochondria in cultured neurons and their role in glutamate excitotoxicity, *J. Neurosci. Res.* 85(15):3206-3212 (2007).

42. Nicklas B. J. et al. Relationship of physical function to vastus lateralis capillary density and metabolic enzyme activity in elderly men and women. *Aging Clin Exp Res* 20(4):302-309 (2008).

43. Ostir G. V. et al., Assessing gait speed in acutely ill older patients admitted to an acute care for elders hospital unit, *Arch. Intern. Med.* 172(4):353-358 (2012).

44. Patti M. E. et al. Coordinated reduction of genes of oxidative metabolism in humans with insulin resistance and diabetes: Potential role of PGC1 and NRF1. *Proc Natl Acad Sci USA* 100(14):8466-8471 (2003).

45. Penninx B. W. et al., Lower extremity performance in nondisabled older persons as a predictor of subsequent hospitalization, *J. Gerontol. A Biol. Sci. Med. Sci.* 55(11):M691-M697 (2000).

46. Peterson C. M. et al., Skeletal muscle mitochondria and aging: a review, *J. Aging Res.* 2012:194821 (2012).

47. Phillips N. R. et al., Simultaneous quantification of mitochondrial DNA copy number and deletion ratio: a multiplex real-time PCR assay *Sci. Rep.* 4:3887 (2014).

48. Radom-Aizik S. et al., Brief bout of exercise alters gene expression in peripheral blood mononuclear cells of early- and late-pubertal males, *Pediatr. Res.* 65(4): 447-452 (2009).

49. Rao M., et al., Mitochondrial DNA injury and mortality in hemodialysis patients, *J. Am. Soc. Nephrol.* 20(1):189-196 (2009).

50. Rogers G. W. et al., High throughput microplate respiratory measurements using minimal quantities of isolated mitochondria. *PLoS One* 6(7):e21746 (2011).

51. Rolo P., Palmeira C. M., Diabetes and mitochondrial function: role of hyperglycemia and oxidative stress, *Toxicol. Appl. Pharmacol.* 212(2):167-178 (2006).

52. Rosenfeldt, et al., Coenzyme Q10 therapy before cardiac surgery improves mitochondrial function and in vitro contractility of myocardial tissue, *J. Thorac. Cardiovasc. Surg.* 129(1):25-32 (2005).

53. Rudkowska I. et al., Validation of the use of peripheral blood mononuclear cells as surrogate model for skeletal muscle tissue in nutrigenomic studies. *OMICS* 15(1-2):1-7 (2011).

54. Sansbury B. E. et al., Responses of hypertrophied myocytes to reactive species: implications for glycolysis and electrophile metabolism, *Biochem. J.* 435(2):519-528 (2011).

55. Shively C. A. et al., Aging and physical mobility in group-housed Old World monkeys, *Age (Dordr)* 34(5): 1123-1131 (2012).

56. Simonsick E. M. et al., Measuring fitness in healthy older adults: The health ABC long distance corridor walk, *J. Amer. Geriatric Soc.* 49:1544-1548 (2001)

57. Short K. R. et al., Decline in skeletal muscle mitochondrial function with aging in humans, Proc. Natl. Acad. Sci. U.S.A. 102(15):5618-5623 (2005).

58. Studenski S. What are the outcomes of treatment among patients with sarcopenia? *J. Nutr. Health Aging* 13(8):733-736 (2009).

59. Studenski S. et al., Gait speed and survival in older adults, *JAMA* 305(1):50-58 (2011).

60. Suomalainen A. et al., FGF-21 as a biomarker for muscle-manifesting mitochondrial respiratory chain deficiencies: a diagnostic study, *Lancet Neurol.* 10(9): 806-818 (2011).

61. Trounce I. et al., Decline in skeletal muscle mitochondrial respiratory chain function: possible factor in ageing. *Lancet* 1(8639):637-639 (1989).

62. Takamura T. et al., Gene expression profiles in peripheral blood mononuclear cells reflect the pathophysiology of type 2 diabetes. *Biochem Biophys Res Commun* 361(2):379-384 (2007).

63. van der Windt J. et al., Mitochondrial respiratory capacity is a critical regulator of CD8+ T cell memory development, Immunity 36(1):68-78 (2012).

64. Vericel E. et al., Platelets and aging. I—Aggregation, arachidonate metabolism and antioxidant status, *Thromb. Res.* 49(3):331-342 (1988).

65. Volpato S. et al., Performance-based functional assessment in older hospitalized patients: feasibility and clinical correlates, *J. Gerontol. A Biol. Sci. Med. Sci.* 63(12):1393-1398 (2008).

66. Volpato S. et al., Predictive value of the Short Physical Performance Battery following hospitalization in older patients, *J. Gerontol. A Biol. Sci. Med. Sci.* 66(1):89-96 (2011).

67. Woods S. C., Seeley, R. J., Adiposity signals and the control of energy homeostasis, *Nutrition* 16(10):894-902 (2000).

68. Yadava N., Nicholls, D. G. Spare respiratory capacity rather than oxidative stress regulates glutamate excitotoxicity after partial respiratory inhibition of mitochondrial complex I with rotenone, *J. Neurosci.* 27(27): 7310-7317 (2007).

The invention claimed is:

1. A method of determining increased morbidity in a subject, the method comprising the steps of:
(a) providing a blood sample obtained from the subject, wherein the subject is a human of at least 50 years of age;
(b) isolating circulating blood cells from the blood sample;
(c) distributing the isolated circulating blood cells into an analytical vessel; and,
(d) measuring respiratory capacity of the isolated circulating blood cells, wherein the measuring the respiratory capacity of the isolated circulating blood cells comprises measuring Maximum Oxygen Consumption Rate (Max OCR) and Spare Respiratory Capacity (SRC) of the circulating blood cells, wherein SRC is a difference between Max OCR and Basal Oxygen Consumption Rate (Basal OCR) of the circulating blood cells, and wherein the measuring the respiratory capacity of the isolated circulating blood cells comprises the steps of:
(I) measuring a first rate of oxygen disappearance from a medium to determine Basal OCR;
(II) adding an ATP synthase inhibitor to the medium;
(III) adding a mitochondrial uncoupler to the medium; and,
(IV) measuring a second rate of oxygen disappearance from the medium to determine Max OCR;
wherein the subject has increased morbidity compared to a reference population, if at least one of (i), (ii), or (iii) is measured in step (d):
(i) Max OCR of less than about 250 pmol/min/500,000 cells,
(ii) SRC of less than about 100 pmol/min/500,000 cells, or
(iii) SRC of 40% or less of Max OCR,
and wherein the reference population is a population in same age group as the subject and comprises one or both of
subjects with same type of ailment, disease, or disorder as the subject, or
subjects without the same type of the ailment, the disease, or the disorder as the subject.

2. The method of claim 1, wherein, when the at least one of (i), (ii), or (iii) is measured in step (d), the subject has a decreased likelihood of a positive clinical outcome compared to the reference population.

3. The method of claim 2, wherein the positive clinical outcome comprises at least one of responsiveness to treatment with nutraceuticals, benefit from a program of diet and exercise, responsiveness to physical rehabilitation, responsiveness to chemotherapy treatment, or improved recovery in cardiac rehabilitation or intensive care hospitalization treatment.

4. The method of claim 1, wherein the isolated circulating blood cells comprise isolated peripheral blood mononuclear cells.

5. The method of claim 1, wherein the isolated circulating blood cells comprise one or more of isolated monocytes, isolated lymphocytes, isolated platelets, or isolated neutrophils.

6. The method of claim 1, wherein the subject has exhibited clinical signs of a cardiac event or coronary heart disease.

7. The method of claim 1, wherein the subject has cancer.

8. The method of claim 1, wherein the reference population is a population of subjects with at least one of Max OCR of about 250 pmol/min/500,000 cells, SRC of about 100 pmol/min/500,000 cells, or SRC of about 40% of Max OCR.

9. The method of claim 1, wherein the reference population is a population of healthy subjects.

10. The method of claim 1, wherein the reference population is a population of subjects with same ailment, disease, or disorder as the subject.

11. The method of claim 1, wherein the reference population is a population of subjects in same age group as the subject.

12. The method of claim 1, further comprising
(e) administering a non-aggressive treatment to the subject, when at least one of one of (i), (ii), or (iii) is measured in step (d):
(i) Max OCR of less than about 250 pmol/min/500,000 cells,
(ii) SRC of less than about 100 pmol/min/500,000 cells, or
(iii) SRC of 40% or less of Max OCR.

13. The method of claim 12, wherein the non-aggressive treatment comprises patient monitoring or palliative care.

14. The method of claim 1, further comprising
(e) administering an aggressive treatment to the subject, when at least one of one of (i), (ii), or (iii) is measured in step (d):
(i) Max OCR of greater than about 250 pmol/min/500,000 cells,
(ii) SRC of greater than about 100 pmol/min/500,000 cells, or
(iii) SRC of 40% or greater of Max OCR.

15. The method of claim 14, wherein the aggressive treatment comprises one or more of surgery, drug or nutraceutical administration, physical rehabilitation, or change in diet or exercise regimen.

* * * * *